US012575721B2

(12) United States Patent
     Ghani et al.

(10) Patent No.: US 12,575,721 B2
(45) Date of Patent: Mar. 17, 2026

(54) DEVICES, SYSTEMS, AND METHODS FOR TREATING KIDNEY STONES

(71) Applicant: AMBU A/S, Ballerup (DK)

(72) Inventors: Khurshid Ghani, Ann Arbor, MI (US);
              Jeffrey Plott, Ann Arbor, MI (US);
              Morten Sørensen, Ballerup (DK)

(73) Assignee: AMBU A/S, Ballerup (DK)

( * ) Notice: Subject to any disclaimer, the term of this patent is extended or adjusted under 35 U.S.C. 154(b) by 555 days.

(21) Appl. No.: 17/514,777

(22) Filed: Oct. 29, 2021

(65) Prior Publication Data

US 2022/0053998 A1     Feb. 24, 2022

Related U.S. Application Data

(63) Continuation-in-part of application No. PCT/US2020/030605, filed on Apr. 30, 2020.
(Continued)

(30) Foreign Application Priority Data

May 21, 2021    (DK) ............................ PA 2021 70265
May 21, 2021    (DK) ............................ PA 2021 70266

(51) Int. Cl.
     *A61B 1/018*          (2006.01)
     *A61B 1/00*           (2006.01)
     (Continued)

(52) U.S. Cl.
     CPC .......... *A61B 1/018* (2013.01); *A61B 1/00006*
                   (2013.01); *A61B 1/00094* (2013.01);
                   (Continued)

(58) Field of Classification Search
     CPC ..... A61B 1/0057; A61B 1/015; A61B 1/0676;
                       A61B 1/00066; A61B 1/018;
     (Continued)

(56) References Cited

U.S. PATENT DOCUMENTS 1,770,045  A     7/1930   Shore et al.
2,421,449  A     6/1947   Zuber et al.
                (Continued)

FOREIGN PATENT DOCUMENTS

CN         2912540  Y      6/2007
CN       109431438  A      3/2019
                (Continued)

OTHER PUBLICATIONS

International Preliminary Report on Patentability received for PCT Patent Application No. PCT/US2020/030605, mailed on Nov. 11, 2021, 9 pages.
                (Continued)

*Primary Examiner* — Anh Tuan T Nguyen
*Assistant Examiner* — Li-Ting Song
(74) *Attorney, Agent, or Firm* — Faegre Drinker Biddle & Reath LLP

(57)                    ABSTRACT

An endoscope includes a handle including a handle housing, an irrigation inlet port adapted to receive irrigation fluid, and an irrigation channel; and an insertion cord extending distally from the handle. The insertion cord includes an insertion tube; a bending section extending from the insertion tube; a distal tip extending from the bending section and including a tip housing; a camera at least partially enclosed in the tip housing; interstitial space within the insertion tube in fluid communication with the irrigation channel; and at least one interstitial flow opening in fluid communication with the interstitial space and adapted to discharge the irrigation fluid.

18 Claims, 41 Drawing Sheets

Related U.S. Application Data

(60) Provisional application No. 62/915,149, filed on Oct. 15, 2019, provisional application No. 62/841,635, filed on May 1, 2019.

(51) Int. Cl.

| | |
|---|---|
| *A61B 1/005* | (2006.01) |
| *A61B 1/015* | (2006.01) |
| *A61B 1/05* | (2006.01) |
| *A61B 1/06* | (2006.01) |
| *A61B 1/307* | (2006.01) |

(52) U.S. Cl.
CPC ............ *A61B 1/0057* (2013.01); *A61B 1/015* (2013.01); *A61B 1/05* (2013.01); *A61B 1/307* (2013.01); *A61B 1/0676* (2013.01); *A61B 1/0684* (2013.01); *A61B 2217/007* (2013.01)

(58) Field of Classification Search
CPC . A61B 1/00006; A61B 1/00094; A61B 1/307; A61B 1/0684; A61B 2217/007; A61B 1/05

See application file for complete search history.

(56) References Cited

U.S. PATENT DOCUMENTS

| | | |
|---|---|---|
| 3,060,972 A | 10/1962 | Sheldon |
| 3,850,175 A | 11/1974 | Iglesias |
| 4,580,551 A | 4/1986 | Siegmund et al. |
| 4,651,718 A | 3/1987 | Collins |
| 4,911,148 A | 3/1990 | Sosnowski et al. |
| 4,950,278 A | 8/1990 | Sachse et al. |
| 4,998,916 A | 3/1991 | Hammerslag et al. |
| 5,089,895 A | 2/1992 | Fraker et al. |
| 5,176,126 A | 1/1993 | Chikama |
| 5,376,960 A | 12/1994 | Wurster |
| 5,379,756 A | 1/1995 | Pileski et al. |
| 5,418,566 A | 5/1995 | Kameishi |
| 5,438,975 A | 8/1995 | Miyagi et al. |
| 5,547,457 A | 8/1996 | Tsuyuki et al. |
| 5,688,222 A | 11/1997 | Hluchy et al. |
| 5,830,401 A | 11/1998 | Prichard et al. |
| 5,871,440 A | 2/1999 | Okada |
| 5,966,168 A | 10/1999 | Miyazaki |
| 6,004,263 A | 12/1999 | Nakaichi |
| 6,110,104 A | 8/2000 | Suzuki et al. |
| 6,156,049 A | 12/2000 | Lovato et al. |
| 6,302,616 B1 | 10/2001 | Takahashi |
| 6,375,651 B2 | 4/2002 | Grasso, III et al. |
| 6,456,863 B1 | 9/2002 | Levin et al. |
| 7,455,806 B2 | 11/2008 | Junger et al. |
| 7,758,495 B2 | 7/2010 | Pease et al. |
| 7,766,819 B2 | 8/2010 | Matsumoto |
| 7,981,027 B2 | 7/2011 | Miyagi et al. |
| 8,182,422 B2 | 5/2012 | Bayer et al. |
| 8,485,966 B2 | 7/2013 | Robertson |
| 8,547,424 B2 | 10/2013 | Ishii et al. |
| 8,784,298 B2 | 7/2014 | Fructus et al. |
| 9,089,297 B2 | 7/2015 | Heimberger |
| 9,155,453 B2 | 10/2015 | Kumar et al. |
| 9,339,283 B2 | 5/2016 | Carroux |
| 9,393,033 B2 | 7/2016 | Zerfas et al. |
| 10,004,385 B2 | 6/2018 | Bresco Torras et al. |
| 10,307,176 B2 | 6/2019 | Honda et al. |
| 10,321,804 B2 | 6/2019 | Jacobsen et al. |
| 10,335,020 B2 | 7/2019 | Oskin |
| 10,492,662 B2 | 12/2019 | Govrin et al. |
| 10,631,716 B2 | 4/2020 | Matthison-Hansen |
| 11,864,736 B2 | 1/2024 | Pereira et al. |
| 2002/0193663 A1 | 12/2002 | Matsuura |
| 2002/0198551 A1* | 12/2002 | Grant ...................... A61B 1/12 606/159 |
| 2003/0056540 A1 | 3/2003 | Mukasa et al. |
| 2003/0208209 A1 | 11/2003 | Gambale et al. |
| 2004/0199052 A1 | 10/2004 | Banik et al. |
| 2004/0242963 A1 | 12/2004 | Matsumoto |
| 2005/0070759 A1 | 3/2005 | Armstrong |
| 2005/0075538 A1 | 4/2005 | Banik et al. |
| 2005/0119527 A1 | 6/2005 | Banik et al. |
| 2005/0131279 A1 | 6/2005 | Boulais |
| 2005/0140068 A1 | 6/2005 | Junger et al. |
| 2005/0154262 A1 | 7/2005 | Banik et al. |
| 2005/0203341 A1 | 9/2005 | Welker et al. |
| 2005/0234499 A1 | 10/2005 | Olson et al. |
| 2006/0173244 A1 | 8/2006 | Boulais et al. |
| 2006/0178556 A1 | 8/2006 | Hasser et al. |
| 2007/0049800 A1 | 3/2007 | Boulais |
| 2007/0129466 A1 | 6/2007 | Kagawa et al. |
| 2007/0135682 A1 | 6/2007 | Miyagi et al. |
| 2007/0249896 A1 | 10/2007 | Goldfarb et al. |
| 2007/0249907 A1 | 10/2007 | Boulais |
| 2008/0091074 A1 | 4/2008 | Kumar et al. |
| 2008/0194911 A1 | 8/2008 | Lee |
| 2008/0221393 A1 | 9/2008 | Padget |
| 2008/0242935 A1 | 10/2008 | Inoue |
| 2008/0249483 A1 | 10/2008 | Slenker |
| 2008/0266441 A1 | 10/2008 | Ichimura |
| 2008/0268559 A1 | 10/2008 | Jung |
| 2008/0287741 A1 | 11/2008 | Ostrovsky |
| 2009/0054728 A1 | 2/2009 | Trusty |
| 2009/0105542 A1 | 4/2009 | Kitagawa et al. |
| 2009/0177040 A1 | 7/2009 | Lyons |
| 2009/0209819 A1 | 8/2009 | Kitagawa et al. |
| 2010/0210905 A1 | 8/2010 | Takeuchi et al. |
| 2010/0217082 A1 | 8/2010 | Ito et al. |
| 2010/0280316 A1 | 11/2010 | Dietz et al. |
| 2010/0324367 A1 | 12/2010 | Matsumoto et al. |
| 2011/0034771 A1 | 2/2011 | Konstorum |
| 2011/0166419 A1 | 7/2011 | Reif et al. |
| 2011/0184233 A1 | 7/2011 | Fructus et al. |
| 2011/0202039 A1 | 8/2011 | Schaaf |
| 2011/0230718 A1 | 9/2011 | Akui |
| 2011/0251519 A1 | 10/2011 | Romoscanu |
| 2012/0002981 A1 | 1/2012 | Park |
| 2012/0071716 A1 | 3/2012 | Fructus et al. |
| 2012/0165608 A1 | 6/2012 | Banik et al. |
| 2013/0023729 A1 | 1/2013 | Vazales et al. |
| 2013/0030249 A1 | 1/2013 | Vazales et al. |
| 2013/0041223 A1 | 2/2013 | Kato |
| 2013/0090529 A1 | 4/2013 | Boulais |
| 2014/0114129 A1 | 4/2014 | Peh |
| 2014/0210976 A1 | 7/2014 | Lin |
| 2014/0221749 A1* | 8/2014 | Grant ................. A61B 1/00096 600/109 |
| 2015/0305758 A1 | 10/2015 | Batchelor et al. |
| 2015/0366436 A1 | 12/2015 | Iuel |
| 2016/0051222 A1 | 2/2016 | Imahashi |
| 2016/0101254 A1 | 4/2016 | Hansen |
| 2016/0166320 A1 | 6/2016 | Ciulla et al. |
| 2016/0174819 A1* | 6/2016 | Ouyang ............. A61B 1/00098 600/105 |
| 2017/0188794 A1 | 7/2017 | Ouyang et al. |
| 2017/0215964 A1 | 8/2017 | Harrah et al. |
| 2017/0215965 A1 | 8/2017 | Harrah et al. |
| 2017/0238793 A1* | 8/2017 | Govrin ................... A61B 1/015 |
| 2018/0235441 A1 | 8/2018 | Huang et al. |
| 2018/0325357 A1 | 11/2018 | Boulais |
| 2019/0046223 A1* | 2/2019 | Dayton .......... A61B 17/320016 |
| 2019/0133705 A1 | 5/2019 | Riojas et al. |
| 2019/0142266 A1 | 5/2019 | Casarotto |
| 2019/0175007 A1 | 6/2019 | Sørensen et al. |
| 2019/0175799 A1 | 6/2019 | Hsu et al. |
| 2019/0298321 A1* | 10/2019 | Intintoli ................... A61B 1/07 |
| 2020/0054196 A1 | 2/2020 | Govrin et al. |
| 2020/0138268 A1 | 5/2020 | Matthison-Hansen et al. |
| 2020/0196843 A1 | 6/2020 | Tah et al. |
| 2020/0196848 A1 | 6/2020 | Lin |
| 2020/0383675 A1 | 12/2020 | Jung |
| 2021/0030261 A1 | 2/2021 | Kress |
| 2021/0137354 A1 | 5/2021 | Bob et al. |
| 2021/0186316 A1 | 6/2021 | Thommen et al. |

(56) References Cited

U.S. PATENT DOCUMENTS

| | | | |
|---|---|---|---|
| 2021/0386442 A1 | 12/2021 | Heimberger | |
| 2022/0000350 A1* | 1/2022 | Heimberger | A61B 1/0055 |

FOREIGN PATENT DOCUMENTS

| | | |
|---|---|---|
| CN | 208784694 U | 4/2019 |
| CN | 109875681 A | 6/2019 |
| CN | 110037646 A | 7/2019 |
| CN | 209154018 U | 7/2019 |
| CN | 209301083 U | 8/2019 |
| CN | 209346976 U | 9/2019 |
| CN | 209499675 U | 10/2019 |
| CN | 209864037 U | 12/2019 |
| CN | 210643992 U | 6/2020 |
| DE | 102018108843 A1 | 10/2019 |
| EP | 3669746 A1 | 6/2020 |
| GB | 383223 A | 11/1932 |
| GB | 2268883 A | 1/1994 |
| WO | 1996022739 A1 | 8/1996 |
| WO | 00/56387 A1 | 9/2000 |
| WO | 2004026125 A1 | 4/2004 |
| WO | 2012/060932 A2 | 5/2012 |
| WO | WO 2014/106511 | 7/2014 |
| WO | 2015058329 A1 | 4/2015 |
| WO | WO 2019/002186 | 1/2019 |
| WO | 2020150713 A2 | 7/2020 |
| WO | WO 2020/223429 | 11/2020 |
| WO | 2022/243553 A2 | 11/2022 |

OTHER PUBLICATIONS

Examination and Search Report for Denmark Application No. DK PA202170265, mailed on Nov. 17, 2021, 7 pages.

Examination and Search Report for Denmark Application No. DK PA202170266, mailed on Dec. 15, 2021, 9 pages.

International Search Report and Written Opinion received for PCT Patent Application No. PCT/EP2022/063812, mailed on Nov. 22, 2022, 16 pages.

International Search Report and Written Opinion of International Application No. PCT/US2020/030605, mailed Jul. 22, 2020, 10 pgs.

First technical report in related Danish Patent Application No. PA 2021 70265, dated Nov. 17, 2021, 7 pages.

First technical report in related Danish Patent Application No. PA 2021 70266, dated Dec. 15, 2021, 9 pages.

Extended European search report in related European Application No. 20798662.1, dated Dec. 14, 2022, 8 pages.

* cited by examiner

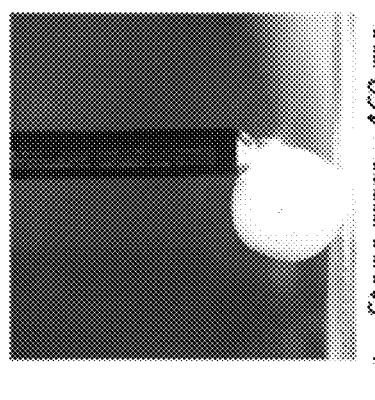
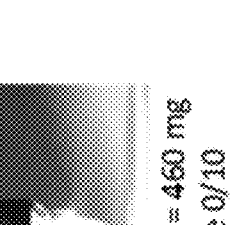
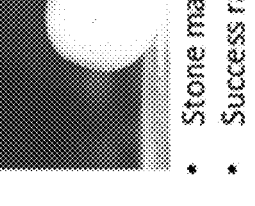
* Stone mass = 460 mg
* Success rate 0/10
FIG. 32d
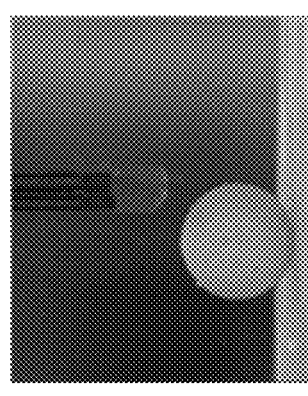
* Stone mass = 460 mg
* Success rate 9/10
FIG. 33d
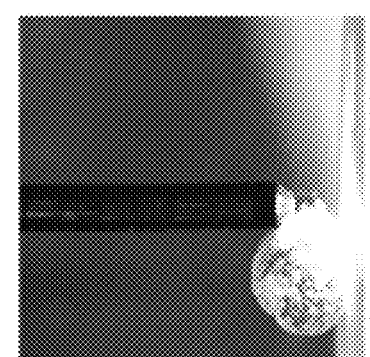
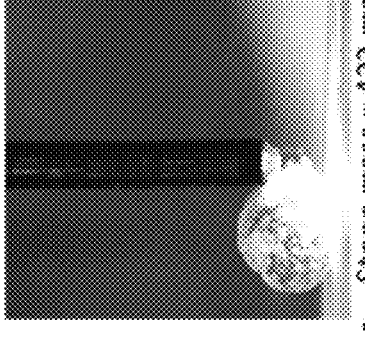
* Stone mass = 422 mg
* Success rate 3/10
FIG. 32c
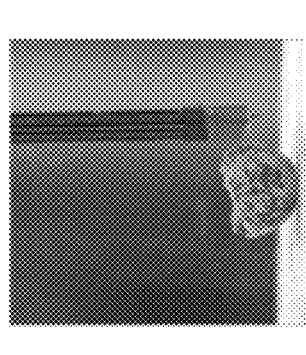
* Stone mass = 422 mg
* Success rate 6/10
FIG. 33c
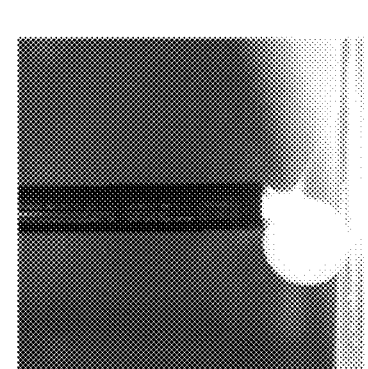
* Stone mass = 207 mg
* Success rate 10/10
FIG. 32b
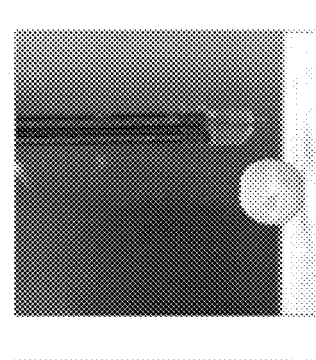
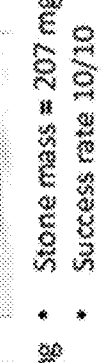
* Stone mass = 207 mg
* Success rate 10/10
FIG. 33b
* Stone mass = 194 mg
* Success rate 10/10
FIG. 32a
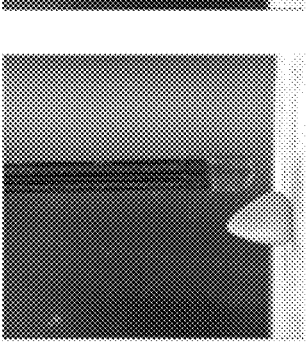
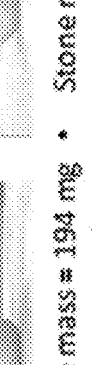
* Stone mass = 194 mg
* Success rate 10/10
FIG. 33a

DEVICES, SYSTEMS, AND METHODS FOR TREATING KIDNEY STONES

CROSS REFERENCE TO RELATED APPLICATIONS

This application is a continuation-in-part of International Application No. PCT/US2020/030605, filed Apr. 30, 2020, which claims priority to and the benefit of U.S. Provisional Application No. 62/841,635, filed May 1, 2019, and U.S. Provisional Application No. 62/915,149, filed Oct. 15, 2019; this application also claims priority to and the benefit of Danish Patent Applications Nos. PA 2021 70265, filed May 21, 2021, and PA 2021 70266, filed May 21, 2021; the contents of the aforementioned applications are incorporated herein by reference in their entireties.

FIELD

The disclosure relates to endoscopes and, in particular, to endoscopes with irrigation channels and ureteroscopes.

BACKGROUND

Kidney stone disease, also known as urolithiasis, is characterized by the presentation of a solid piece of material (known as a calculus or kidney stone) in the urinary tract. Kidney stones typically form in the kidney and leave the body in the urine stream. A small stone may pass without causing symptoms. If a stone grows to more than 5 millimeters (0.2 inches), it can cause blockage of the ureter resulting in severe pain in the lower back or abdomen. A stone may also result in blood in the urine, vomiting, or painful urination. About half of people who experience a kidney stone will have another stone within ten years.

Treatments for kidney stones include medical expulsive therapy (e.g., using alpha adrenergic blockers (such as tamsulosin) or calcium channel blockers (such as nifedipine)), extracorporeal shock wave lithotripsy (ESWL), ureteroscopic surgery, and percutaneous nephrolithotomy surgical procedures.

However, existing technologies are limited by potential side effects and incomplete stone removal. Accordingly, a need exists for improved methods of treating kidney stones.

SUMMARY

Provided herein are devices, systems, and methods for treating kidney stones. In particular, provided herein are endoscopic (e.g., ureteroscope) devices with improved properties, as well as systems, and related methods for use in treating kidney stones and other applications.

The devices described herein solve a number of problems with existing endoscopic devices, for example, by improving visualization of stones when an instrument is in the working channel, reducing intrarenal pressure, eliminating the need for a basket for stone repositioning, providing the option of symmetrical working channels for better targeting stones, and providing suction that sucks the stone, stabilizes the stone, and evacuates stone dust and debris.

In one aspect, an endoscope is provided that comprises a handle including a handle housing, an irrigation inlet port adapted to receive irrigation fluid, and an irrigation channel; and an insertion cord extending distally from the handle. The insertion cord includes an insertion tube; a bending section extending from the insertion tube; a distal tip extending from the bending section and including a tip housing; a camera at least partially enclosed in the tip housing; interstitial space within the insertion tube in fluid communication with the irrigation channel; and at least one interstitial flow opening in fluid communication with the interstitial space and adapted to discharge the irrigation fluid.

An another aspect, a visualization system is provided comprising an endoscope according to the first aspect and a video processing apparatus operable to receive live images from the endoscope.

An a further aspect, a method of irrigating a space within a patient is provided, the method comprising: inserting the insertion cord of the endoscope according to the first aspect into the patient; supplying irrigation fluid to the irrigation channel of the endoscope, the irrigation fluid flowing through the interstitial space and discharging through the at least one interstitial flow opening to irrigate the space.

In some embodiments, an endoscope (e.g., ureteroscope) comprises an end (e.g., tip) (e.g., defined herein as the distal end but also can be defined as the proximal end, depending on perspective), the distal end comprising: a) a first channel (e.g., configured for delivery and/or removal of fluid and a laser or configured for suction); and b) a second channel (e.g., configured for delivery of fluid and a laser or configured to remove fluid via suction), wherein the second channel exits the distal end on a different plane than the first channel (e.g., the first and second channel exits are in different planes with respect to the plane created by the distal end of the endoscopic device), and wherein the exit of the first or second channel comprises a suction port. In some embodiments, each channel has an opening substantially planar (i.e., greater than 90% of its area is on the single plane). In some embodiments, the plane of the first channel exit is in the plane of the distal end. In some embodiments, the plane of the distal end is perpendicular to the longitudinal axis of the endoscopic device. In some embodiments, the plane of the distal end is substantially perpendicular (+/−10 degrees of perpendicular) to the longitudinal axis of the longitudinal axis of the endoscopic device.

Further provided is an endoscope comprising a working (e.g., tip or distal) end, the distal end comprising: a) a first channel configured for delivery of fluid and optionally a laser; and b) a second channel configured to remove fluid via suction and optionally delivery of a laser, wherein the second channel exits the end on a different plane than the first channel and wherein the exit of the second channel comprises a suction port, and wherein the first and second channels are configured to prevent stones from occluding the suction port.

Also provided is an endoscopic device comprising a distal end, the distal end comprising: a) a first channel configured for delivery of fluid and optionally a laser; and b) a second channel configured to remove fluid via suction and optionally delivery of a laser, wherein the second channel exits the distal end on a different plane than the first channel and wherein the exit of the second channel comprises a suction port, wherein the suction port comprises a plurality of protrusions and/or depressions.

Yet other embodiments provide an endoscopic device comprising a distal end, the distal end comprising: a) a first channel configured for delivery of fluid and optionally a laser; and b) a second channel configured to remove fluid via suction and optionally delivery of a laser, wherein the second channel exits the distal end on a different plane than the first channel and wherein the exit of the second channel comprises a suction port, and wherein the suction port is on a protrusion.

Certain embodiments provide an endoscopic device comprising a distal end, the distal end comprising: a) a first channel having an exit in a first plane configured for delivery of fluid and optionally a laser; and b) a second channel having an exit in a second plane and wherein the exit of the second channel comprises a suction port and wherein said second channel is optionally configured for delivery of a laser.

In some embodiments, the distal end of the endoscopic device further comprises one or more additional components, for example, a camera and/or a light. In some embodiments, the camera is positioned above the suction port, partially above the suction port, level, partially below the suction port or below the suction port (e.g., in a cut out of the distal region). In some embodiments, the location of the camera and the light are interchangeable. In some embodiments, the light comprises a fiber optic filament or one or more LEDs. In some embodiments, the camera and the light are located proximal or distal to each other. In some embodiments, the camera is located on a plane above the plane of the working channel and/or suction port. In some embodiments, the working channel and/or suction port are angled out and away from the camera (e.g., at an angle of 120-160 degrees about an X-axis of the endoscopic device and/or 5-25 degrees about a line on the YZ-plane of the endoscopic device, although other angles are specifically contemplated).

In some embodiments, the endoscopic device further comprises a laser slider configured to move the laser about the longitudinal axis of the endoscopic device. In some embodiments, actuation of the laser slider unclogs stone fragments stuck in the working channel.

In some embodiments, the suction port comprises one or more anti-clog elements (e.g., including but not limited to, one or more of the port or channel in operable communication with the port comprising a smaller inner diameter than suction tubing in operable communication with the port, a mesh material that covers the opening, a bar or beam that covers the opening, and/or one or more protrusions or depressions adjacent to the opening). In some embodiments, the anti-clog elements prevent occlusion of the suction port, working channel or suction channel by a kidney stone or fragments thereof. In some embodiments, the distal opening of the first and/or second channel comprises a mesh or filter. In some embodiments, the filter is pivotable and/or flexible (e.g., to allow an instrument to fit through the opening) or comprises an opening for an instrument.

In some embodiments, the region of the distal end surrounding the suction port is flat, rounded, concave, or protruded. In some embodiments, the first and second channels are located adjacent or distal to each other. In some embodiments, the exit of the first channel and/or exit of second channel is substantially planar or substantially in the first and/or second plane. In some embodiments, the suction port and working channel are on symmetrical planes relative to the longitudinal axis of the endoscopic device. In some embodiments, the suction port and working channel are on asymmetrical planes relative to the longitudinal axis of the endoscopic device. In some embodiments, the suction port and working channel are interchangeable. In some embodiments, the channel configured for a laser is also used for removal of fluid via suction.

In some embodiments, the distal end further comprises one or more flow diverters configured to direct fluid flow towards the second or suction channel. In some embodiments, the flow diverter is located at the opening of the first or second channel. Devices may comprise one or more (e.g., 1, 2, 3, 4, or more) flow diverters of the same or different types located at the same or different locations relative to the first and second channels. In some embodiments, the flow diverters are in fluid communication with the first and/or second channels.

In some embodiments, the first and second channels have the same or different diameters. For example, in some embodiments, the first channel has an inner diameter of 0.4 to 0.6 mm (e.g., sized for a laser) and the second channel has an inner diameter of 1.1 to 1.3 mm (e.g., sized for suction and/or irrigation).

The present disclosure is not limited to particular materials for constructing endoscopic devices or an end of the endoscopic device. In some embodiments, at least a portion of the distal end is constructed of a compliant material (e.g., including but not limited to, a silicone elastomer, a thermoplastic elastomer, or a foam). In some embodiments, the compliant material surrounds or comprises the suction port. In some embodiments, the compliant material is configured to deform to fit the shape of a kidney stone. In some embodiments, the compliant material has a Shore hardness of between OO10 and A40. In some embodiments, at least a portion of the distal end is constructed of a material selected from, for example, a thermoplastic, a metal, or a combination thereof (e.g., a material with a hardness of greater than A40 on the Shore hardness scale).

In some embodiments, the endoscopic device comprises an outer housing (e.g., outer housing and/or outer jacket) surrounding an interstitial space, wherein the distal end or distal portion of the endoscopic device comprises one or more interstitial flow openings in fluid communication with the interstitial space, wherein the interstitial flow openings are configured to deliver fluids or suction through such interstitial space; and a fluid port and/or suction component (e.g. located at the proximal end of the endoscopic device (e.g., in the handle) or another location).

Also provided herein is an endoscopic device, comprising: a) an outer housing surrounding an interstitial space, wherein the distal end or distal portion of the endoscopic device comprises one or more interstitial flow openings in fluid communication with the interstitial space, wherein the interstitial flow openings are configured to deliver fluids or suction through the interstitial space. In some embodiments, the outer housing further comprises a fluid port in fluid communication with the interstitial space. In some embodiments, the fluid port is located at the proximal end of the endoscopic device (e.g., in the handle). In some embodiments, the endoscopic device further comprises a working channel. In some embodiments, the interstitial space comprises one or more of a sensor wire, a camera wire, a pull wire, a light wire, or a fiber optic cable or wire.

Further provided is an endoscopic device comprising a distal end, the distal end comprising: a) a first channel or opening configured for delivery of fluid; and b) a second channel or opening configured to remove fluid via suction, wherein the second channel exits the distal end on a different plane than said first channel, and wherein the distal end further comprises one or more flow diverters, wherein the flow diverters are configured to direct fluid flow from the first channel or opening towards the second channel or opening.

Further embodiments provide a system, comprising: a) an endoscopic device as described herein; and b) an irrigation delivery system and a suction system. In some embodiments, the system further comprises a temperature sensor and/or pressure sensor at the distal end. In some embodiments, the system further comprises a computer system configured to adjust the irrigation delivery system and the suction system based on readings from the temperature and pressure sensors. In some embodiments, the adjusting maintains temperature and pressure of the fluid at the distal end within a range that reduces or prevents side effects due to excess pressure and/or temperature during use. In some embodiments, the adjusting increases or decreases suction to securely hold a stone and/or release a stone for repositioning within the kidney or extraction through the ureter.

Yet other embodiments provide a method of ablating a kidney stone, comprising: a) introducing an endoscopic device as described herein into the ureter of a subject; b) advancing the endoscopic device to a kidney or ureteral stone; and c) ablating the stone using the endoscopic device.

Additional embodiments are described herein.

DESCRIPTION OF THE DRAWINGS

FIG. 4b is a side view of the bending section of FIG. 4a;

FIGS. 32a-33d are images representing a comparison of suction of model kidney stones using an existing ureteroscope and a device of embodiments of the present disclosure.

DESCRIPTION

While the present disclosure may be exemplified with an ureteroscope and methods of using the ureteroscope for treating kidney stones, the apparatus and methods described herein find use with any minimally invasive medical device, including but not limited to, endoscopes.

As used herein, the term "proximal" refers to the portion of the endoscope closest to the medical practitioner and the term "distal" refers to the portion of the endoscope furthest away from the medical practitioner. Thus, the handle is at the proximal end and the tip is at the distal end.

Figure 1A:
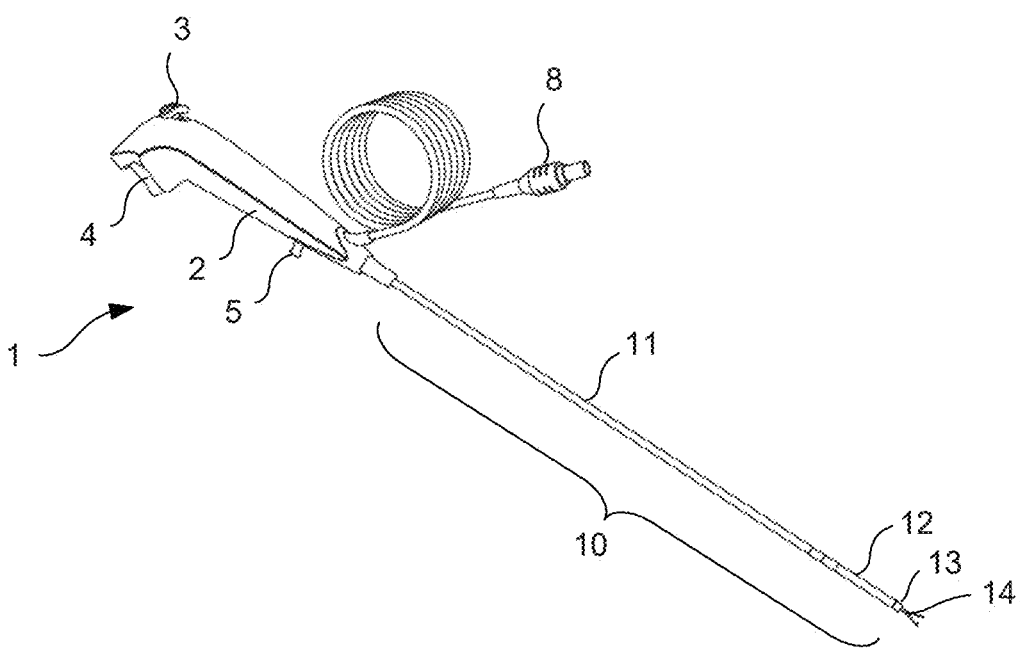
FIG. 1a is a perspective view of an embodiment of an endoscope.

FIG. 1a shows an endoscope 1 having a control handle 2 and an insertion cord 10 attached to the control handle 2. The insertion cord 10 includes an insertion tube 11, a bending section 12, and a distal tip 13 including a camera. An optional tool 14 is shown. The control handle 2 is here provided with a control lever 3 which enables an operator of the endoscope 1 to control the bending of the bending section 12 through pull wires, which by being tensioned or slacked can bend the bending section in one plane. The bending section could alternatively be controlled by pull wires in two planes. A suction button 4 and a suction port 5 are also shown. Upon actuation of the suction button 4 a vacuum is applied to a working channel connected to the suction port. Fluids suctioned through the distal tip 13 are thereby drawn out and discharged via the suction port 5. A source of vacuum (not shown) is also connected to the control handle 2. An image captured by the camera can be transmitted via a cable connector 8 to a video processing apparatus. Example video processing apparatus include apparatus with and without integrated display screens. A video processing apparatus with an integrated display screen can be referred to as a monitor. A display screen can be connected to video processing apparatus via a cable, e.g. HDMI or ethernet, or wirelessly.

Figure 1B:
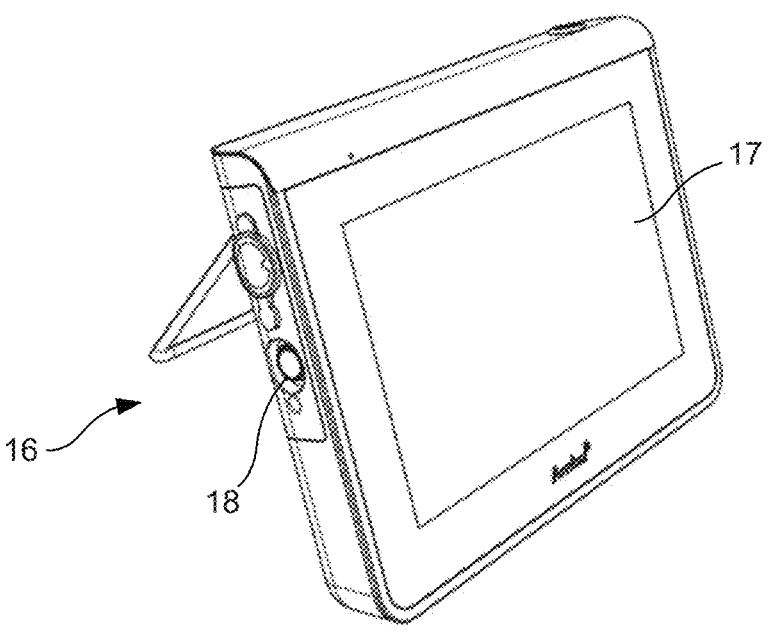
FIG. 1b is a perspective view of an embodiment of a video processing apparatus.

FIG. 1b shows a video processing apparatus, i.e. monitor 16, for displaying the image obtained by the camera of the endoscope 1. The monitor 16 includes a display screen 17 and a connector port 18. The cable connector 8 may be connected to the connector port 1 to present live images with the display screen 17. Aspects of the endoscope 1, in particular aspects relating the bending system, control lever connection to the pull wires, and other aspects are known from commonly owned U.S. Patent Publication Nos. 2020/0138268 and 10,631,716, which are incorporated herein by reference.

Existing endoscopes and other devices rely on dedicated channels, or lumens, for either irrigation or suction of fluid. Especially small diameter endoscopes, there is a need to minimize the outer diameter of the insertion cord to reduce the trauma to the patient when the device is inserted, for example into the ureter. Ureteroscopes typically have outer diameters of approximately between 7-10 (e.g., 8-10) French (Fr). However, the smaller the outer diameter becomes, the less room there is to fit multiple dedicated working channels (e.g., one for irrigation and one for suction).

Accordingly, in some embodiments, provided herein is a device that overcomes this limitation by utilizing the interstitial space, e.g. interstitial lumen, inside the insertion cord to deliver irrigation fluid at or near the tip of the device while simultaneously using the working channel for fluid suction and/or other device components. This greatly improves visualization for the procedure while enabling a smaller device outer diameter. In practice, irrigation fluid can be pressurized and flow from an irrigation inlet port 47 in the handle, as described with reference to FIGS. 2a, 2b and 3a, through the interstitial space within the insertion cord, and exit the endoscope through the one or more interstitial flow openings. In some embodiments, these openings are at the distal tip to help clear away debris from the field of view, although the present disclosure is not limited to a particular location. Examples include, but are not limited to, on the top surface of the tip, the side surface of the tip, through an opening on the insertion tube or the bending section, or a combination thereof. Although various features are described with reference to ureteroscopes for illustrative purposes, the features may be incorporated in endoscopes used for a variety of procedures and not only in ureteroscopes. Accordingly, references to the kidney and kidney stones can be generalized to tissue of the patient and objects, including kidney stones, debris and tissue.

Figures 2A, 2B:
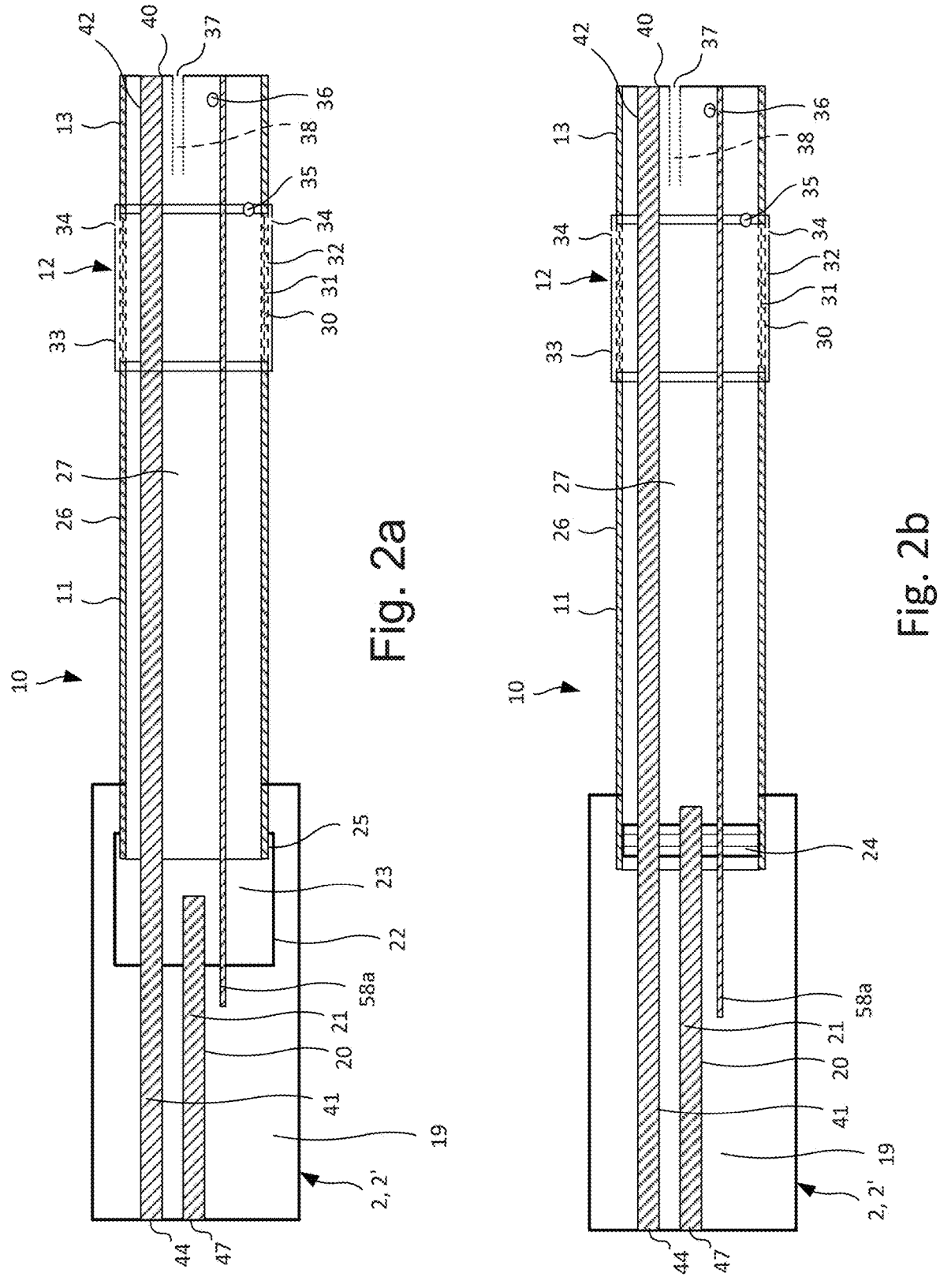
FIGS. 2a and 2b are schematic views of endoscopes including irrigation systems.

FIGS. 2a and 2b are schematic views of endoscopes including irrigation systems as described in the preceding paragraph and the figures below. Generally, the endoscopes include the control handle 2, 2', the insertion cord 10 including the insertion tube 11, the bending section 12, and the distal tip 13. A working channel port 40 is provided at the end of a working channel 41. A working channel tube 42 may define part of the working channel. The working channel port 40 is typically molded in a tip housing of the distal tip. The working channel port 40 can also be provided, if the working channel tube 42 extents to the distal end of the distal tip, by the working channel tube 42 without a molded portion. The working channel port can be considered to be the portion of the tube or molded portion that defines the opening. In the figures below the working channel port is discussed in the context of its position in various planes and in relation to other components at the distal tip 13.

An irrigation tube 20 defining within it an irrigation channel 21 is provided in the control handle 2, 2' and is discussed with reference to FIG. 3a. The irrigation tube 20 extends to a fluid junction body 22 (described with reference to FIGS. 9a-12b) establishing fluid communication between an irrigation inlet port 47 (see FIG. 3a), an internal space 23 of the fluid junction body 22, and the interstitial space 27 of the insertion tube 11. The fluid junction body 22 may receive the proximal end of the outer housing 26 and be fluid sealed thereto at a seal 25. In FIG. 2b the fluid junction body comprises a seal body 24 positioned at the proximal end of the insertion tube 11 and the irrigation tube 20 extends through the seal body 24 into the insertion tube 11. In both embodiments irrigation fluid flows through the irrigation tube 20 into the interstitial space 27.

FIGS. 2a and 2b also show features of the bending section 12, which includes segments 30 connected by hinges 31 and defining open spaces 32 between adjacent segments 30. The proximal and distal segments may be referred to a segments 30a and 30b. A bending section sleeve 33 extends over the bending section 12 and is bonded at both ends to enclose and fluid seal, except with respect to interstitial flow openings, the open spaces 32. Interstitial flow openings 34, 35, 36, and 37 are shown. The interstitial flow opening 34 is formed in the bending section sleeve 33. The interstitial flow opening 35 is formed between the bending section sleeve 33 and a segment 30 or the tip housing, preferably the distal segment 30b. The interstitial flow opening 36 is formed in a wall of the bending section sleeve 33. The interstitial flow opening 35 is formed in the distal segment 30b or the tip housing. The interstitial flow opening 37 is formed in a front or distal wall or window of the distal tip 13. A portion of the irrigation channel 21 is provided by the interstitial space 27. Another portion of the irrigation channel 21 can be provided by forming or molding an elongate cavity, 38, in the distal tip 13, which may be referred to as a distal tip irrigation channel portion 38. The interstitial irrigation channel and flow openings are further disclosed with reference to FIGS. 5a, 6a-d, 7b, and 8a. An example pull cable 108 is also shown.

Figures 3A, 3B:
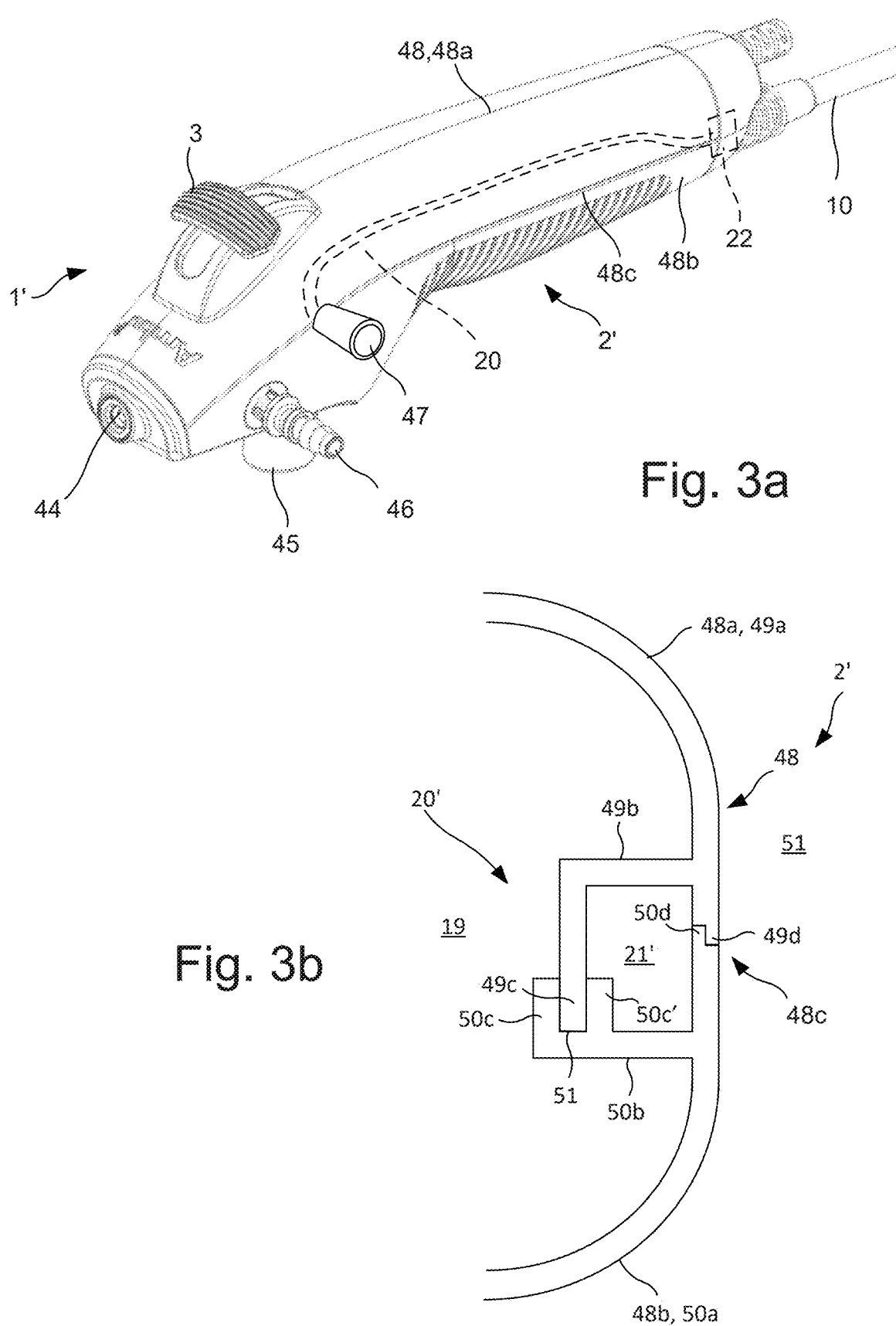
FIG. 3a is a perspective view of an embodiment of a handle of an endoscope.
FIG. 3b is a cross-section view of a portion of an embodiment of a handle showing an irrigation channel.

FIG. 3a shows another embodiment of a control handle of an endoscope, denoted by numerals 1' and 2' respectively. The control handle 2' is in most respects the same as the control handle 2. Additionally, the control handle 2' comprises the irrigation inlet port 47 connected via the irrigation tube 20 to the fluid junction body 22 (described with reference to FIGS. 9a-12b) fluidly connecting the irrigation inlet port 47 to the interstitial space 27 of the insertion tube 11. The control handle 2' (and also the control handle 2) comprises a handle housing 48 comprised of mating housing parts 48a and 48b which form a housing joint 48c. Also shown are a working channel inlet port 44, a fluid discharge port 45, and a suction inlet port 46. Tools can be inserted through the channel inlet port 44. When suction is applied via a suction channel, the fluid is discharged via the fluid discharge port. The suction inlet port 46 is connected to a vacuum source that can be engaged to provide suction via the suction port, e.g. port 302.

The irrigation tube 20 may, in an alternative embodiment shown in FIG. 3b, be integrally molded with the housing parts 48a and 48b, which comprise internal walls sized and shaped to form an integral irrigation tube 20' with an irrigation channel 21'. The handle housing 48 separates an internal space 19 from an external space 19'. The irrigation channel 21' may extend from the irrigation inlet port 47 to the fluid junction body 22. The mating housing parts 48a, 48b include peripheral walls 49a, 50a, respectively, and internal walls 49a, 50 extending therefrom toward the internal space 19. The internal walls 49b, 50b connect with each other defining the irrigation channel 21'.

The internal walls 49b, 50b may connect with each by interlocking ensure a fluid seal for the irrigation channel 21'. In some variations, the interlocking may be provided by two wall portions of one of the housing parts forming a channel for a wall portion of the other of the housing parts. An example of such an interlocking is provided by wall portions 50c and 50c' of the internal wall 50b providing a channel or groove 50d for a wall portion 49c, or tongue, of the internal wall 49b. The channel interlocking, known as a "tongue and groove" joint, may also be formed on the peripheral walls 49a, 50a.

In some variations, the interlocking may be provided by a wall portion of one of the housing parts mating, without forming a channel, with a wall portion of the other of the housing parts. An example of such a channelless interlocking is provided by wall portions 49d and 50d of the peripheral walls 49a, 50a, where each of the wall portions 49d and 50d overlaps the other. Each of the wall portions 49d and 50d abuts the opposite peripheral wall 49a, 50a. Their thicknesses in the overlapping portion may be less than the thickness of the peripheral wall, preferably both thicknesses adding up to the thickness of the peripheral wall. The channelless interlocking, also known as a "half lap" joint, may also be formed on the internal walls 49b, 50b instead of the tongue and groove joint.

As shown, the tongue and groove joint provides a more secure seal, protecting the internal components of the control handle 2, 2' while the half lap joint keeps the irrigation fluid from leaking to the outside space. However, the stresses provide by the tongue and groove joint on the internal walls can also press the portions of the half lap joint against each other to improve the external seal. Of course the seals could also be enhanced by the addition of an adhesive between portions of the joints.

Figure 4A:
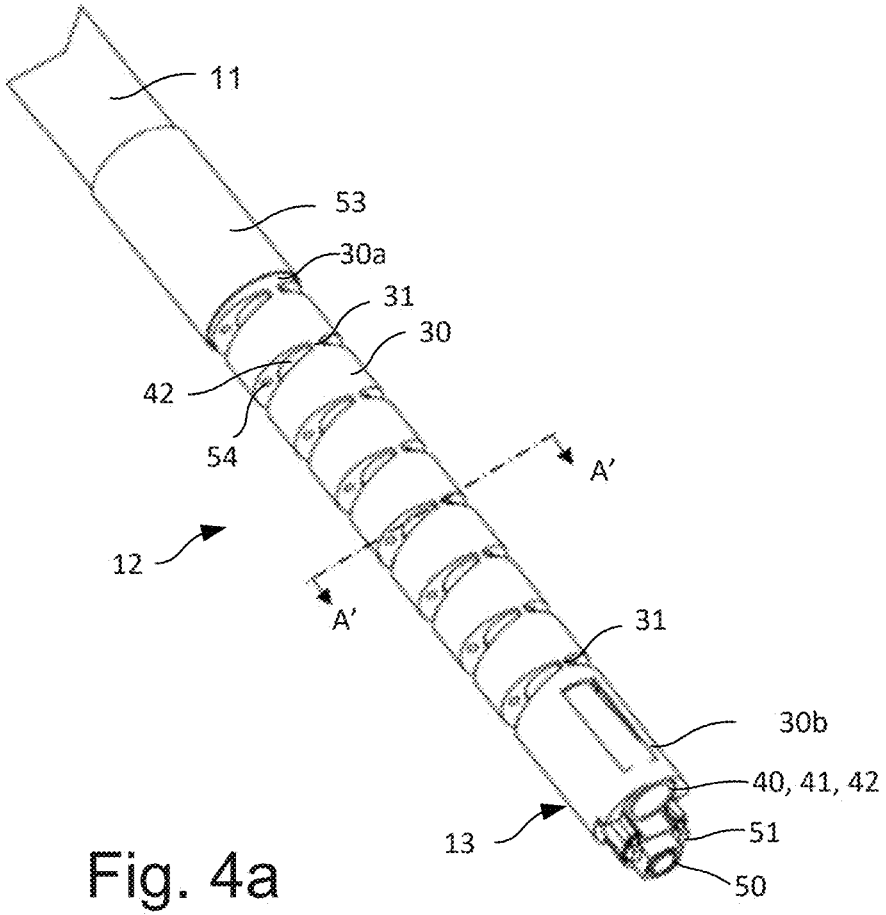
FIG. 4a is a perspective view of an embodiment of a bending section and distal tip.

Having discussed the control handle attention is now directed to bending section and the distal tip. FIG. 4a shows an embodiment of the bending section 12 and the distal tip 13. Here, the bending section sleeve or cover 33 is not shown to clearly show the structure of the bending section. Also, the molding plastic housing of the distal tip is not shown. The bending section 12 includes a number of segments including a distal end segment 30b, a proximal end segment 30a connected to the insertion tube 11, and a number of segments 30 arranged between the distal end segment 30b and the proximal end segment 30a. The segments 30, 30a, 30b are interconnected by hinges 31. These hinges 31 are preferably integrally made from the same material as the segments, and preferably the hinges and the segments form a single continuous piece of material. Examples of materials could be polypropylene, polyacetal (POM) or a semi-aromatic polyamide (nylon). The distal tip 13 comprises a camera 50, light emitting diodes 51 and the working channel port 40. The working channel may be used for removal of liquid or for the introduction of a tool e.g. an optical fiber or tool 14 or a laser fiber/shaft, discussed below. The working channel can also be used to irrigate. A sleeve 53 may be used to secure the bending section 12 to the insertion tube 11, for example with an adhesive or press-fit or both. The sleeve 53 may be part of the proximal end segment 30a. The protective tube or sleeve (not shown) of the bending section 12 can abut the distal edge of the sleeve 53 and be bonded to the proximal end segment 30a to fluidly seal the bending section. As shown, the distal tip 13 comprises the distal end segment 30b. The distal tip 13 can also be connected to but not comprise the distal end segment 30b. The bending section 12 can be used with the embodiments of endoscopes described with reference to FIGS. 1a, 2a, 2b, and 3a and also with the endoscopes described below. FIG. 4a also shows passages 54 for the positioning of the pull wires (shown in FIGS. 6a-6c). The pull wires are arranged inside sheaths (or guide tubes), thereby forming Bowden, or pull, cables 108 (see FIG. 9a). The guide tubes terminate at the proximal segment 30a, and the pull wires continue through the passages 54 in the bending section, which form a guiding channel for the pull wires and are preferably placed close to the outer periphery of the bending section. The pull wires extend from the control handle 2, 2' to the distal end segment 30b of the bending section. The pull wires are secured to the distal end segment 30b or to the distal tip 13. This configuration together with the hinges 31 allows for the bending of the bending section by tensioning one pull wire and slacking the other. Pull wires are further discussed with reference to FIGS. 4b and 6a.

Figure 4B:
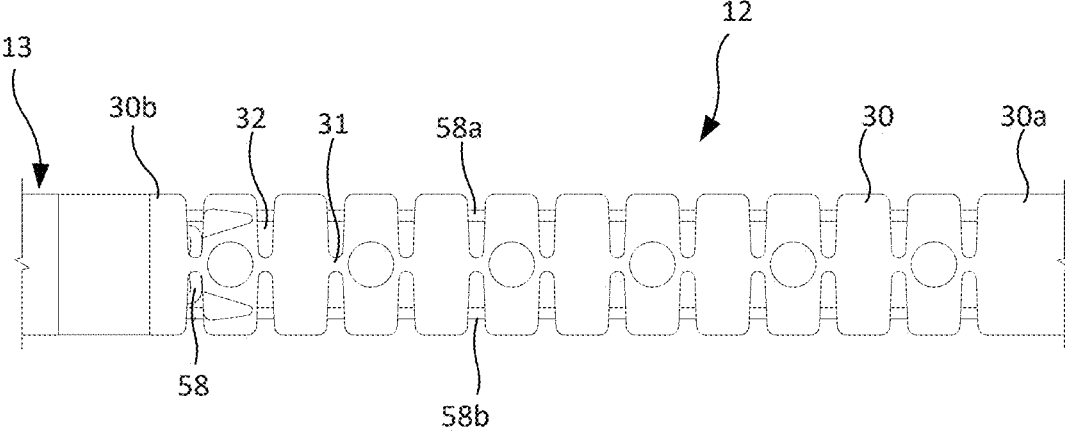

FIG. 4b illustrates a pull wire 58 having proximal sections 58a and 58b. These embodiments show how pull wire 58 can be secured to the distal end segment 30b or to the distal tip 13. The pull wire 58 can also comprise two wires secured to the distal end segment 30b or to the distal tip 13, for example by potting. The open spaces 32 are also shown.

Figures 5A, 5B, 5C:
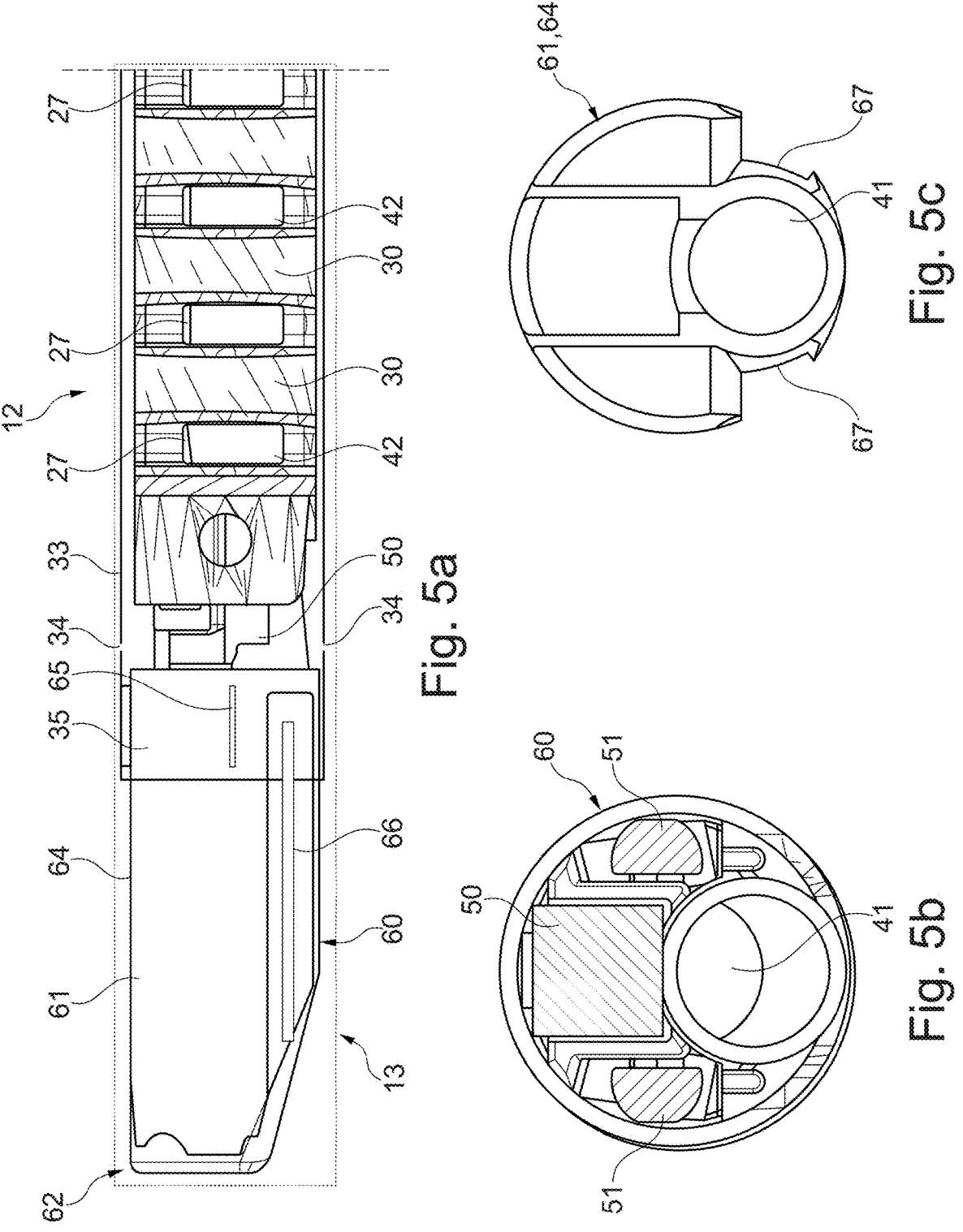
FIGS. 5a-5c are views of an embodiment of a bending section and distal tip.

FIGS. 5a-c illustrate embodiments of the interstitial fluid openings. Shown are the bending section 12 and the bending section sleeve 33. The distal tip 13 comprises an elongate tip housing 60 connected to the distal segment 30b and having a circumferential wall 61 and a distal, or front, wall 62 connected to the wall 61. The wall 61 has an outer surface 64. As shown, the distal segment 30b is not yet connected to the tip housing 60, for illustrative purposes. The bending section 12 has interstitial space also, provided space between the various apertures, tubes, and components passing therethrough. The interstitial space in the bending section is in fluid communication with the interstitial space 27 of the insertion tube since the insertion tube 11 and the proximal segment 30a are connected at their peripheries. Each of the embodiments described herein describing interstitial fluid openings may be combined with the other embodiments to define a desirable irrigation system.

Referring to FIG. 5a, in one embodiment, the interstitial fluid openings 34 are formed by slits in the bending section sleeve 33. The insertion cord comprises the bending section cover, which overlaps the distal segment and is bonded to the distal segment at circumferentially spaced bonding sites with unbonded portions of the bending section cover disposed between the bonding sites. A gap between an unbonded portion of the bending section cover and the distal segment forms the interstitial fluid openings 34, at least when fluid pressure is applied. The slits can be oriented in various orientations. An axial or longitudinal orientation is preferred.

Still referring to FIG. 5a, in another embodiment, the bending section sleeve 33 is bonded to the outer surface 64 at discrete positions 66 and not bonded between the bonding positions 65, which permits pressurized irrigation fluid to discharge through the interstitial fluid openings 35 formed by the unbonded portions of the bending section sleeve 33 overlapping the outer surface 64. The number and sizes of the bonding sites determine the size of the interstitial fluid openings 35 and the pressure required to irrigate. The bonding sites are circumferentially spaced around the circumferential surface, e.g. by gluing or welding. The interstitial fluid openings 34 can also be included.

FIGS. 5b and 5c are cross-sections of the distal tip 13 showing the camera 50 and the LEDs 51 inside the peripheral wall 61 of the tip housing 60. The working channel 41 is also shown. Referring to FIG. 5c, the tip housing 60 may comprise, formed on its circumferential wall 61 and the outer surface 64, one or more grooves 67 extending from a proximal end thereof to a distal end thereof, the grooves extending between bonding positions 65. The grooves 67 may be positioned at places on the tip housing 60 where internal components, such as the working channel, cables, or wires, are not present directly adjacent to the internal surface of the circumferential wall 61 thus allowing space for such grooves. These grooves 67 will act as external irrigation channels for fluid discharged through the respective interstitial fluid openings 35. The cross-sectional shape, and longitudinal shape of the grooves 67 will control the irrigation fluid as it discharges and can be designed to form narrow or wide plumes of fluid in addition to directing an orientation of the plumes/discharged fluid. The grooves 67 may extent in the axial direction or follow a curved or skew path as space allows depending on the position of subjacent components.

The interstitial fluid openings of the preceding embodiments may be closed in a relaxed condition of the bending section sleeve and open when the bending section sleeve is subject to a pressure of irrigation fluid introduced through the proximal end of the insertion cord 10 through the interstitial space 27. The bending section sleeve may comprise a stretchable/resilient material adapted to be stretched by the fluid pressure to open the interstitial fluid openings, which may be referred to as pressure-dependent interstitial fluid openings. The length of the slits and the thickness and tensile strength of the material can be selected for a desired irrigation pressure.

Figures 6A, 6B:
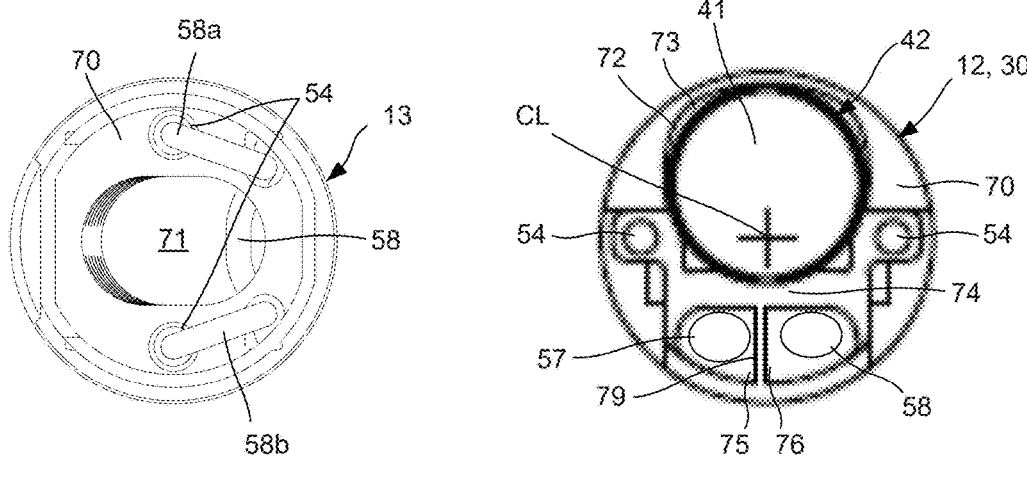
FIGS. 6a-6f are cross-section views of embodiments of bending sections.

The cross-section of the distal tip can have several configurations, some of which are more advantageous for creating larger interstitial space in the distal tip. Referring to FIG. 6a, in one embodiment the distal end segment 30b or the distal tip 13 comprise a wall 70 with a central opening 71. The pull wire 58 is bent in the manner shown in FIG. 6a, through and from one side to the other and back, of the wall 70 through passages 54, to provide a simple way to secure the pull wire 58 to the distal end segment 30b or the distal tip 13. The working channel tube can pass through the central opening 71. The proximal sections 58a, 58b of the pull wire 58 are also shown. The spacing between proximal sections 58a, 58b and the passages 54 and between the working channel tube and the central opening 71 provide interstitial space to the distal tip and the bending section.

FIG. 6b is a cross-sectional view (A-A in FIG. 4a) of an embodiment of the bending section. The longitudinal center axis is indicated by a cross CL. The passage 72 for the working channel tube 42 is also shown. This will often have a circular shape. Passages 54 for the pull wires are also seen. These are often arranged in opposite directions from the longitudinal center axis CL and will extend perpendicularly to a plane traversing the tube 42, referred to as the bending plane when the endoscope bends in one dimension. Hinges 31 are positioned adjacent the bending plane. Two further passages 75 and 76 and exemplary components 77 and 78 are illustrated. These components represent, for example, electrical wires, such as signal cables, or additional tubing for an additional working channel. These two passages are separated by a hinge 79, referred to as a second, or internal, hinge, by contrast with a circumferential, or external, hinge.

In the present embodiment, the passage 72 in the wall 70 accommodates the tube 42. Some space 73 may remain between the circumference of the passage 72 and the tube 42. The space 73 may increase the flexibility of the bending section and also add volume to the interstitial space. The interstitial volume also may include the space between the components 77, 78 and the passages 75, 76 and between the pull wires 58a, 58b and the pull cable passages 54. A wall portion 74 separates the tube 42 and the passages 75, 76.

Figures 6C, 6D:
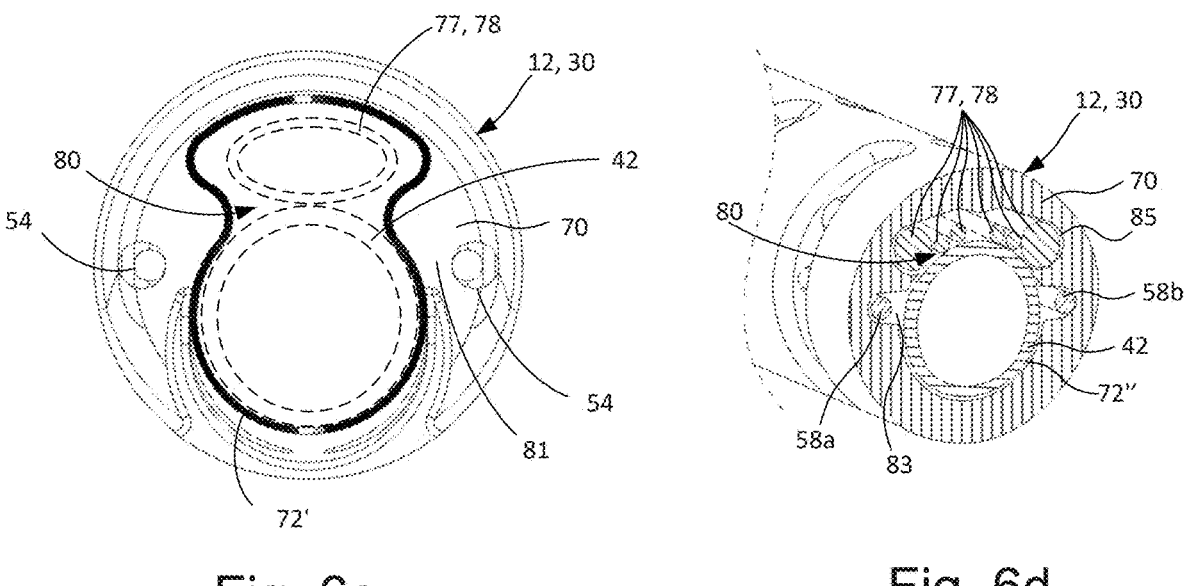

FIG. 6c is a cross-sectional view of another embodiment of the bending section. By contrast with the embodiment described with reference to FIG. 6b, in the present embodiment the wall portion 74 has been removed and the components 77, 78 and the tube 42 pass through a larger passage 72'. Between the components 77, 78 and the tube 42 is additional interstitial space 80. A wall portion 81 separates the pull wire passages 54 from the larger passage 72'.

FIG. 6d is another cross-sectional view of another embodiment of the bending section, which is similar to the embodiment described with reference to FIG. 6c in that the wall portion 74 has been removed and the components 77, 78 and the tube 42 pass through a larger passage 72". Additionally, the wall portion 81 has been removed and therefore the pull wires 58a, 58b also pass through a common passage 72". The removal of wall passages increases the interstitial space. Cut-outs 83 and 85 are also shown and are described below.

Figure 6E:
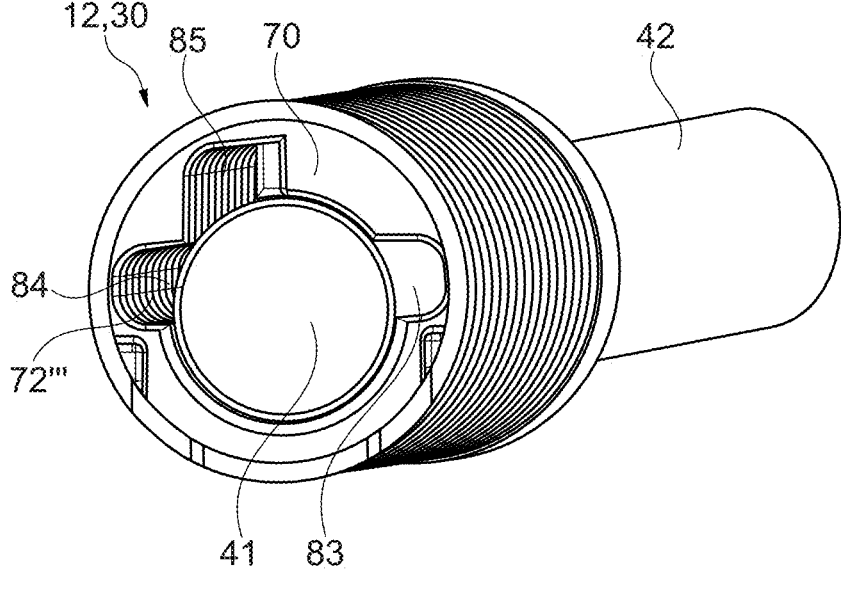
Figure 6F:
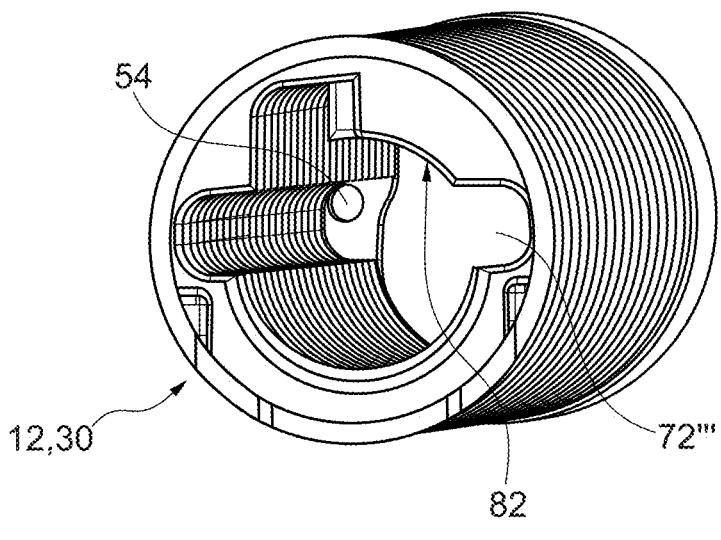

FIGS. 6e and 6f are cross-sectional views of another embodiment of the bending section. In the present embodiment the passage 72" comprises a substantially circular portion 82 for the tube 42 and two or more cut-outs in the wall 70, illustratively cut-outs 83-85, which provide channels through which the components 77, 78 and the pull wires 58a, 58b pass. The bending section thus provides, in a manner similar to the embodiment described with reference to FIG. 6d, structure for the internal components without wall portions that reduce the interstitial space.

Figures 7A, 7B:
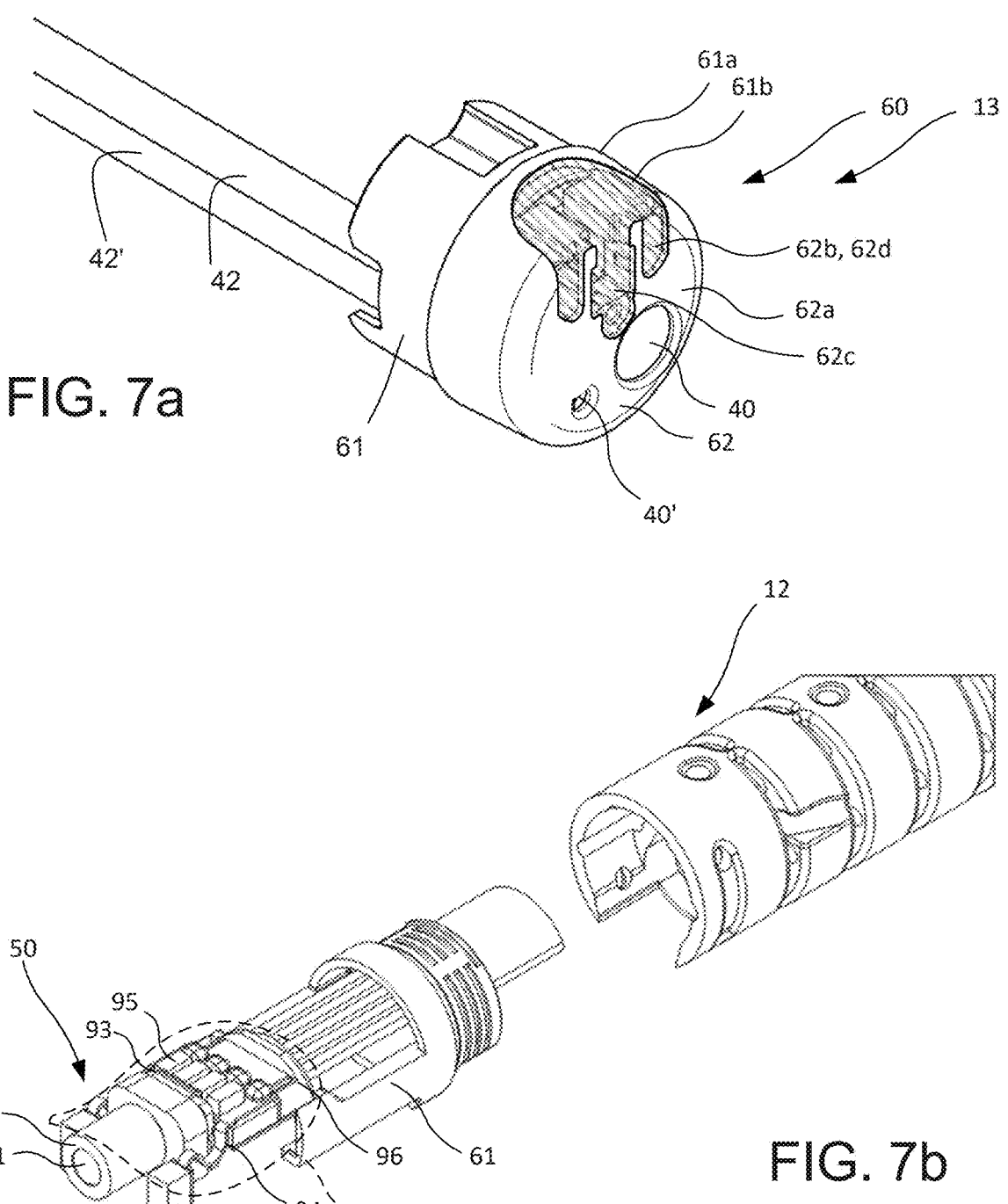
FIGS. 7a and 7b are perspective views of an embodiments of a distal tip.

FIGS. 7a and 7b are perspective views of an embodiment of the distal tip 13. In the present embodiment the distal tip 13 includes the tip housing 60 to be connected to the distal segment 30b and having the circumferential wall 61 and the front wall 62 connected to the wall 61. In some variations the circumferential wall 61 comprises a transparent material. As shown, the circumferential wall 61 has a first portion 61a made of a first material and a second portion 61b made of a second, transparent, material. Portions 61a and 61b can be made in one piece in a two-shot injection molding process. Portions 61a and 61b can also be made in two pieces and bonded together to form a single piece. The front wall 62 has a first portion 62a made of the first material and a second portion 62b made of the second, transparent, material. Portions 62a and 62b can be made in one piece in a two-shot injection molding process. Portions 62a and 62b can also be made in two pieces and bonded together to form a single piece. Portions 61a and 62a are made in one piece and portions 61b and 62b are made in one piece, and all of them can be molded as one piece in the two-shot molding process. The second portion 62b includes a camera window 62c and a light window 62d. As discussed below, the light window 62d can be integrated with a light guide positioned between the LED and the light window, and the combination can be referred to as a light source. Of course light fibers can be used instead of the LED, in which case a light source is used to illuminate the light fibers, as is known in the art. Working channel ports 40 and 40' extending from working channel tubes 42 and 42' are also shown.

FIG. 7b presents a section of the circumferential wall 61 with a portion cut out for illustrative purposes. Within the tip housing 60 is the camera 50 and the LED 51. The camera 50 comprises a camera barrel 90 holding one or more lenses 91 therein and an image sensor 93 axially aligned with the camera barrel and mounted on a circuit board 94 which also may be, optionally, connected to a number of electronic circuits 95. A support frame 96 is provided to facilitate inserting the camera from the proximal end of the tip housing 60 with cables protruding proximally. The camera components may be potted, as illustrated by the dashed line 99, to keep them dry. The interstitial space may extend between the potting material, e.g. epoxy and curable polyolefin polymers, and the circumferential wall 61. Additionally or alternatively, the distal tip irrigation channel portion 38 may be formed in the epoxy to establish fluid communication between the interstitial space and the port 37, for example by potting a wire and then removing it.

Figure 8A:
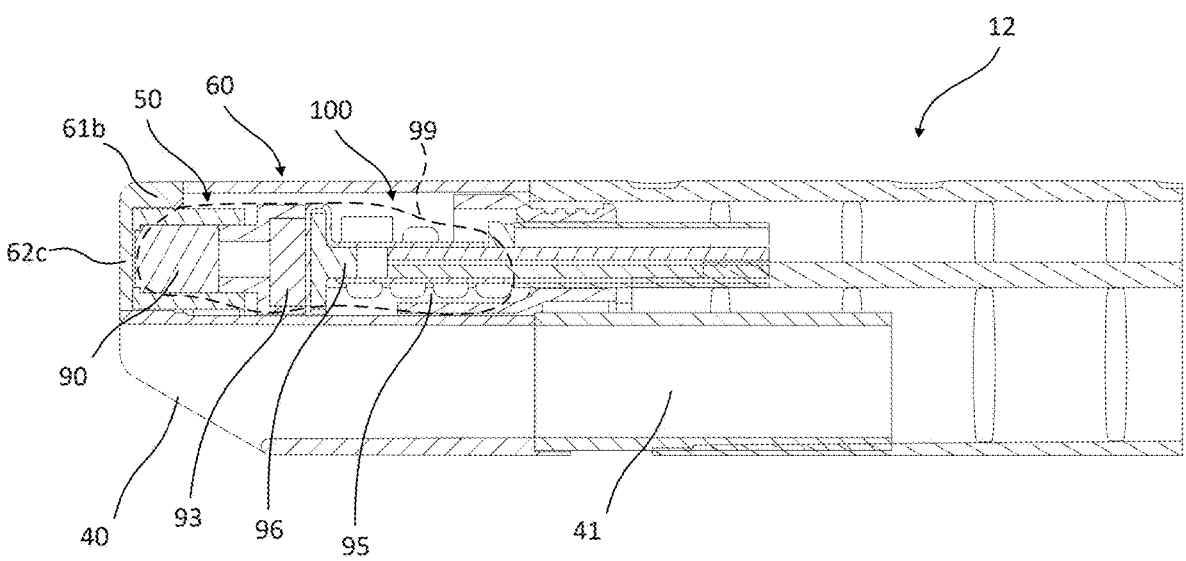
FIG. 8a is a cross-section view of the distal tip of FIGS. 7a and 7b.
Figure 8B:
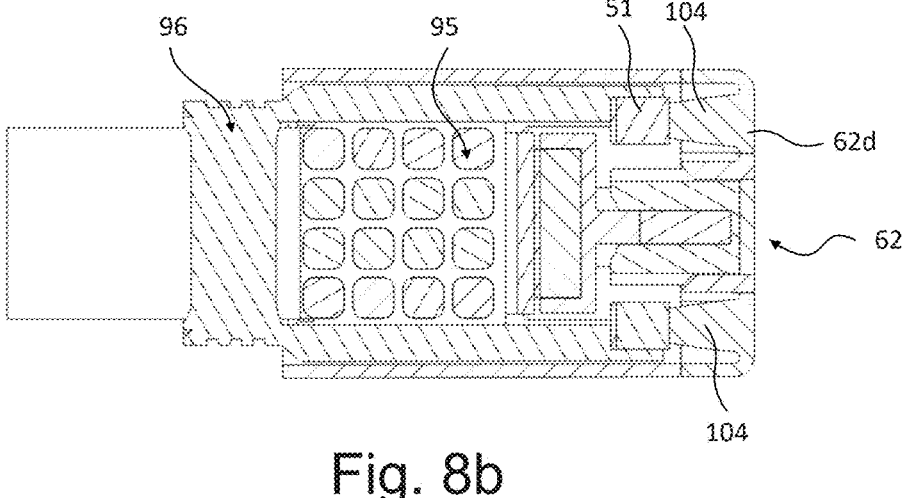
FIG. 8b is a top view of a camera and light guides.

FIGS. 8a and 8b a views of another embodiment of the distal tip 13 which is similar to the embodiment of FIGS. 7a and 7b except for the angled working channel port 40. In the present embodiment the interstitial space created by potting is denoted by numeral 100. Light guides 104 are disposed between the LED 51 and the transparent portion of the front wall 62. In some variations potting does not extend to the light guides 104 to ensure air surrounds them, which improves internal reflection. In some variations cladding is applied to the light guides 104 to improve internal reflection and potting may extend to the cladding, but it does not have too. The light guides 104 can be formed with the transparent portion of the front wall, in one piece, or can be bonded, e.g. adhesively, to a flat front wall. Although not described in detail hereinabove or below, any of the described distal tip embodiments can include light guides as in the present embodiment and variations thereof described herein.

Figure 9A:
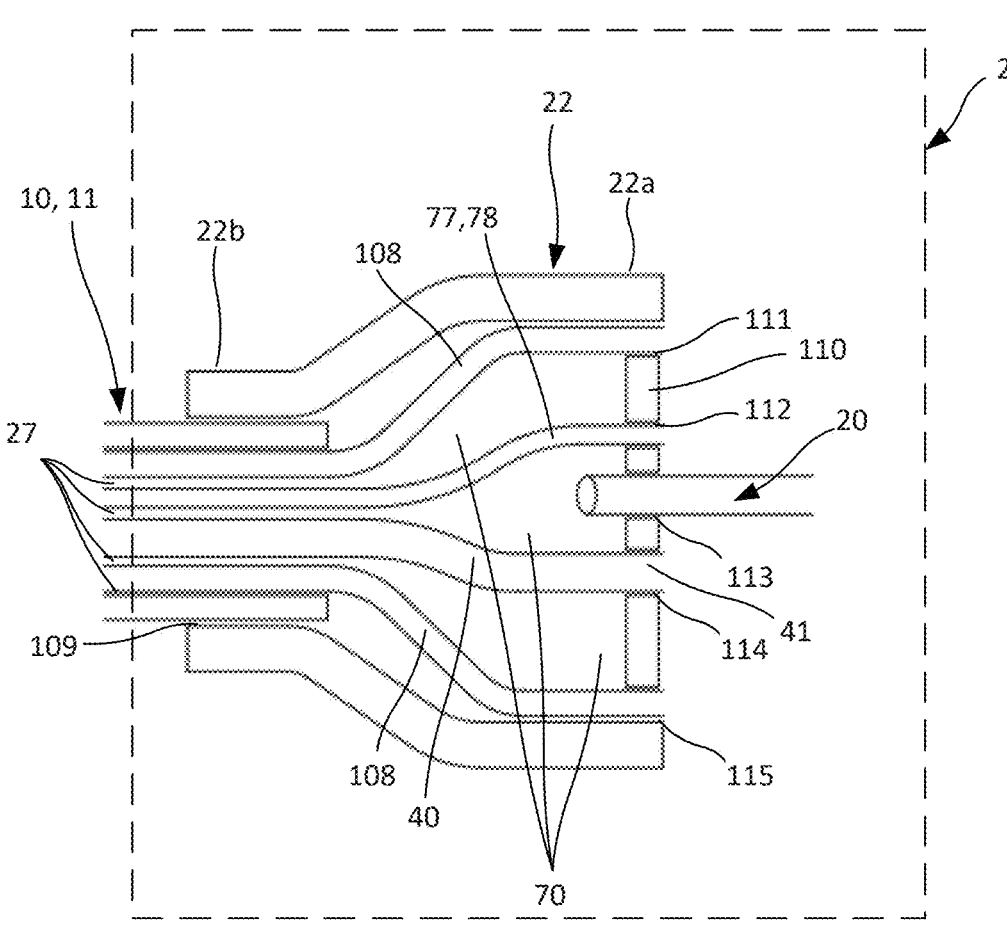
FIGS. 9a and 9b are views of an embodiment of a fluid junction body.
Figure 9B:
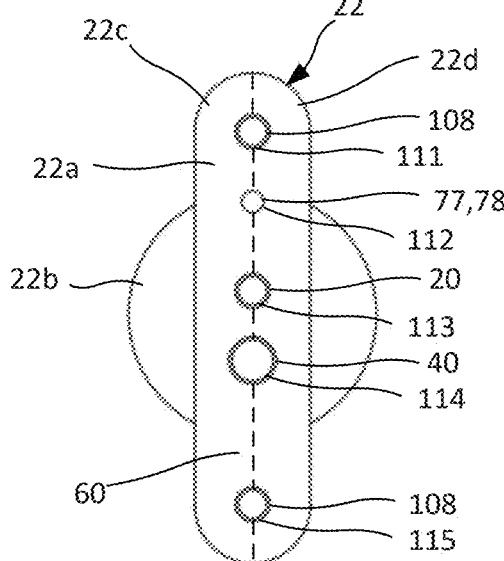

FIG. 9a is a partial longitudinal cross-section of an embodiment of the fluid junction body 22 and FIG. 9b is a proximal view of the same. The fluid junction body 22 comprises a proximal side 22a opposite a distal side 22b. The distal side 22b is sized and shaped to receive the insertion tube 11 and to be fluid sealed therewith. The proximal side 22a is proximal of the distal side 22b and is sized and shaped to receive the irrigation tube 20 and all the components extending from the handle 2, 2' through the insertion tube 11 (referred to as the insertion tube components), and to be fluid sealed therewith. As shown, the insertion tube components include the pull cables 108, the working channel tube 42, and the components 77, 78. The irrigation tube 20 discharges irrigation fluid into the internal space 23 of the fluid junction body 22 and the irrigation fluid then flows, due to fluid pressure, into the interstitial space 27 within the insertion cord 10. Although shown in linear alignment, the proximal side 22a of the fluid junction body 22 does not have to be linearly aligned with the distal side 22b. Furthermore, the insertion tube components do not need to be parallel to each other and can be received by the fluid junction body 22 from any direction.

FIG. 9a also shows a number of passages 109 and 111-115, referred to as the junction body passages, for the insertion tube 11, the irrigation tube 20 and all the components extending from the handle through the insertion tube 11. The junction body passages can be sized to form seals with the respective components received by each passage. For example, the passages can be shaped to receive the component in a press-fit manner. An adhesive or other sealant may be applied to the passage so that after the component/tube is inserted the adhesive/sealant seals the passage. O-rings or tubes of material softer than the irrigation body may be interposed between the passage and the component to form a seal. The passages 111-115 are formed in a wall 110 of the fluid junction body 22, which may comprise two sides formed with each of sides 22c and 22d. Alternatively, the wall 110 can be a plug or grommet that is made separately and inserted into a cavity of the fluid junction body 22.

Referring now to FIG. 9b, in some embodiments the fluid junction body 22 is formed from two parts, 22c and 22d, assembled together. Each part includes an arcuate portion with a surface that is part of the surface of each of the junction body passages. When the two parts are bonded together, the junction body passages are formed by the union of the arcuate surfaces at a seam denoted by a dashed line.

The two parts can be bonded in any known manner, including adhesive and ultrasonic bonding. In alternative embodiments, the fluid junction body 22 is formed in one body and the junction body passages are formed, for example by drilling with a drill or laser. The passages 111-115 may be formed in the wall 110 of the fluid junction body 22, which may comprise two sides formed with each of sides 22c and 22d. A sealant or adhesive can be applied to passages 111-115 to improve or form the seal.

In some embodiments, the fluid junction body 22 is constituted by a single molded body that may be molded in situ around the insertion tube 11, the pull cables 108, the working channel tube 42, and the components 77, 78 to seal them with the fluid junction body 22. Alternatively, the two parts 22c and 22d can be molded in a two-shot injection molding step after placing the pull cables 108, the working channel tube 42, and the components 77, 78.

Figure 10:
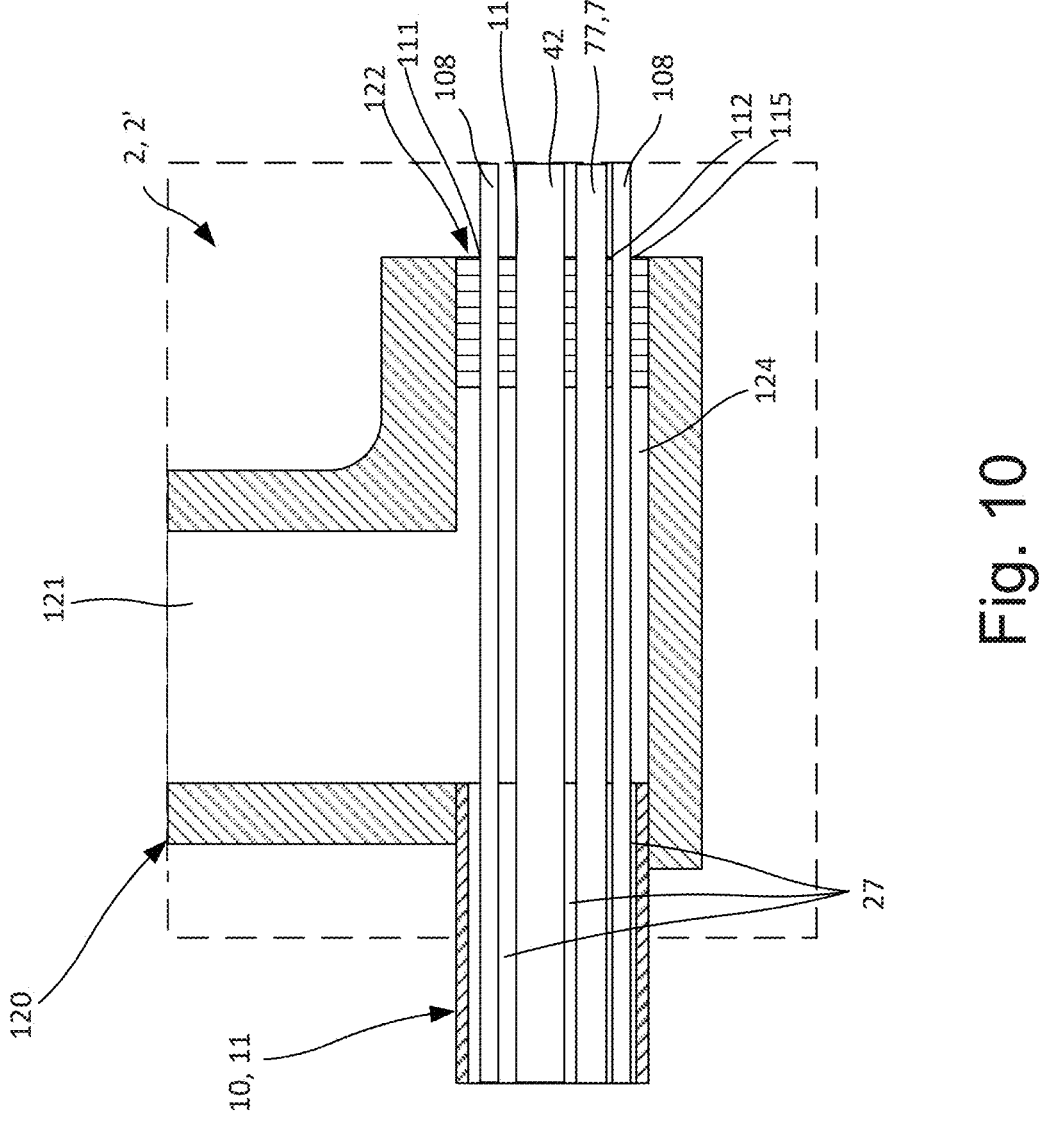
FIG. 10 is a view of another embodiment of a fluid junction body.

FIG. 10 is a partial cross-section view of handle 2, 2', showing another embodiment of the fluid junction body 22. In the present embodiment, the pull cables 108, the working channel tube 42, and the components 77, 78 traverse the fluid junction body 22, in a manner similar to the embodiment depicted in FIGS. 9a and 9b, except that the irrigation fluid is provided via an inlet channel port 120 (described with reference to FIG. 13 with additional detail) defining an inlet passage 121 that is in fluid communication with interstitial space 27 in the insertion cord 10. Inlet channel port 120 can be connected via an irrigation tube, e.g. tube 20, to irrigation inlet port 47, or can form part of the irrigation inlet port 471. A plug, grommet, or wall 122 is provided to seal the proximal ends, located in the handle 2, 2', of the pull cables 108, the working channel tube 42, and the components 77, 78. A sealant or adhesive can be applied to passages 111-115 to improve or form the seal. The present embodiment of the fluid junction body 22 can be formed in two halves that are assembled together, in which case a half of wall 122 can be integrally formed with each half, or can be formed in one piece, which is facilitated by the cylindrical shape of a passage 124 that receives the insertion tube 11 and the plug or grommet 122. An advantage of the present embodiment is that the pull cables 108, the working channel tube 42, and the components 77, 78 typically extend toward the proximal end of the handle 2, 2' while bringing the irrigation fluid at the distal end of the handle 2, 2' minimizes space by reducing the length or avoiding use of the irrigation tube 20. Of course the irrigation tube 20 can also be used to position the irrigation inlet port 47 in a desirable location. The handle-integral irrigation tube 20', with an irrigation channel 21', may also be used to connect the inlet channel port 120 to the source of irrigation fluid.

Figure 11:
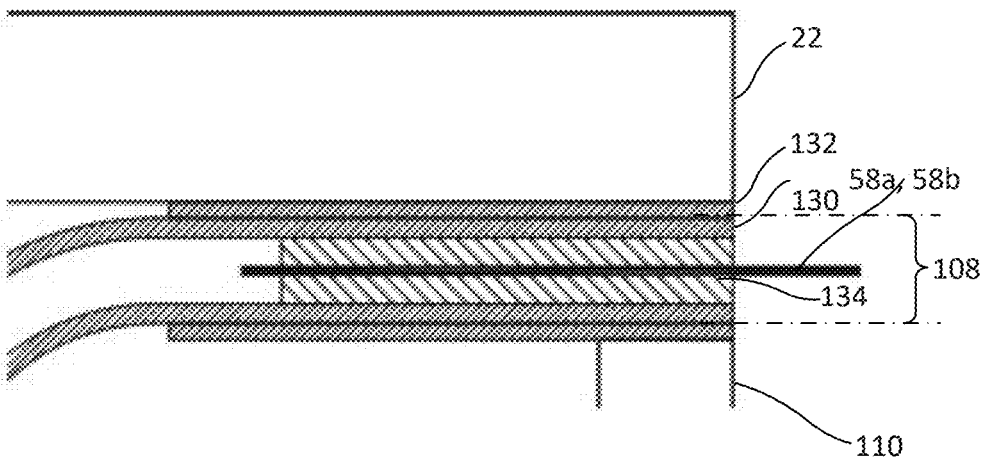
FIG. 11 is a view of another embodiment of a fluid junction body.

FIG. 11 is a partial cross-sectional view of an embodiment of a pull cable 108. Typically the pull cable 108 comprises a pull wire 58a, 58b inside a sheath 130. The sheath can be made of a coil and may include a polymeric coating thereon. As shown, a pipe sealant 132 is provided along a length and on the outer surface of the sheath 130. Another sealant, 134, is applied between the pull wire 58a, 58b and the inner surface of the sheath 130. The sealants may be applied along the sheath for a distance longer than the width of the wall 110 so that sealant extends from one or both sides of the wall 110 proximally, distally, or both proximally and distally. The sealant 134 may be a sealing glue. Slip means, such as oil, may be present between the sealing glue and the pull wire 58a, 58b. The sealant 132 may comprise an adhesive or tube of material softer than fluid junction body 22. Hereby, it is on one hand obtained that irrigation liquid does not leak through the wire pipe when this is provided by a wire pipe made of a wound wire whereby the wire pipe is not water tight and due to the slip means it is, on the other hand, possible for the pull wire to be pulled back and forth in spite of the presence of the sealing glue. In some examples, the pull cable 58 sealing is achieved by the sealing glue 134 penetrating the sheath from the inside thereof, particularly when the sheath is comprised of coiled wire. The sealing glue 134 thus fills spaces between portions of the coil. Of course the pull cable 58 extends proximally from the fluid junction body 22 and the sealant 132 may also extend proximally from the fluid junction body 22.

Figure 12A:
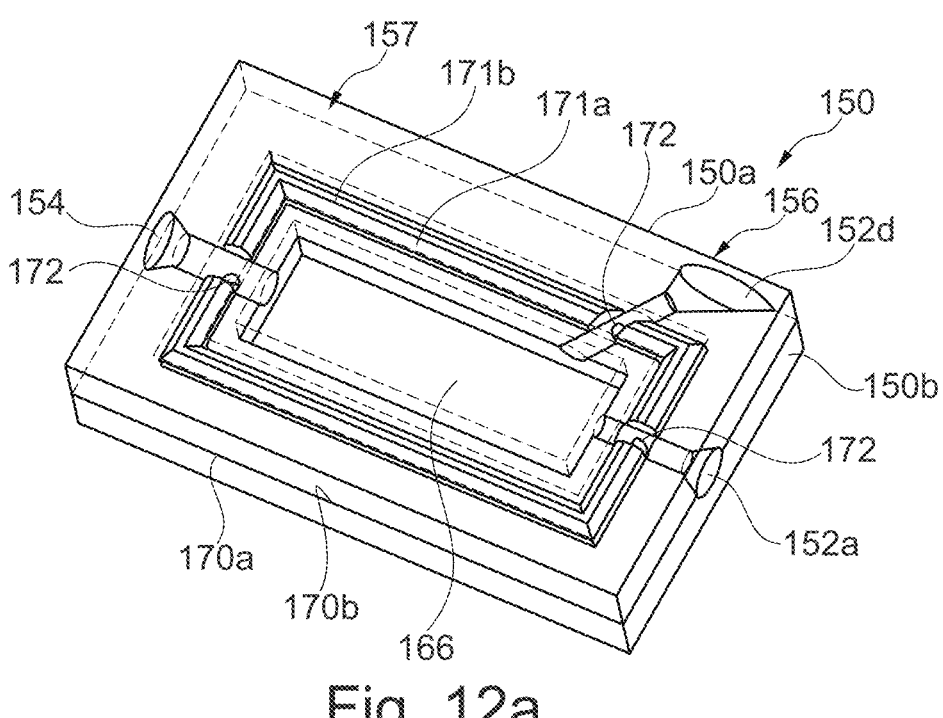
FIGS. 12a and 12b are perspective views of a further embodiment of a fluid junction body.
Figure 12B:
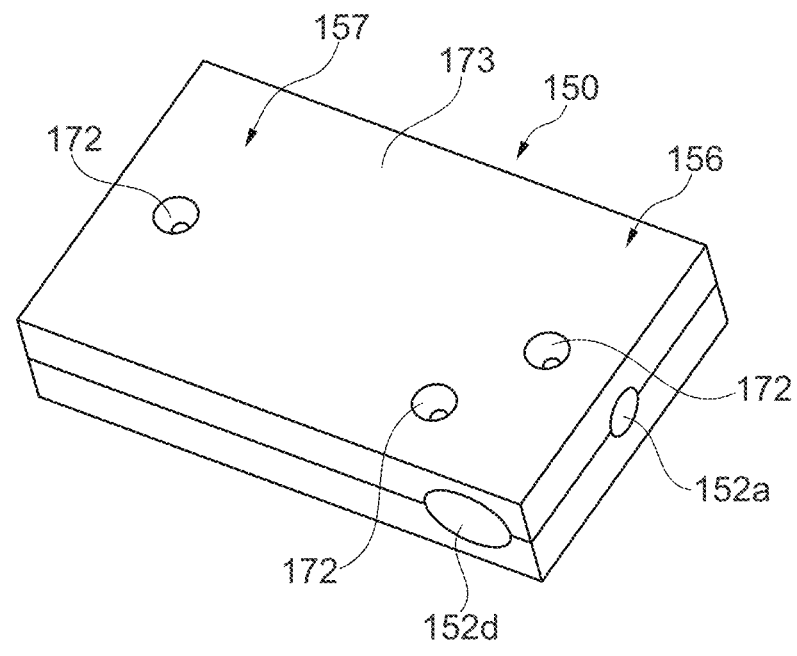

FIGS. 12*a* and 12*b* show another embodiment of a fluid joint body, denoted by numeral 150, comprising a first body part 150*a* and a second body part 150*b*. The first and the second body parts 150*a*, 150*b* are joined to form, for example, first, second, and third passages or channels 152*a*, 152*d*, and 154 provided for insertion of the insertion tube 11, the irrigation tube 20, and a tube 42 providing a working channel. More channels can be provided for pull cables and additional components. For sake of illustration the first body part 150*a* is shown as being transparent and the second body part 150*b* is shown as being opaque. The first and the second body parts 150*a*, 150*b* each comprises an assembly face 170*a*, 170*b* for connection with other of the second and the first body part 150*b*, 150*a*. The assembly faces 170*a*, 170*b* are respectively provided with mutually corresponding valleys 171*a* and ridges 171*b* for securing mutual positioning in the assembled condition when the assembly faces 170*a*, 170*b* are placed in mutual abutment, possibly with a layer of glue in between.

The first and the second body parts 150*a*, 150*b* each comprises a first portion and a second portion and in the assembled condition shown in FIGS. 12*a* and 12*b* the joint first portions and second portions together provides a first sealing body portion 156 and second sealing body portion 157. The first sealing body portion 156 comprises first parts of the first portions of the first and second body part 150*a*, 150*b* and said first parts provide together in the assembled condition of the sealing body, a first channel 152*a* for the at least one of a working channel tube 42, a pull cable 108 or a component 77, 78 to extend into the fluid joint body 150. Thusly, the first parts are intended for extending along at least a part of a circumference of at least one of any pull cable, tube 42, or component 77, 78.

The second sealing body portion 157 is intended for sealing connection towards the insertion tube 11 and comprises a second channel 154 provided by second body parts of the second portions. The second channel 154 provides for the insertion tube 11 to extend into the fluid joint body 150.

The fluid joint body 150 provides for a fluid passage for communicating a fluid with the interstitial space of the insertion cord 10. The first and second body part provide together in the assembled condition of the fluid joint body 150 a third channel 152*d* for the fluid passage to extend into the fluid joint body 150. Such fluid passage may be provided by the irrigation tube 20.

As shown, optionally, the first, second, and third channel 152*a*, 154, 152*d* each comprises an intermediate branch channel 172 extending from an intermediate position in the respective channel to an outer surface 173 of the second body part 150*b*.

In use of the fluid joint body 150 for assembling an endoscope, prior to assembling the first and second body parts 150*a*, 150*b*, glue may be applied to the assembly faces 170*a*, 170*b*, especially to the valleys 171*a* and to the parts to provide the first, second, and third channels 152*a*, 154, 152*d*. The at least one of a working channel tube 42, a pull cable 58 or a component 77, 78, the insertion tube 11, and the irrigation tube 20 may be positioned on the second body part 150*b*. The first body part 150*a* may be assembled with the second body part 150*b* thereby finishing the first, second, and third channels 152*a*, 154, 152*d* with at least one of a working channel tube 42, a pull cable 58 or a component 77, 78, the insertion tube 11, and the irrigation tube 20 positioned and sealed by glue. If the amount of glue provided in the respective first, second, and third channel 152*a*, 154, and 1521*d* are not sufficient to effectively seal between the surface of the respective channel and the elements positioned therein, additional glue may be injected into the channels through the intermediate branch channels 172.

The fluid joint body 150 comprises an inner space 166 defined inside the fluid joint body. The inner space 166 is in fluid connection with the interstitial space of the insertion tube 11 and sealed relative to the internal space 19 of the handle housing 48 (see FIG. 3*b*). The first, second, and third channels 152*a*, 154, 152*d* provide for communication with the inner space 166.

For the glue and/or sealant as described herein a UV setting glue may be used, such as MD® Medical Adhesive 1187-M of the company, DYMAX, but the person skilled in the art will easily realise that many alternatives are useable.

The valleys 171*a* and ridges 171*b* provide a tongue-in-groove joint between the first body part 150*a* and the second body part 150*b*. In alternative embodiments the tonge-in-groove joint is substituted by a half-lap joint. In further alternative embodiments the joint is substituted by using adhesive to secure the first body part 150*a* and the second body part 150*b* to each other.

Hereinabove embodiments of endoscopes, with particular attention to the bending section, distal tip components, and irrigation system were disclosed. Attention is now directed to devices including a laser fiber or shaft.

Significant absorption of irrigation fluid may occur during endoscopic stone surgery and cause hypothermia, pain, and fluid overload. Maintenance of a low intrarenal pressure may decrease the risks of these occurrences. In addition, with increasing use of high-power laser settings for lithotripsy, the potential exists to induce thermal tissue damage. In vitro studies have demonstrated that temperature elevation sufficient to cause thermal tissue damage can occur with certain laser and irrigation settings Clinicians currently address this by using a ureteral access sheath to allow fluid drainage between the sheath and the ureteroscope, as these procedures can be lengthy and prolonged high intra-renal pressures can increase the risk of hemorrhage, infection, sepsis, collecting system perforation, and fluid absorption. Other techniques, including repositioning of kidney stones from the lower pole location into an upper pole location before fragmentation and optionally extraction of the generated fragments, may improve results, as well as provide a stone sample for analysis obviating the need to employ a stone basket.

However, the use of a ureteral access sheath is associated with risk of injury to the ureter, extra costs and time to insert this device, and need for ureteral stent placement after its use, causing significant pain and urinary symptoms for the patient. Furthermore, use of a basket for stone repositioning and retrieval can be difficult and time consuming.

The present disclosure addresses these limitations by providing suction, stone stabilization, and stone removal through a suction channel of a ureteroscope. In some embodiments, provided herein is a ureteroscope comprising a distal end, the distal end comprising: a) a channel configured for delivery of one or more of fluid, suction, or a laser; and b) a further channel comprising a suction port that is configured to remove fluid via suction. In some embodiments, the channels exit the distal end of the ureteroscope on the same or different planes of plane of the distal end of the device (e.g., the plane of the distal end perpendicular to the longitudinal axis of the ureteroscope). The ureteroscope, through the configuration of the channel exits, reduces clogging of the suction port by stones or stone fragments.

Figure 13:
FIGS. 13, 14a, 14b, 15a, 15b, and 15c are views of an embodiment of a device including a laser.

FIG. 13 presents an embodiment of a ureteroscope which is described in more detail with reference to FIGS. 15a-c. Referring to FIG. 13, shown is a section view of an exemplary device comprising an outer housing 200 (similar to outer housing 26) and interstitial flow openings (not shown), the tube 42 for the working channel, a suction port 202, a laser 209, a suction connection 230, and the camera 50. Also shown is one or more fluid ports 120 (see e.g. inlet channel port 120 in FIG. 10). The one or more fluid ports 120 are located at any suitable or convenient location on the device (e.g., the handle or other portion of the proximal (e.g., handle) or distal (e.g., tip) end). In some embodiments, devices comprise one or more fluid ports 120 that are in fluid communication with the working channel tube 42 and/or interstitial space. As shown, a right fluid port 120 is positioned on the handle and another, or left fluid port in the figure, is on the insertion cord. Thus, irrigation fluid may be supplied directly via the insertion cord.

For example, in some embodiments (e.g., the left fluid port 226 shown in FIG. 13) the fluid port 120 is in fluid communication with the interstitial space (not shown in FIG. 13). In some embodiments, the fluid port (e.g., the right fluid port 120 shown in FIG. 13) is in fluid communication with working channel tube 42.

Still referring to FIG. 13, in some embodiments, the internal components are sealed to allow irrigation to flow through the device without damaging any internal components of the device. For example, in some embodiments, the fluid port 120 in fluid communication with the interstitial space comprises a fluid seal 229 between the fluid port 120 and the outer diameter of working channel tube 42. Pull cables 108, components 77, 78, and other components can pass through this seal, as described with reference to FIG. 10. The seal prevents fluid in the interstitial space from flowing into the handle of the device, e.g. endoscope/ureteroscope, and focuses the fluid pressure toward interstitial flow opening(s) 34-37, described with reference to FIGS. 2a, 2b and 5a. Fluid seal 229 can be composed of multiple suitable materials such as, for example but not limited to, conformable elastomeric element(s), adhesive resin, adhesive resin with internal channels and sealant, or other combinations thereof. Some elements passing through fluid seal 229 may not need to translate and thus are glued/sealed into place at fluid seal 229. Other elements passing through fluid seal 229 may need to repeatedly translate proximally and distally with respect to fluid seal 229. In that scenario, it may be preferable to utilize, for example, elastomeric elements and/or a tubing channel with tight tolerance and optionally a sealing lubricant (e.g., medical grade silicone grease), to generate a fluid tight seal that still allows translation of select components about the fluid seal 229. In some embodiments, a fluid port 226 in fluid communication with working channel tube 42 comprises a laser fiber seal 228. In some embodiments, laser fiber seal 228 provides a fluid seal between the laser 209 and the working channel tube 42. This focuses the vacuum pressure at the fluid port 226 to pull fluid through the suction port 202, through the working channel tube 42, and into a fluid collection tank (not shown in FIG. 13). In some embodiments, the laser fiber seal 228 is composed of an elastomeric element and can be selectively loosened or tightened to allow repositioning of the laser 209.

Still referring to FIG. 13, shown is a laser slider 227. In some embodiments, the laser slider 227 is used to optionally linearly translate the laser fiber (e.g., in the plane of the ureteroscope). This can help unclog any stone fragments from the working channel of the tube 42 that may potentially build up and limit the suction flow.

Figure 14A:
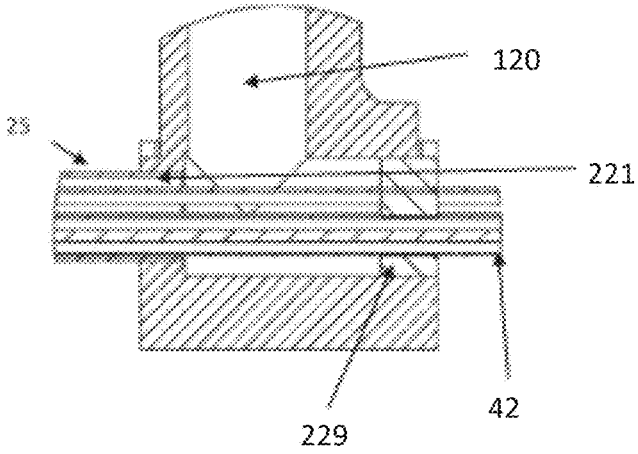

FIG. 14a shows a close-up view of fluid seal 229. Fluid seal 229 fluidly isolates the working channel 41 of tube 42 from the labeled fluid port 120, which is in fluid communication with the interstitial space 221 and is fluidly sealed to the outer housing 225 (e.g. insertion cord 10).

Figure 14B:
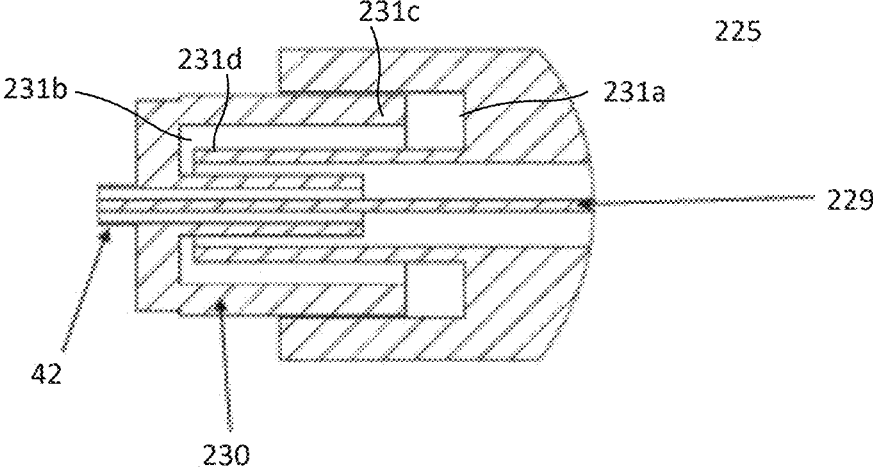

FIG. 14b shows a close-up view of the suction connection 230. The suction connection 230 fluidly connects the working channel 41 of the tube 42 (comprising the laser fiber 209) to a fluid port 120 (not shown in FIG. 14b). The suction connection 230 isolates the working channel tube 42 from the interstitial space 221. As shown, the suction connection 230 comprises dual cylindrical tongue-in-groove joints, comprising grooves 231a,b and tongues 231c,d.

Figure 15A:
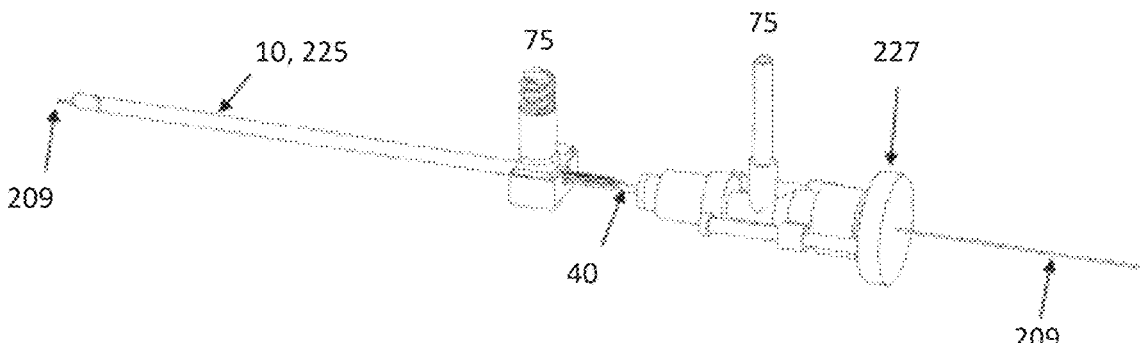
Figure 15B:
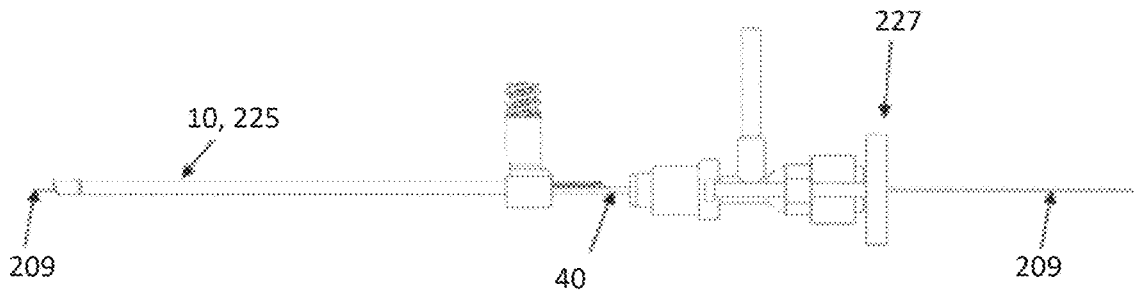
Figure 15C:
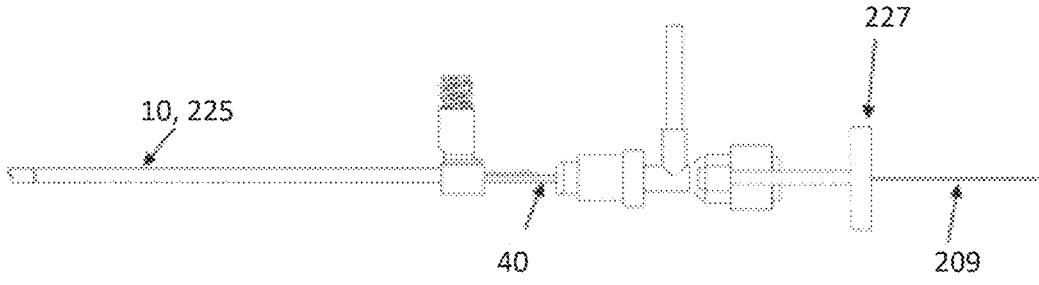

Now referring to FIGS. 15a-c, shown is an embodiment of the device of FIGS. 13-14b comprising the laser slider 227. However, the laser slider 227 can be integrated into any number of devices described herein. FIGS. 15a and 15b show the laser slider 227 in normal configuration (e.g., not in use). It is pushed forward (distally) and the tip of the laser 209 extends beyond the distal tip of the device so it can ablate kidney stones, for example. In FIG. 15c, the laser slider 227 is actuated to translate the laser fiber 209 proximally, toward the device's handle. The laser slider 227 can then be returned to its original position to move the laser fiber 209 back into proper position for kidney stone ablation. In some embodiments, the actuation is repeated one or more times in order to dislodge any stones in working channel tube 42.

The endoscopes and devices described herein are used in combination with laser lithotripsy systems. Lasing may be performed with a pulsed Ho:YAG laser coupled to a fiber optic that can be passed through the working channel, although other systems such as a TFL system are specifically contemplated.

The distal tips described previously, including the camera 50, the LED 51, the light guides 104, the various embodiments of bending sections and tip housings, etc., are suitable for use with the devices described below. FIGS. 16a-31 describe features suitable for the treatment of kidney stones and, more generally, for treatments in which irrigation and object control may be required.

Figure 16B:
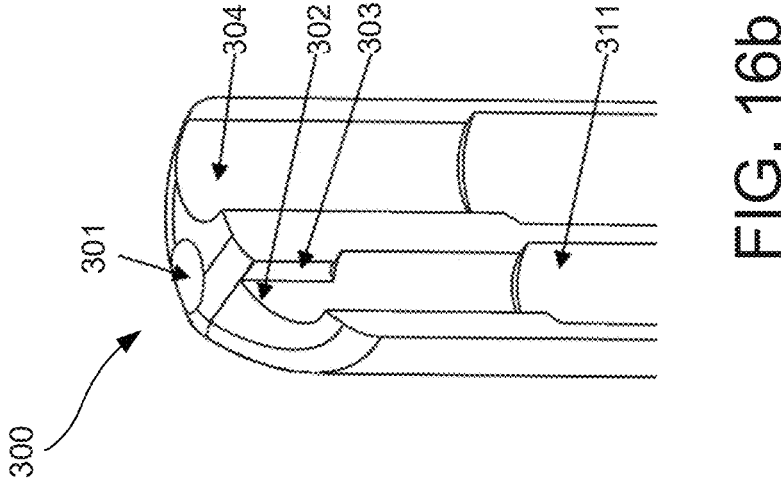
FIGS. 16a-16d show alternative embodiments of distal tips of devices of the present disclosure.
Figure 16A:
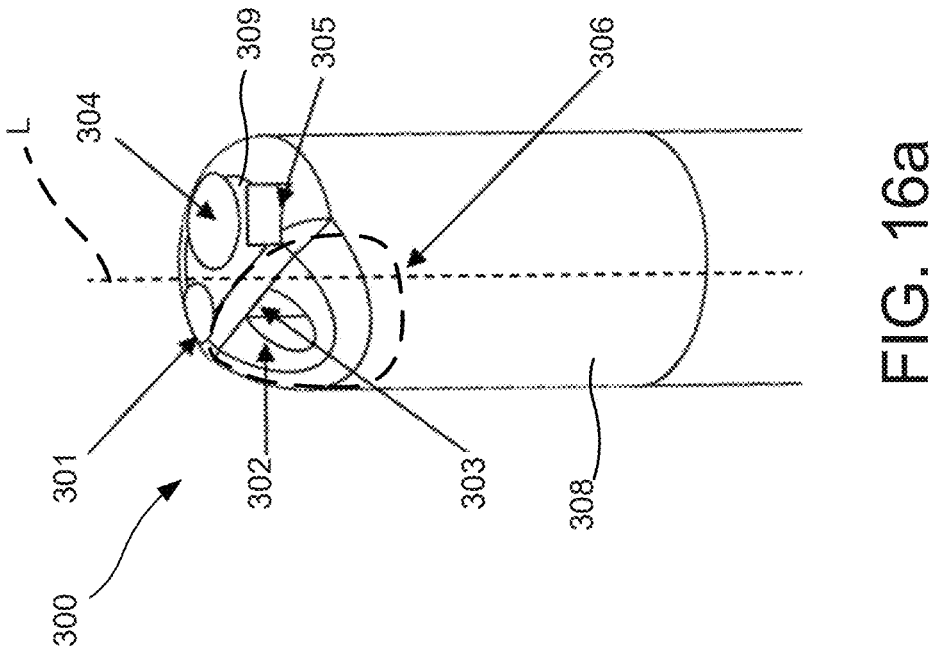
Figures 16C, 16D:
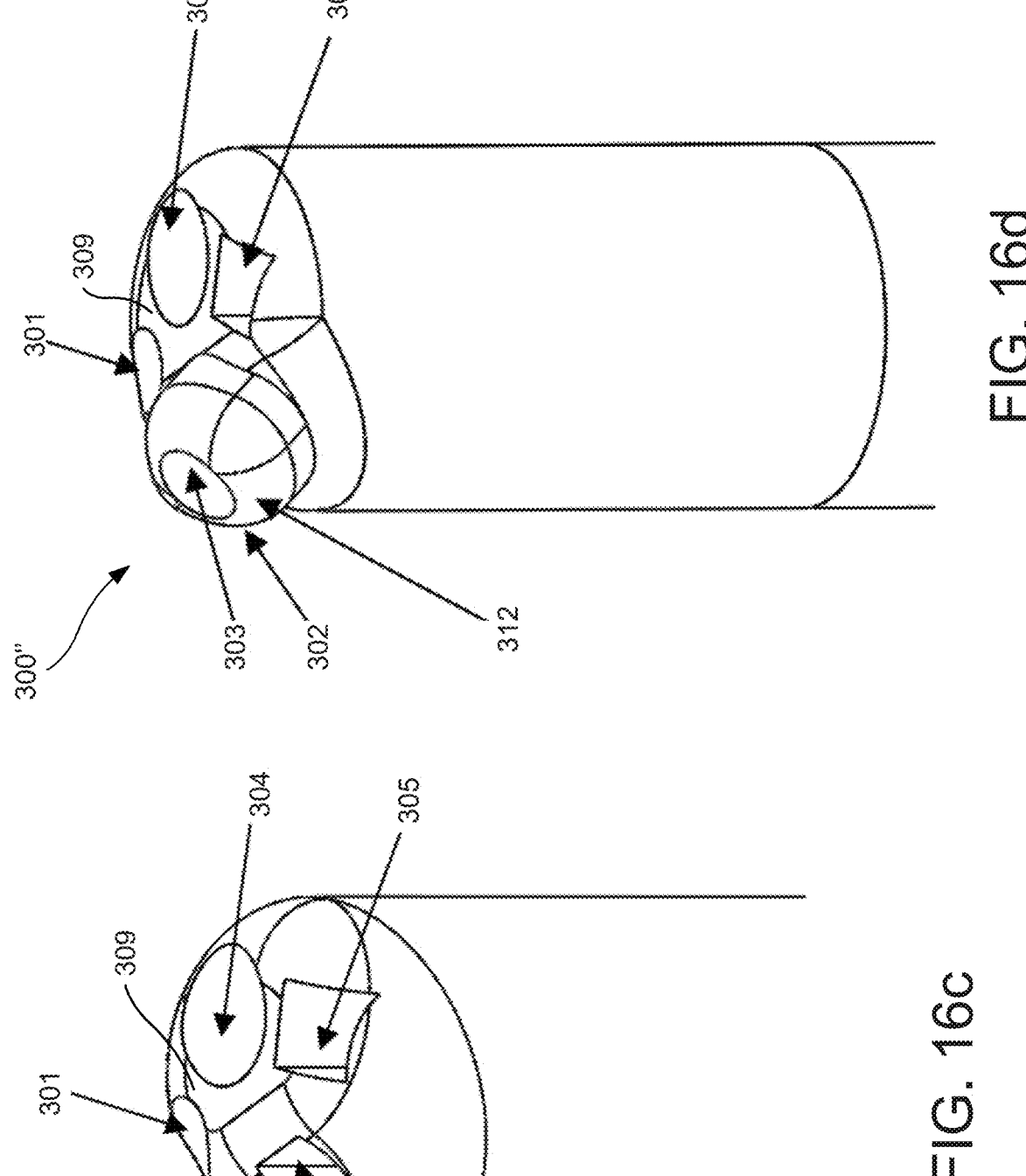

FIGS. 16a-c are perspective and partially sectioned perspective views of embodiments of distal tips in which the camera is positioned above the surface of the suction port and the suction port is angled such that if an object, e.g. tissue or a stone, attaches to the suction port there is a reduced risk of vision impairment. In this context, the camera includes the camera window. Camera windows were described with reference to FIG. 7a although cameras that incorporate a window or a lens that functions as a window can also be used. Referring to FIGS. 16a and 16b, a distal tip 300 comprises a light 301, a suction port 302, an anti-clog inlet or feature 303, a working (e.g., laser and/or irrigation) channel port 304 of a working channel tube (e.g. 42), a camera 305, and a region 306, which optionally may be made of compliant material. The dashed line represents the longitudinal axis of the ureteroscope. The working channel port 304 is presented in a plane perpendicular to the longitudinal axis of the device and the suction port 302 is presented on a different plane that the working channel port 304, for example at a 20 to 70 degree angle relative to the plane of the working channel port 304 (although the invention is not limited to these particular dimensional relationships). The light 301, the suction port 302, the working channel port 304, and the camera 305 can be the same as the light 51 (including the LED, light window and possible a light guide), the component 77/78, the working channel tube 42, and the camera 50 in the embodiments described with reference to FIG. 4a, 5b, 7a-8b. Similarly, the light 51, the component 77/78, the working channel tube 42, and the camera 50 can be the same as the light 301, the suction port 302, the working channel port 304, and the camera 305. Transparent windows 301', 305' may be provided distally and in longitudinal alignment of and with the light 301 and the camera 305, respectively, as is known in the art and discussed hereinabove. The windows 301', 305' may lie on the same plane as the working channel port 304 and be part of the front wall 309. Alternatively, the light 301 and the camera 305 may each comprise a window.

In some embodiments, the camera 305 provides a real-time view of the working area to the operator of the device, displayed on a user interface that may be connected by wire or wirelessly to the camera, as described with reference to FIGS. 1a and 1b. In some embodiments, the camera is a video camera. The present disclosure is not limited to particular camera technologies. In some variations of the present embodiment, the light and the camera occupy a common lumen or passage in the distal tip. In some variations of the present embodiment, the distal tip incudes two lights, which may occupy a common passage in the distal tip or be positioned in different passages.

The distal tip 300 also comprises a circumferential wall 308 and a front or distal wall 309. The circumferential and front walls can be made of the same material in an injection molding process. A transparent window can be placed in front of the camera and the light, as is known in the art. The transparent window can be molded with the material of the circumferential and front walls in a two-shot injection molding process. The region 306 may be made of compliant material. Compliant material may be a material softer than the material of the circumferential wall. The region 306 may be as an insert or plug affixed, mechanically, chemically, physically, or a combination thereof, to the circumferential wall and/or the front wall. An example of a compliant material is an elastomeric polymer. The compliant material is selected to allows region 306 to conform to the shape of a kidney stone when a stone contacts region 306 due to suction. The circumferential wall and the front wall may be made of a non-compliant, e.g. rigid, polymer.

Placing the suction port 302 on a different plane from the camera 305 prevents the camera image from becoming blocked by objects, e.g. tissue, a stone or stone fragments, during fluid suction through the suction channel. As the objects collect in front of the suction channel, they will tend to angle away from the camera field of view, which may be aligned with the longitudinal axis of the device, helping to mitigate the full camera obstruction so the clinician can continue to see where the distal tip is positioned, e.g. in the kidney. In the device shown in FIG. 16a the face of the front wall 309, surrounding the suction port, is flat. The light 301 illuminates the working area in front of the distal tip. The peripheral edges of the distal tip are preferably rounded and smooth to make insertion, e.g. into the ureter, easier.

The anti-clog inlet 303 (described in more detail below) prevents clogging of the suction port and/or suction channel by large objects, e.g. stones or stone fragments, which may be larger than the suction port.

The working channel port 304 provides a port for a shaft/fiber of a laser and/or fluid delivery. In some embodiments, the working channel port 304 (and the working channel) is able to accommodate both the laser shaft/fiber and a fluid delivery component (e.g., during ablation).

The distal ends of the suction and working channels may be referred as ports or openings. In some embodiments, the diameter of the suction channel and/or working channel is narrower near the distal opening, as shown in FIG. 16b. As shown, a portion of the suction channel, denoted by numeral 311, has a larger cross-section (or diameter, if the channel is circular) than the respective port (orthogonally to the longitudinal axis). This first narrowing at the distal tip can assist with device assembly, providing a rim/hard stop for tubing used to provide the channels. The narrower cross-section of the ports can match the inner diameter of the tubing forming at least portions of the channeless. In some embodiments, the tubing has metallic braiding (e.g., stainless steel or nitinol) in the wall to prevent distal channel kinking during articulation. An additional narrowing, such as seen with anti-clog inlet 303, can be utilized to prevent stone fragments of a certain size from entering the suction channel. This can act to reduce the chances for clogging of the suction channel with object fragments, during the procedure. In other embodiments, channel diameters are constant throughout the device.

FIG. 16c shows an exemplary distal tip 300' similar to distal tip 300 but with a rounded, convex face surrounding the suction port 302 rather than a flat face as shown in FIG. 16a. The working channel 304 on the rounded surface is presented on a plane substantially perpendicular to the longitudinal axis with the suction port 302 residing on a different plane.

FIG. 16d shows an exemplary distal tip 300" similar to the distal tip 300 but with the suction port presented on a protrusion 312 comprising the suction port 302 and the anti-clog inlet 303. The protrusion 312 extends distally from the front wall 309, isolating the suction port from the camera to reduce the risk of an object obstructing the view of the camera, for example due to the object being sucked into the suction port during suction. The protrusion 312 may comprise a shaft section extending from the circumferential wall and may be constructed of the compliant material discussed previously. The protrusion 312 may be of any shape or length that accommodates the suction port and the inlet 303. The shaft section may be angled relative to the longitudinal axis and the suction port 302 may be on a non-orthogonal plane relative to the longitudinal axis.

Figure 17B:
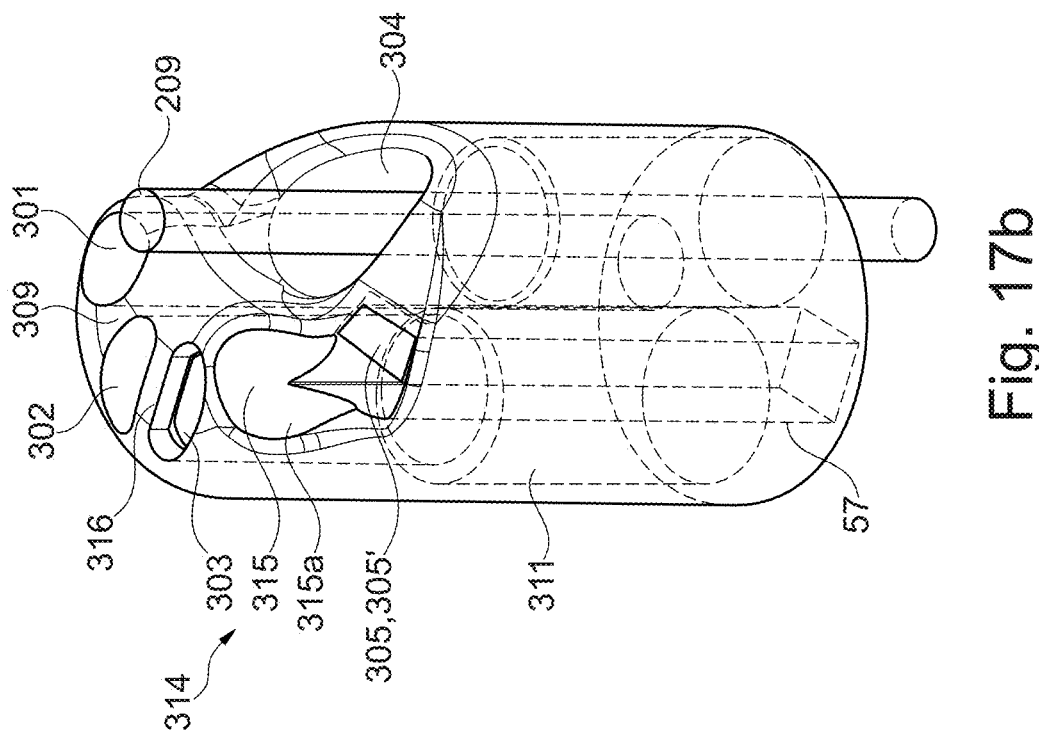
FIGS. 17a and 17b show another embodiment of a distal tip of devices of the present disclosure.
Figure 17A:
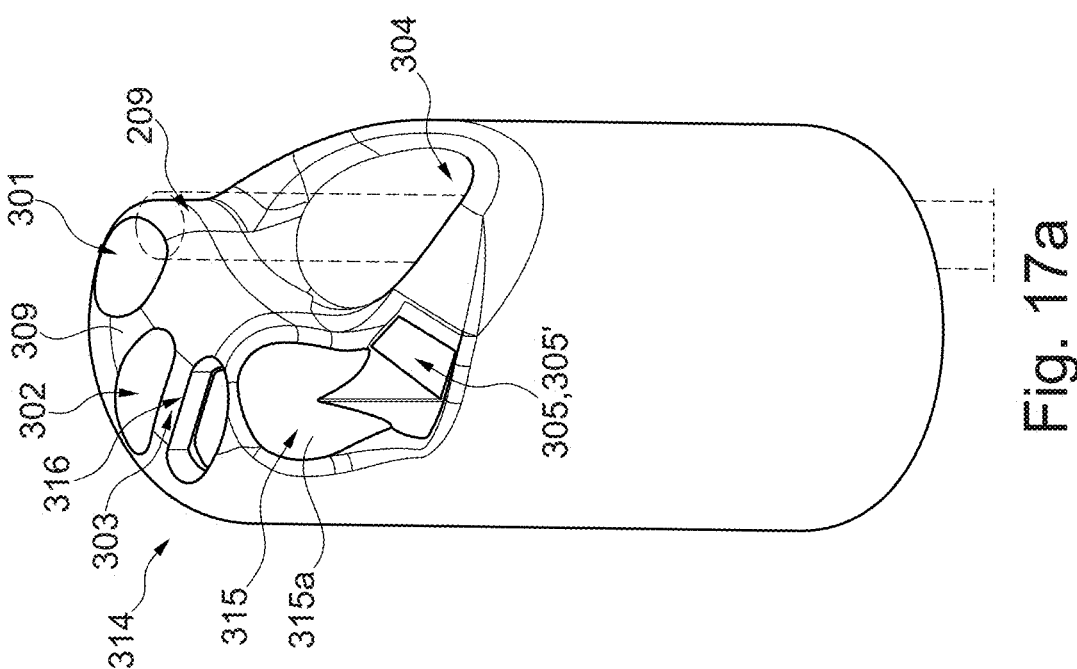

Now referring to FIGS. 17a and 17b, another embodiment of a distal tip, denoted by numeral 314, similar to the distal tip 300, comprises a cut-out region 315 comprising a longitudinal surface 315a extending proximally from the front wall 309 to a distal end of a passage for the camera cables, e.g. passage 77. The camera 305 is positioned below the suction port 302 at a proximal end of the cut-out region 315. FIG. 17b is a transparent view of the embodiment shown in FIG. 17a. Positioning the camera proximally of the suction port allows the user to see when an object, e.g. stone, is engaged with the suction port. The camera cut-out region 315 is shown as a notch in the distal tip, which comprises the longitudinal surface 315a extending proximally from the front wall 309 to the distal end of the passage for the camera cables. The camera 305 is shown placed at the bottom of the cut-out region 315 proximally of suction port 302. The suction port 302 and the anti-clog inlet 303 are shown as separate openings, separated by a bar 316, that lead to suction channel 311, and both the suction port 302 and the anti-clog inlet 303 are in fluid communication with the suction channel 311. The working channel port 304, shown with the laser shaft/fiber 209, is on a different plane than the suction port 302, proximal of suction port 302. As shown, the suction port 302 is on a plane substantially perpendicular to the longitudinal axis of the device and the working channel is in a non-perpendicular plane. In other embodiments (not shown in FIG. 17*a*), the working channel is on a perpendicular plane and on a different, proximally located, plane than the suction port.

Figure 18:
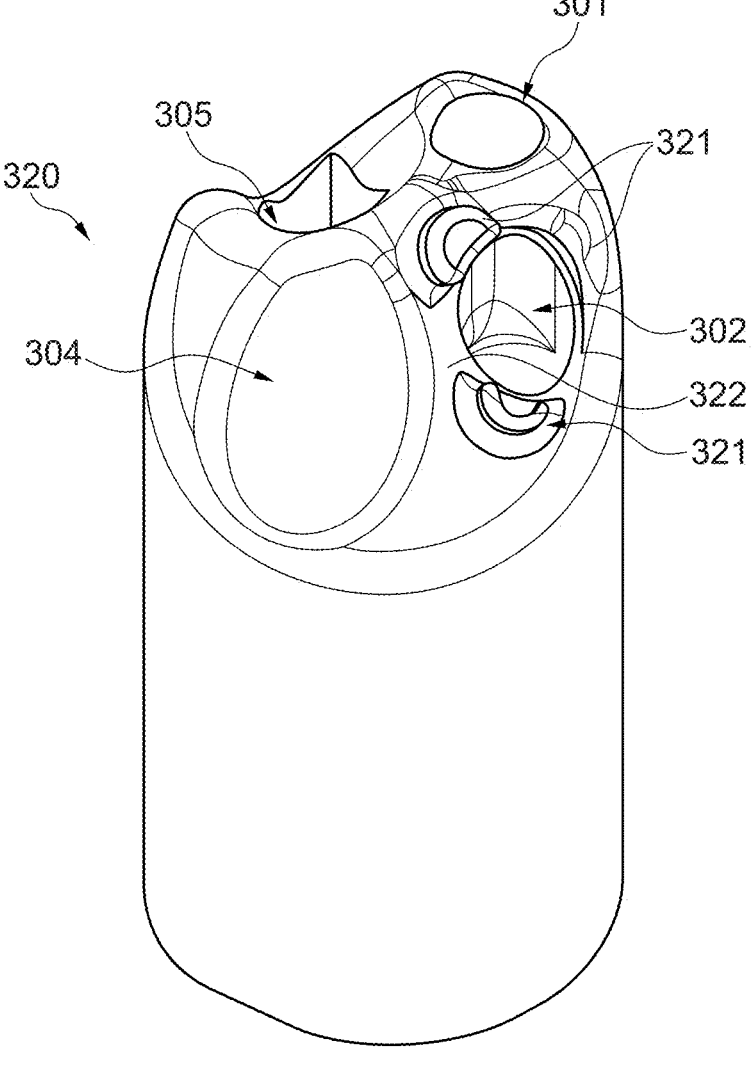
FIG. 18 shows another embodiment of a distal tip of devices of the present disclosure.

Referring now to FIG. 18, yet another embodiment of a distal tip, denoted by numeral 320, provides an anti-clog feature comprising protrusions or depressions 321 surrounding a peripheral surface adjacent to the suction port 302. The anti-clog feature prevents occlusion of the suction port by objects, e.g. kidney stone or fragment thereof, that might otherwise be sucked into the suction port 302. The protrusions 321, which may comprise 1, 2, 3, or more protrusions, define ridges 322 between them. When an object is sucked into contact with the protrusions fluids can still be sucked between the protrusions over the ridges into the suction channel. In the same manner the depressions allow portions between them, of the peripheral surface of the suction port 302, to hold the object while fluid flows between the object holding portions, over the depressions and into the suction channel. The present disclosure is not limited to a particular shape or configuration of the protrusions/depressions.

Figures 19A, 19B:
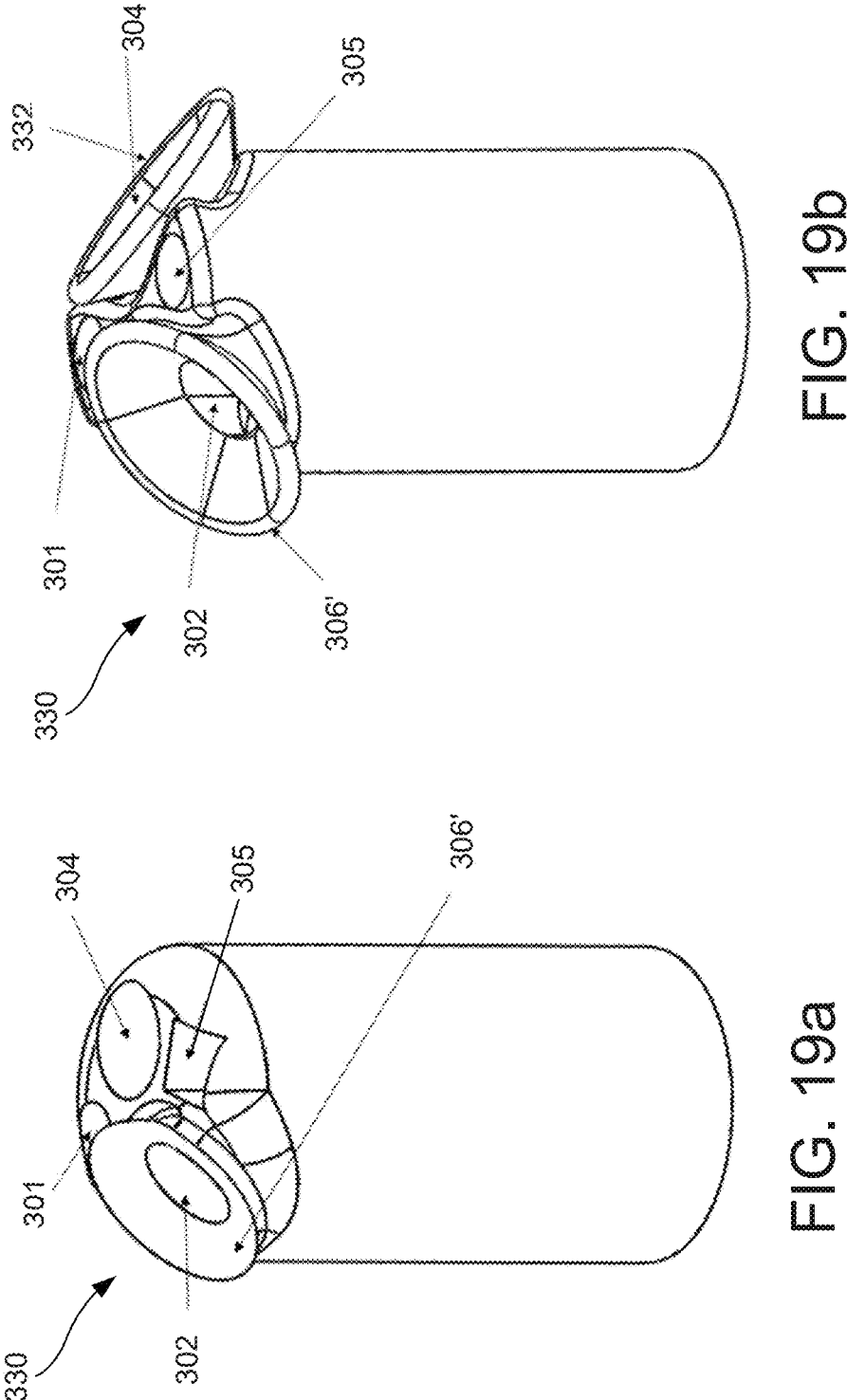
FIGS. 19a and 19b alternative embodiments of distal tips of devices of the present disclosure.

Now referring to FIGS. 19*a* and 19*b*, in another embodiment of a distal tip, denoted by numerals 330 and 330' respectively, a compliant region 306' extending distally from the suction port 302, illustratively a suction cup, surrounds the suction port 302. The suction cup is sized and structured to conform to objects, which may be irregularly shaped kidney stones, so they can be secured. The objects can then be moved to a desired location in the kidney, for example by movement and articulation of the bending section. The composition and securement of the compliant region 306' is as described with reference to the compliant region 306 in FIG. 16*a*. Of course the suction cup, having a thin peripheral wall around the suction port 302, can be structured to provide an even more compliant component, for example by selection of the wall thickness, angle relative to the plane on which the suction port 302 lies, and wall depth (measured radially outwardly from the suction port 302). As previously discussed, the plane on which the suction port 302 lies is different and can be at an angle, greater than zero, relative to a plane on which the working channel port 304 lies. The light 301 and the camera 305 are on the same plane as the working channel port 304.

The distal tip 330', shown in FIG. 19*b*, also includes a compliant region 332, e.g. a suction cup, surrounding the working channel port 304. In some embodiments the suction channel can be sized and shaped to function as a working channel, and the two working channels can be used interchangeably. In such embodiments the working channel ports 302, 304 can be symmetrical relative to the bending plane and each comprises a suction cup shaped compliant region. As shown in FIG. 19*b*, the ports lie on different but symmetrical planes which are not perpendicular to the longitudinal axis of the device. The light 301 and camera the 305 are on a different plane than the ports and distal therefrom.

Figure 20B:
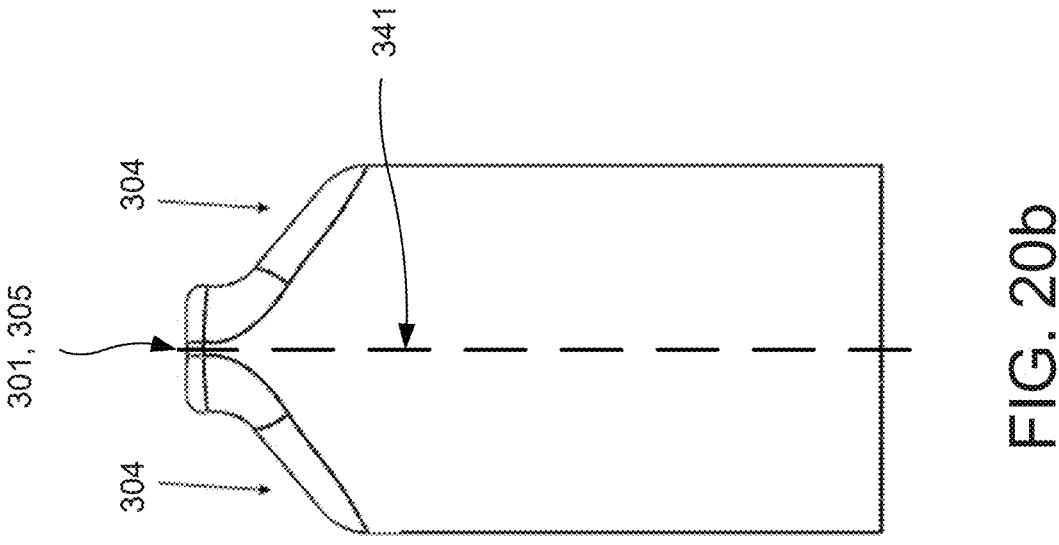
FIGS. 20a and 20b show another embodiment of a distal tip of devices of the present disclosure.
Figure 20A:
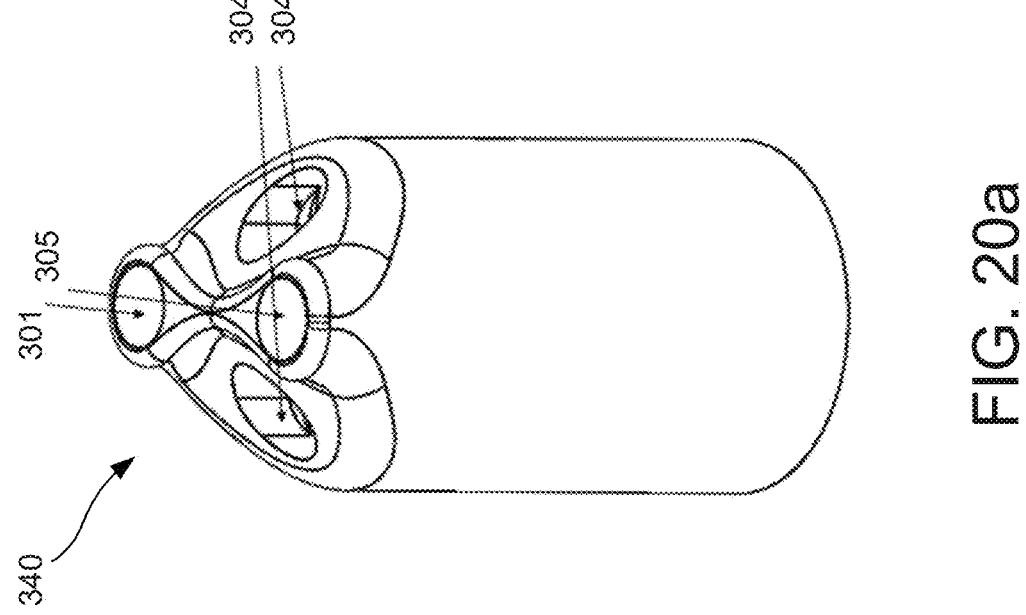

Now referring to FIGS. 20*a* and 20*b*, in a further embodiment of a distal tip, denoted by numeral 340, symmetrical working channels and ports 304 are provided. FIG. 20*b* shows a side view of the device of FIG. 20*a*. One of the working channels can be used as a suction channel. The light 301 and the camera 305 are positioned opposite each other along a symmetry plane depicted as a line 341. The working channels are in different, symmetrical planes on opposite sides of the device. The working channel ports 304 are in planes that are not perpendicular to the longitudinal axis of the device. The side view illustrates that the light 301 and the camera 305 are on a plane perpendicular to the longitudinal axis of the device.

Figure 21:
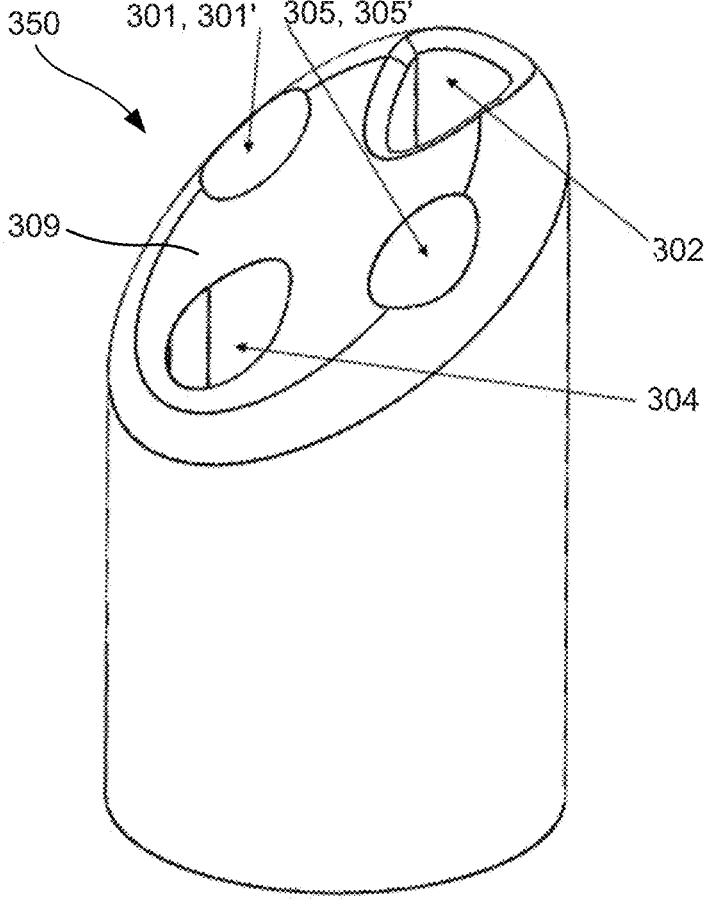
FIG. 21 shows another embodiment of a distal tip of devices of the present disclosure.

FIG. 21 is a perspective view of another embodiment of a distal tip, denoted by numeral 350. The suction port 302 and the working channel port 304 are provided on a common plane that is not perpendicular to the longitudinal axis of the device. The light 301 and the camera 305 are positioned on either side of a plane traversing the suction port 302 and the working channel port 304. In some embodiments, the window light 301', the suction port 302, the working channel 304, and the camera window 305' lie on the same plane. In some embodiments, the top edge of the camera 305 protrudes from the plane and thus is on a plane parallel to and distal of the plane on which the suction port 302 and the working channel 304 lie. In some embodiments, the location of the suction port 302 and the working channel 304 are switched.

Figures 22A, 22B, 22C:
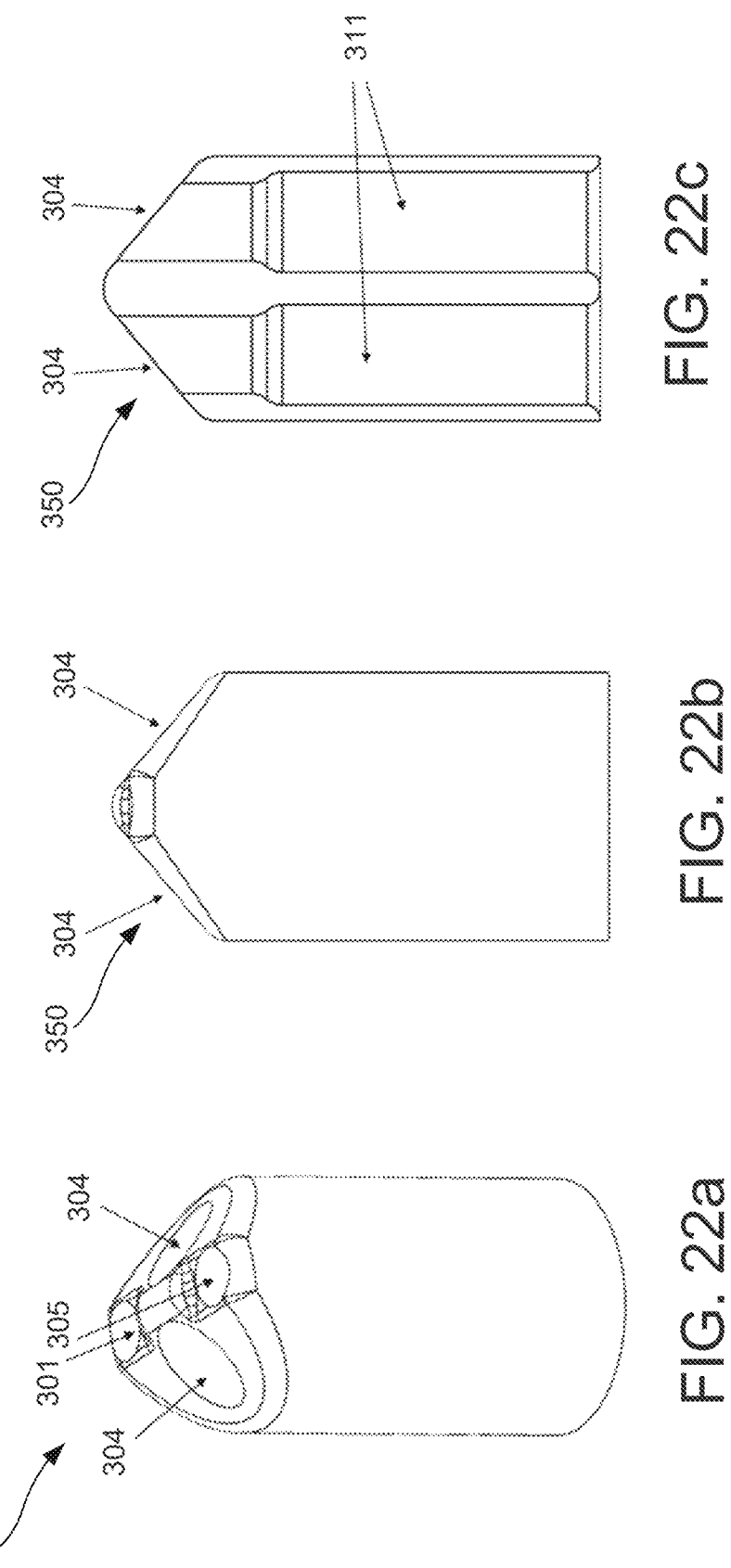
FIGS. 22a, 22b and 22c show another embodiment of a distal tip of devices of the present disclosure.

Now referring to FIGS. 22*a-c*, shown is an alternative embodiment of a device with a distal tip 350 where the working channel ports 304 are each substantially in a plane or are substantially planar. As used herein, the term "substantially in a plane" or "substantially in the plane" in reference to an opening or exit of a channel or port of a device described herein refers to an opening or exit that is at least 90% (e.g., at least 90%, 91%, 92%, 93%, 94%, 95%, 96%, 97%, 98%, 99% or 100%) in a single plane (or substantial plane). For example, as shown in FIG. 22*a*, each of the working channel ports 304 is substantially in a single plane because the entire circumference of the working channel port 304 is in the same plane. This is further illustrated in the side view shown in FIG. 20*b* and the cut-out view of FIG. 22*c*, where the entire port or opening of the working channel is in the same plane. The working channels are symmetrical and thus can serve interchangeably as channels for laser/irrigation or suction. As discussed with reference to FIG. 16*b*, the working channels 311 narrow near the working channel ports 304.

As used herein, the term "substantially planar" when used in reference to an opening or port of a channel refers to an opening or port that is at least 90% (e.g., at least 90%, 91%, 92%, 93%, 94%, 95%, 96%, 97%, 98%, 99% or 100%) planar. For example, the ports of the working channels shown in FIGS. 22*a-c* are substantially planar (e.g., substantially in the same plane across the entire opening). This definition tolerates some curvature of the opening around a plane (e.g., a curvature that follows the shape of a curved surface of the device).

Not all openings on the single device need to be in the same plane or a plane with the same angle relative to the longitudinal or perpendicular axis of the device in order to be individually substantially in a plane or planar. For example, in the device shown in FIG. 22*a*, each of the planes that the two working channels exit the device on could be at a different angle relative to the longitudinal or perpendicular axis of the device.

Now referring to FIG. 23*a-h*, shown is an alternative embodiment of a device with a distal tip 360, where the camera 305 or camera window 305' is on a plane above, or distal from, the working channel ports 304, and the working channel ports 304 are angled out and away from the camera

305 or camera window 305'. As shown, the camera window plane is perpendicular to the longitudinal axis, e.g. on the X-Z plane, but could also be angled relative to the X-Z plane. The working channel ports 304 are symmetric about the X-Y plane. One of the working channel ports is disposed on a plane 304' at an angle ax to the X-Y plane and the other is disposed on a plane 304" at an angle xb to the X-Y plane. Angles ax and xb have the same magnitude. The magnitude may be between about 30-70 degrees+/−1, 5, 10, 15, or 20%. Planes 304' and 304" can also be between about 5-25 degrees+/−1, 5, 10, 15, or 20% about the Y-Z plane, although other degrees of rotation are contemplated. This configuration prevents the object, e.g. stone 362, from completely obstructing the view from the camera when the object is engaged with the suction port or working channel. The light or light window 301, 301' is recessed below, or proximally from, the camera 305. The configurations shown in FIGS. 23a-d are for illustrative purposes only. It is not necessary that the ports of the working channels be planar.

Figure 23B:
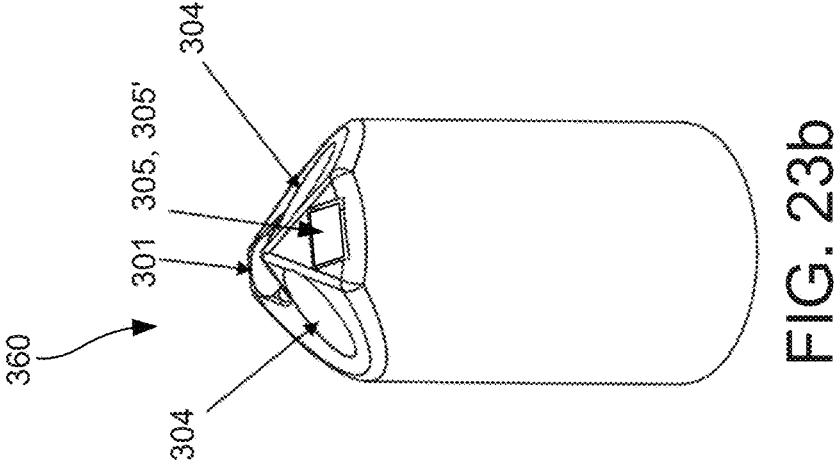
FIGS. 23a-23h show another embodiment of a distal tip of devices of the present disclosure.
Figure 23A:
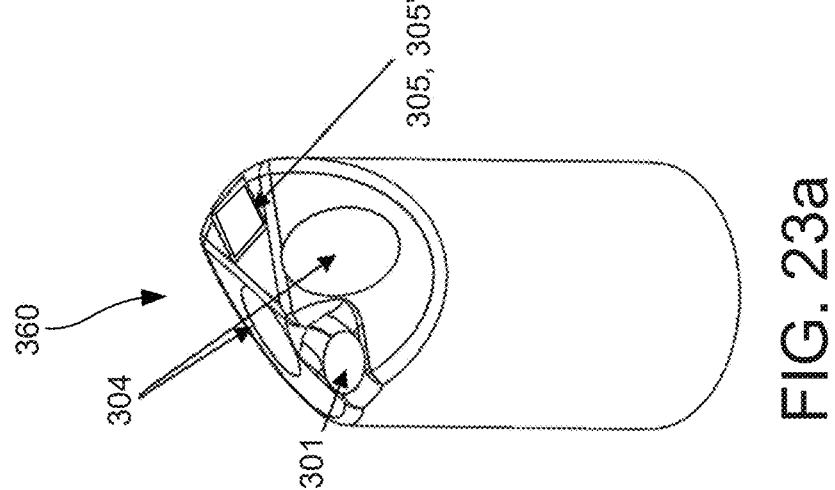
Figures 23C, 23D:
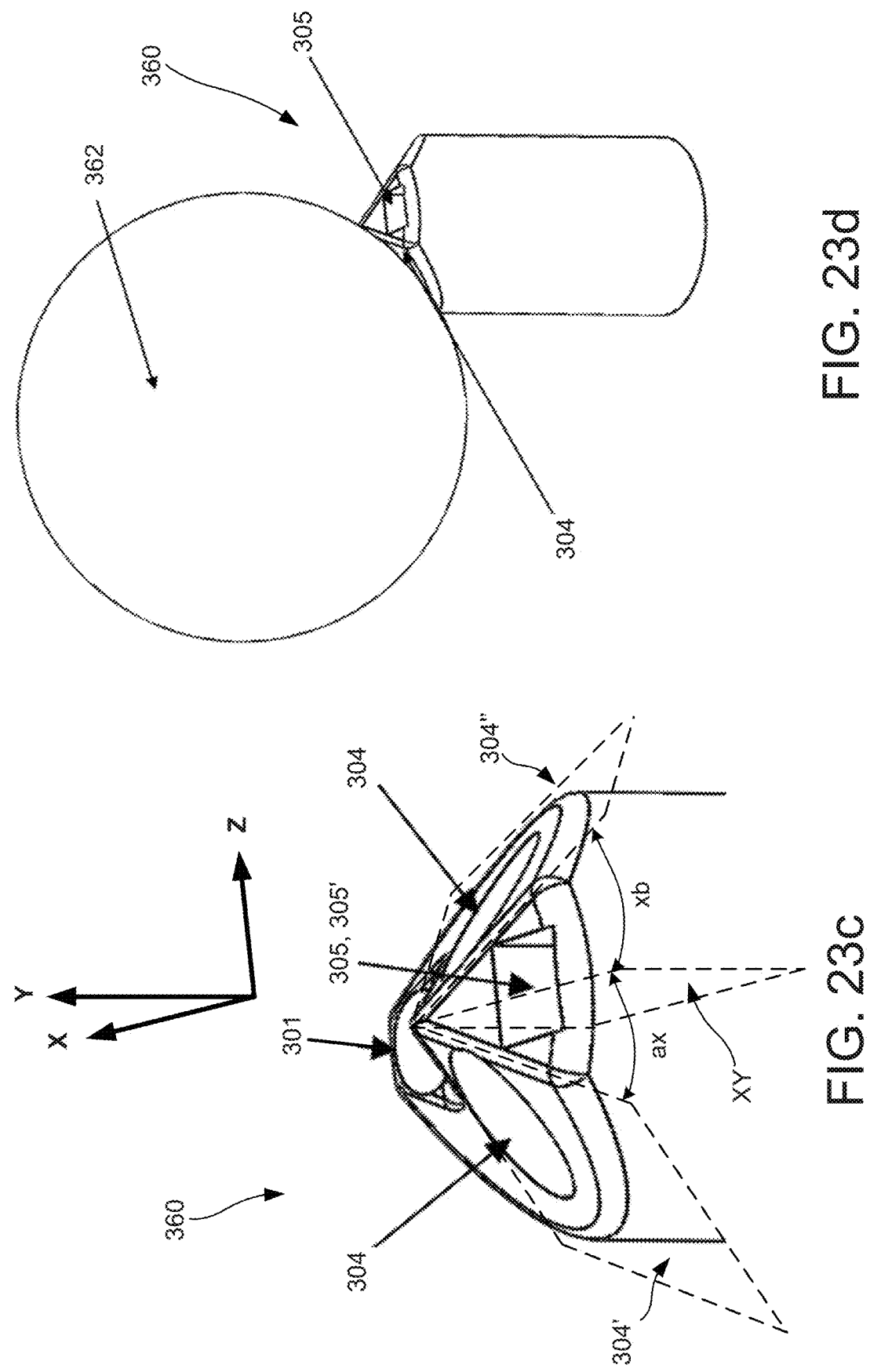
Figure 23E:
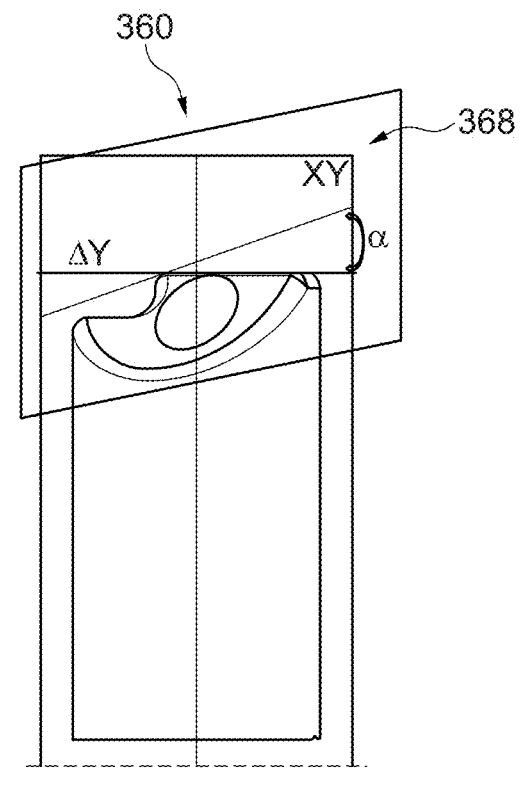
Figure 23F:
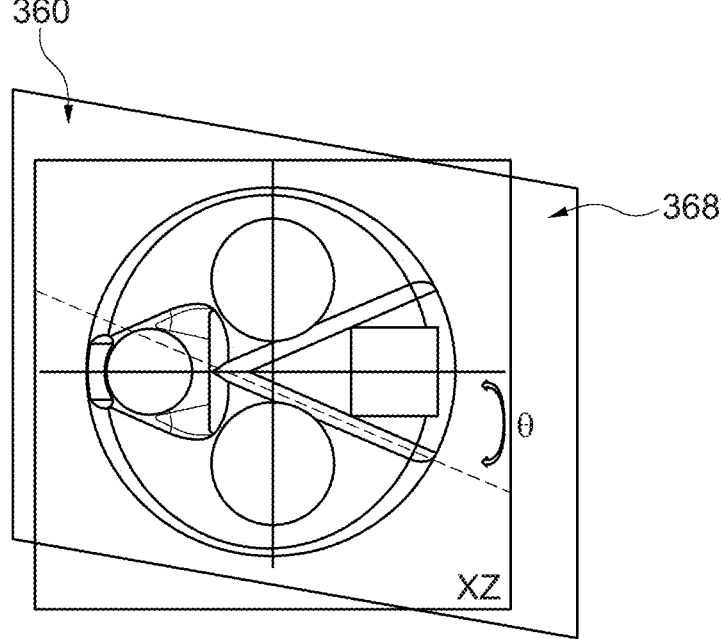
Figure 23H:
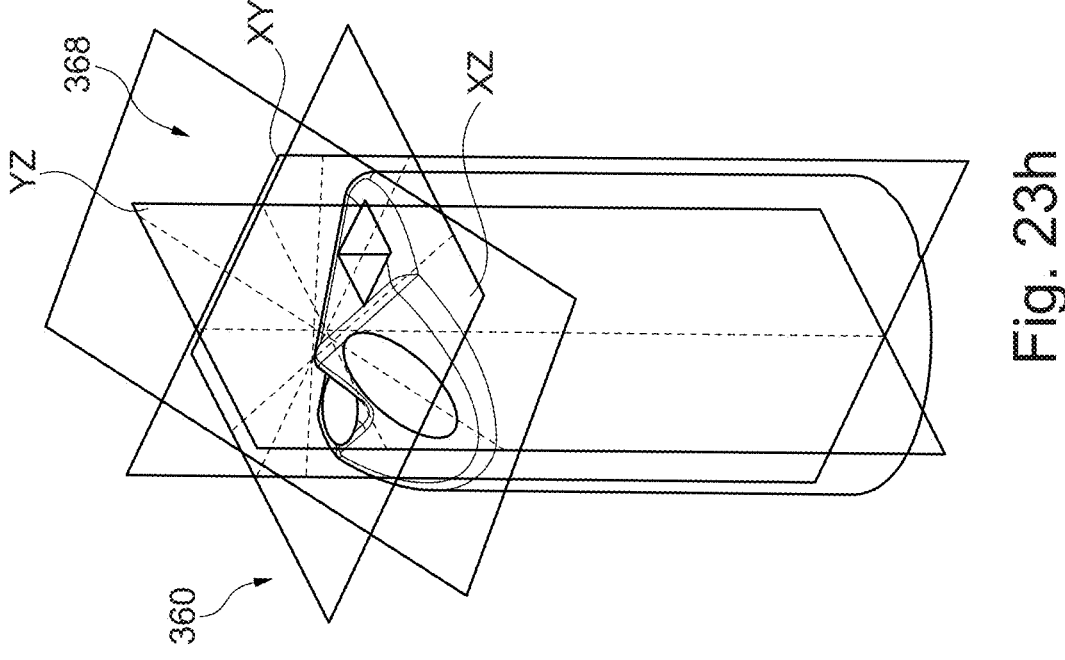
Figure 23G:
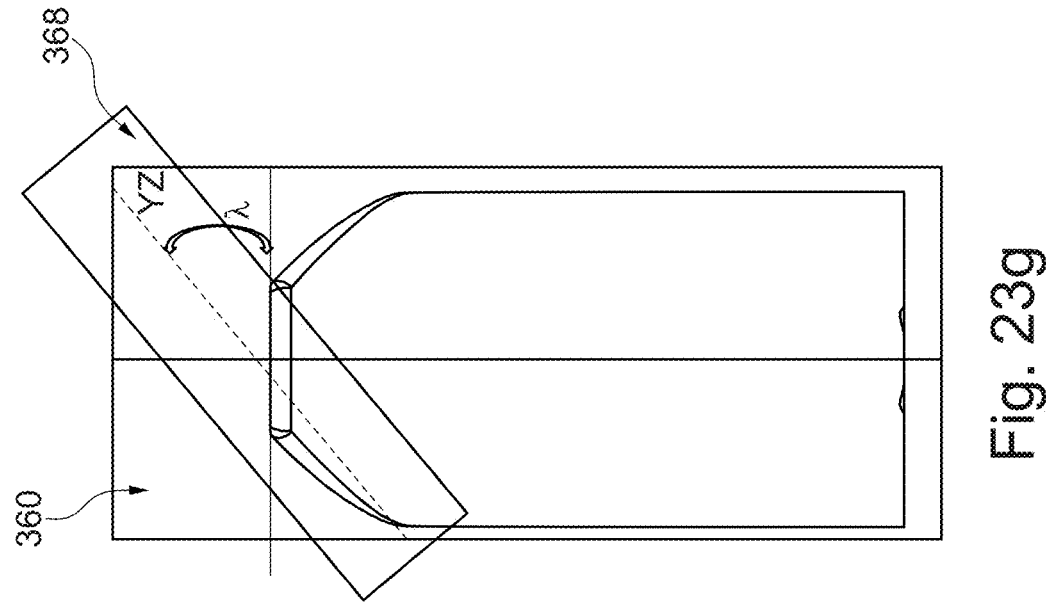

FIG. 23e is a view of the distal tip 360 on the X-Y plane. The working channel port 304 is on a plane 368. The angle where plane 368 intersects the X-Y plane of view is labelled as a. The change in height of the plane 368 relative to the plane of the camera window 305' is shown as ΔY. FIG. 23f is a view of the distal tip 360 on the X-Z plane. The angle where plane 368 intersects the X-Z plane of view is labelled as θ. FIG. 23g is a view of the the distal tip 360 in two dimensions on the Y-Z plane. The angle where plane 368 intersects the Y-Z plane of view is labelled as λ. FIG. 23h is a three-dimensional view of the distal tip 360 with the working channel plane 368 shown with the X-Y, X-Z, and Y-Z planes. This view shows the rotation and corresponding rotation angles of the working channel plane 368 relative to each of the other planes.

Figures 24A, 24B:
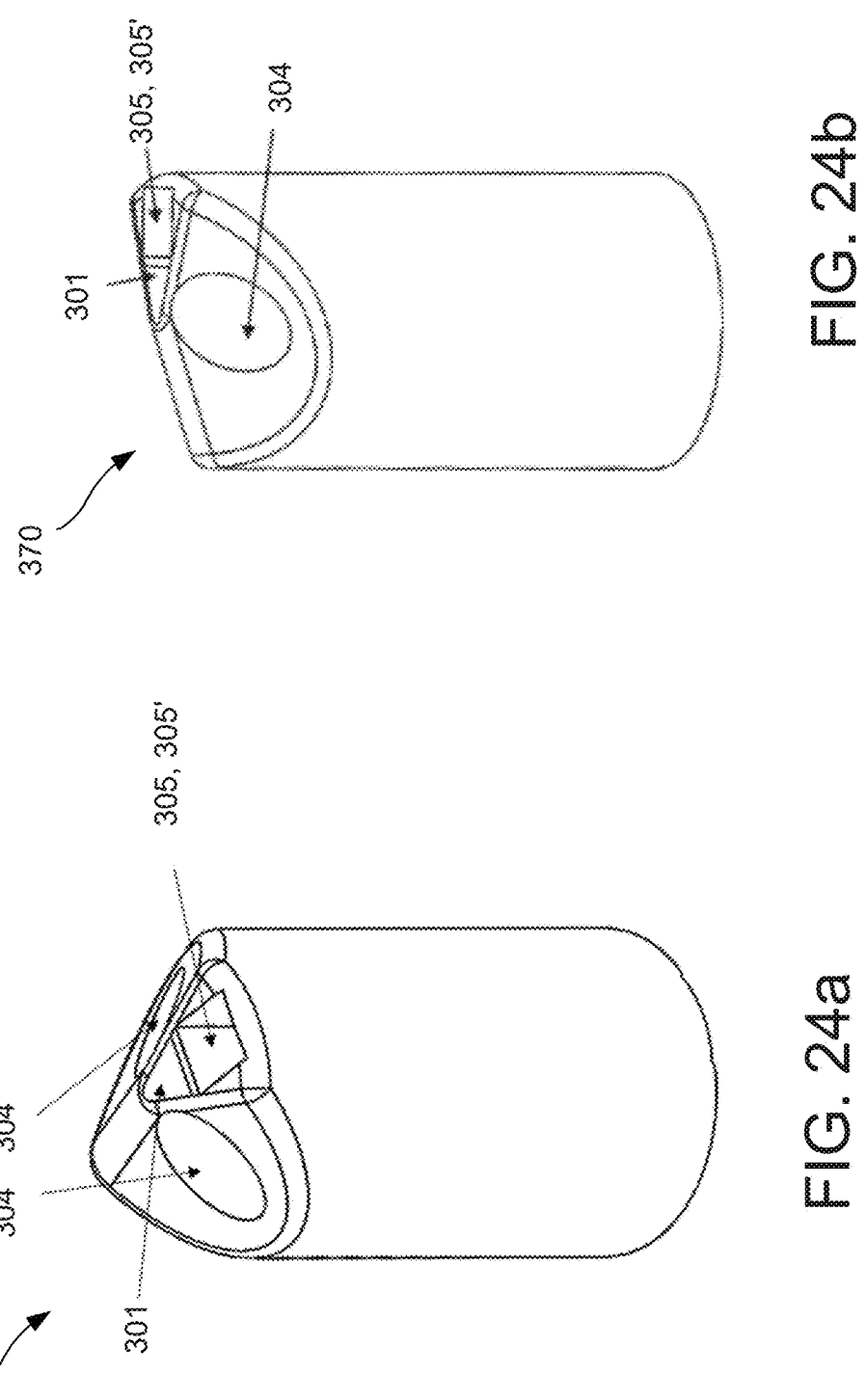
FIGS. 24a and 24b show another embodiment of a distal tip of devices of the present disclosure.

Now referring to FIGS. 24a-b, shown is an alternative embodiment of a device with a distal tip 370, where the camera 305 or camera window 305' and the light 301 or light window 301' are adjacent to each other on the same plane. The working channel ports 304 are positioned as described with reference to FIGS. 23a-e, angled out and away from the camera 305 or camera window 305'. The light 301 or light window 301' are shown to have the shape of a triangle. In prior embodiments the light 301 or light window 301' were shown to be circular. However, the light can be made in various configurations to minimize the cross-sectional area of the distal tip and thus can be arranged to suit the available space. In the present embodiment a triangular light or a rectangular or circular light smaller than the shown triangle can be used. It is contemplated that placing the light 301 adjacent to the camera 305 may improve illumination of the field of view when a stone is engaged with the suction port. The light 301 and the camera 305 or camera window 305' are on plane/planes perpendicular to the longitudinal axis of the device and the working channel port 304 is on a different plane.

The present disclosure is not limited to the light configurations shown in the drawings. In some embodiments, all or part of the device tip is illuminated instead of having a discrete light port. In some embodiments, fiber optics where the light is transmitted through the scope to the distal end of the tip are utilized to illuminate all or part of the device tip. In some embodiments, at least part of the tip is constructed from a translucent or transparent material (e.g., a colorless thermoplastic), such that the light is transmitted through the tip and illuminates the kidney for visualization. Different areas of the tip may also have a frosted surface such that the light from the fiberoptic fiber strategically disperses out and illuminates the kidney.

The distal tip housing of the distal tip (any of the distal tips described hereinabove and below) is constructed of any suitable material. In some embodiments, the tip is constructed of rigid materials such as including but not limited to, a thermoplastic, metal, or a combination thereof. Alternatively, at least part of the distal tip may be constructed of a compliant softer material such as, including but not limited to, a silicone elastomer, thermoplastic elastomer, or a foam. For example, in some embodiments, the region around the entrance of the suction port (e.g. the compliant regions 306, 306' shown in FIGS. 16a-c and 19a-b) is constructed from a compliant material, which can at least partially deform to fit the shape of the kidney stone the user is manipulating for repositioning. In some embodiments, this region is raised up from the front tip wall or integrated into the tip wall.

In some embodiments, the compliant material has a Shore Hardness of between OO10 and A40 (See e.g., U.S. Pat. Nos. 1,770,045 and 2,421,449; each of which is herein incorporated by reference in its entirety for a discussion of Shore hardness). The Shore hardness is determined using a Shore durometer, which is a device for measuring the hardness of a material, typically of polymers, elastomers, and rubbers. Higher numbers on the scale indicate a greater resistance to indentation and thus harder materials. Lower numbers indicate less resistance and softer materials. The ASTM D2240-00 testing standard calls for a total of 12 scales, depending on the intended use: types A, B, C, D, DO, E, M, O, OO, OOO, OOO-S, and R. Each scale results in a value between 0 and 100, with higher values indicating a harder material. Each scale uses a different testing foot on the durometer.

In some embodiments, other parts of the tip have a hardness greater than A40. The compliant region is, for example, formed out of a solid piece of material or have porosity or be hollow or a combination thereof.

In some embodiments, the suction port comprises one or more anti-clog elements. In some embodiments, the suction port comprises an anti-clog inlet shaped such that it impedes or prevents stone fragments that may get clogged within the suction tubing. This can be done, for example, by making the suction port opening more restrictive than the inside diameter of the suction tubing (e.g., by narrowing the opening, having a mesh across the opening, or having a bar or beam in front of the opening). In some embodiments (e.g., FIG. 18), the anti-clog element comprises a plurality of protrusions or depressions that prevent stones from occluding the suction port 302.

The suction port 302 and working channel 304 can be in any configuration or used interchangeably. For example, they can be oriented across or distal from each other or next to each other or another configuration.

Figure 25A:
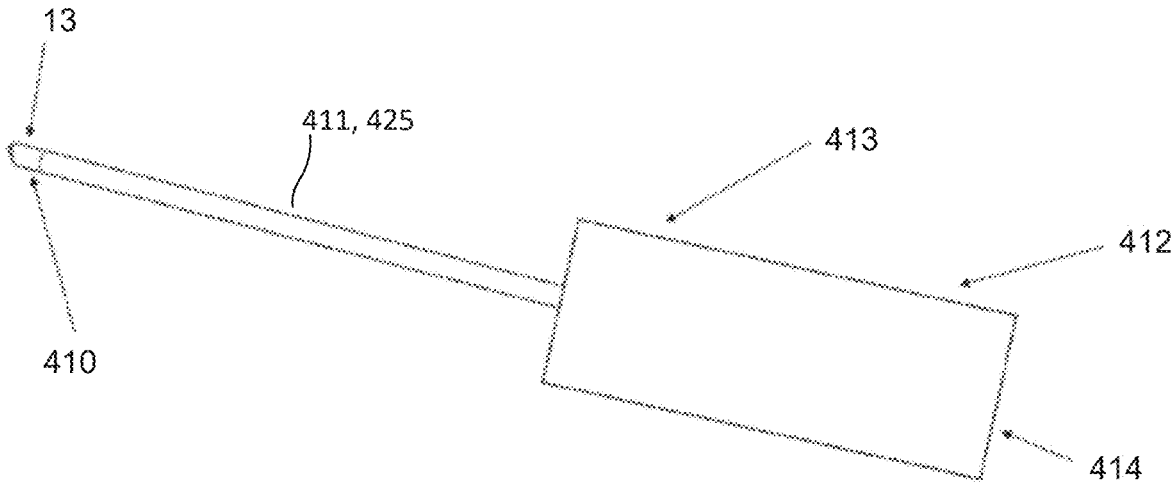
FIG. 25a shows an alternative embodiment of a device of the present disclosure.
Figures 25B, 25C:
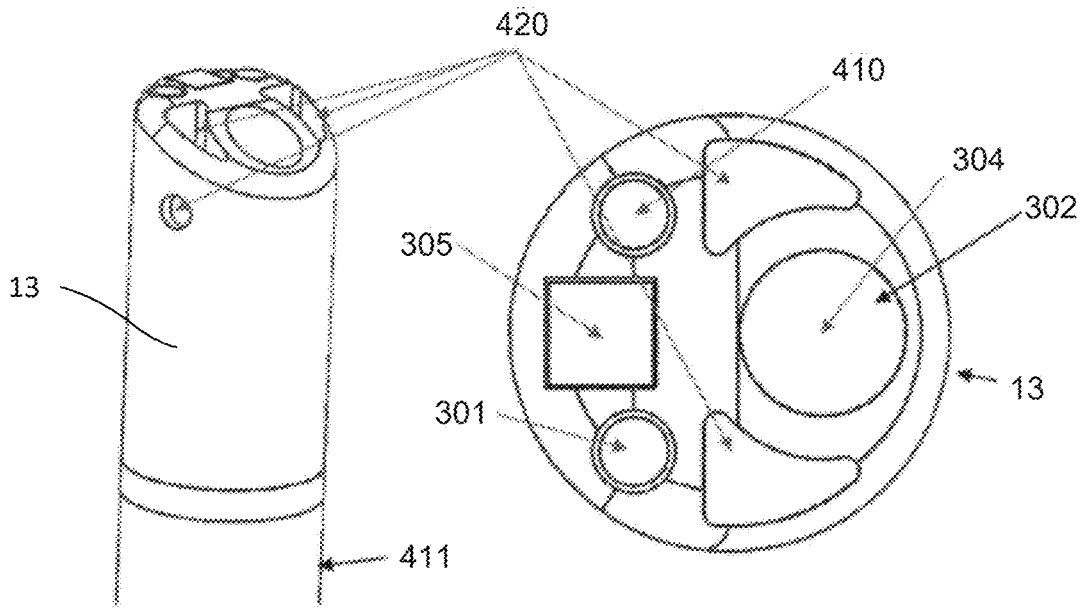
FIGS. 25b-25g show another embodiment of a distal tip of devices of the present disclosure.

FIG. 25a is another diagrammatic representation of an endoscope such as the endoscopes described with reference to FIGS. 1a, 2a, 2b, and 3a. FIGS. 25b and 25c illustrate components and features of the endoscope, some of which were previously described and new ones that can be incorporated in the previously described endoscope. The endoscope comprises the distal tip 13, a temperature and/or pressure sensor 410, an insertion cord 411 (which can be the same as insertion cord 10), a handle 413, a suction port proximal end 412, a working channel proximal end 414, and interstitial flow openings 420. The handle 413 can be any of the previously described handles, such as handles 2 and 2'. As described above, the endoscope includes an irrigation delivery system, a laser, a camera, and a mechanism to articulate the distal tip 13. In some embodiments, the handle/system includes a mechanism to linearly translate the laser forward and backward with respect to the long axis of the device (see FIGS. 13 to 15*c*) to unclog the tip when suction is applied through the working channel port 304 with laser included. If a clog occurs, it will tend to occur near the entrance of the tip. By moving the laser fiber backward then forward (by about an inch), one can quickly clear any stone fragments that may have clogged or partially clogged working channel port 304.

FIG. 25*b* shows two interstitial flow openings 420 located on the distal end of the device and one on the side. However, the present disclosure is not limited to such a number or configuration of interstitial flow openings 420. For example, in some embodiments, devices comprise one or more (e.g., 1, 2, 3, 4, 5, or more) interstitial flow openings 420. The interstitial flow openings are placed in any suitable location including but not limited to, on the tip or side of the device. The interstitial flow openings 420 in FIG. 25*b* comprise an interstitial flow opening 36 as shown in FIG. 2*a* and interstitial flow openings 37, also as shown in FIG. 2*a*.

The insertion cord 411 comprises an outer housing, or tube, 425 (which can comprise the outer housing 26 shown in FIG. 2*a*), and interstitial fluid openings 420 in fluid communication with the interstitial space 421. In some embodiments, this configuration utilizes cutouts (e.g., interstitial flow openings) placed at or near the tip (e.g., distal end) of the device to direct pressurized irrigation fluid into the kidney without disturbing the small stone fragments (e.g., improving popcorn lithotripsy efficiency). In some embodiments, this configuration utilizes cutouts (e.g., interstitial flow openings) placed at or near the tip of the device to direct pressurized irrigation fluid into the kidney to clear the small stone fragments (e.g., improving visualization). The outer housing serves as a pseudo-working channel for fluid delivery or suction. Herein, a pseudo-working channel is a channel that allows for fluid delivery and/or suction but cannot accommodate instrumentation exchanges such as passing a laser fiber or basket through the channel during the procedure since there is not a direct channel or tube connecting the interstitial flow opening(s) to a port outside of the patient (e.g. in the device handle). In some embodiments, irrigation fluid is pumped in between the inner surface of an outer housing and the outer surface of an inner working channel (e.g., via a fluid port). In some embodiments, fluid is removed through the interstitial space between the outer housing and the inner working channel (e.g., via a suction port). In some embodiments, both irrigation and suction are interchangeably applied through the interstitial space between the outer housing and the inner working channel. In some embodiments, the interstitial space and the working channel are substantially (e.g., completely or partially) fluidly separate.

The present disclosure is not limited to a particular material for outer housing 425. In some embodiments, outer housing is constructed of one or more materials commonly used in ureteroscopes (e.g., a flexible polymer, a metal such as stainless steel, a rigid plastic, and/or a laser cut or electrical discharge manufacturing (EDM) cut hypotube)

FIG. 25*c* is a perspective view showing the interstitial space 421 in the outer housing 425. Also shown are the working channel tube 42 that ends in the working channel port 304, pull wires 58*a*, 58*b*, a light 301, a camera cable 422, and a pressure sensor cable 423. FIG. 25*d* is a side view showing an interstitial fluid opening 420 on the circumferential wall 308 of the distal tip 13, with an object 362 engaged with the working channel port 304. The interstitial flow opening 420 is outside the area where the object is engaged. Flow openings 420 may be placed in other suitable locations.

Figure 25E:
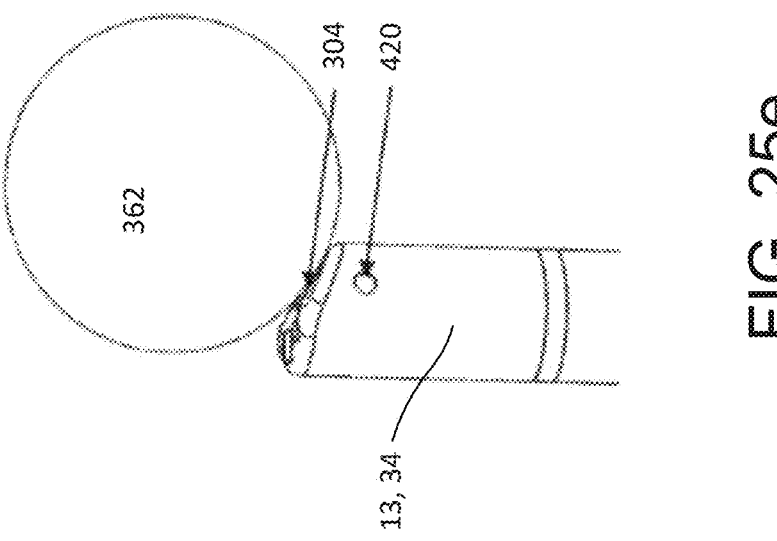
Figure 25D:
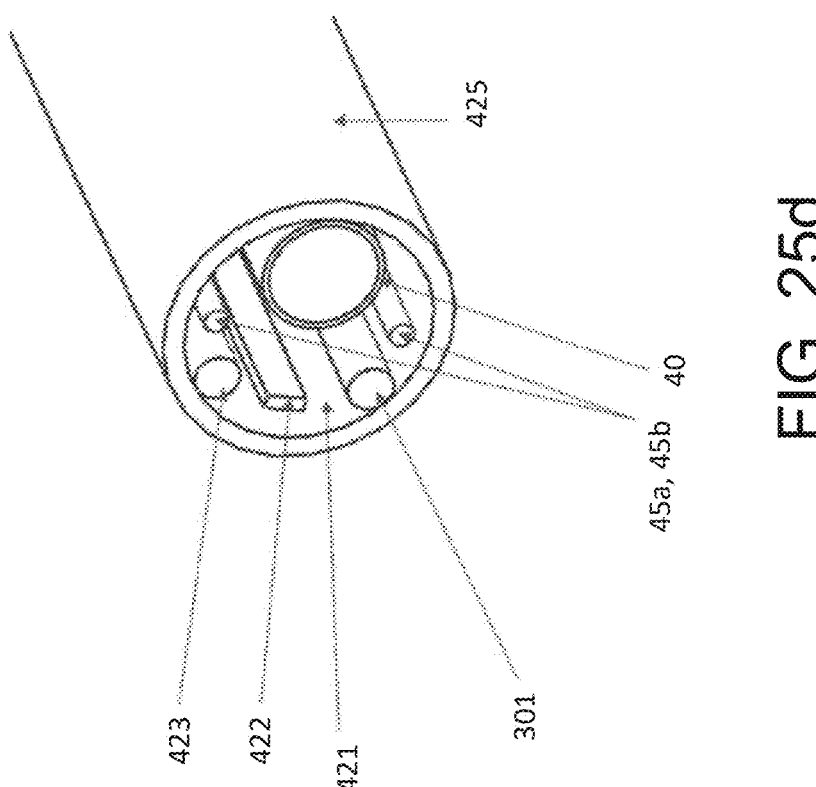
Figure 25G:
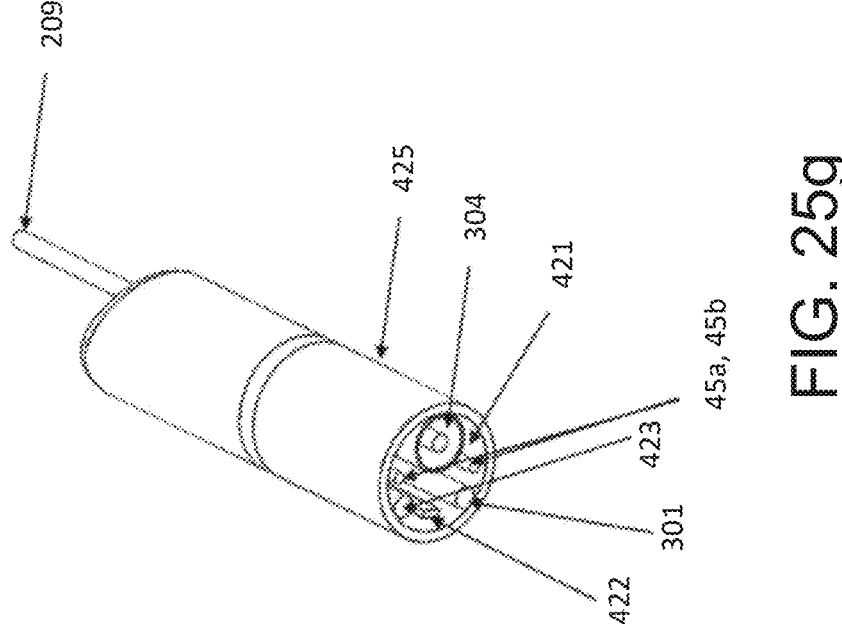
Figure 25F:
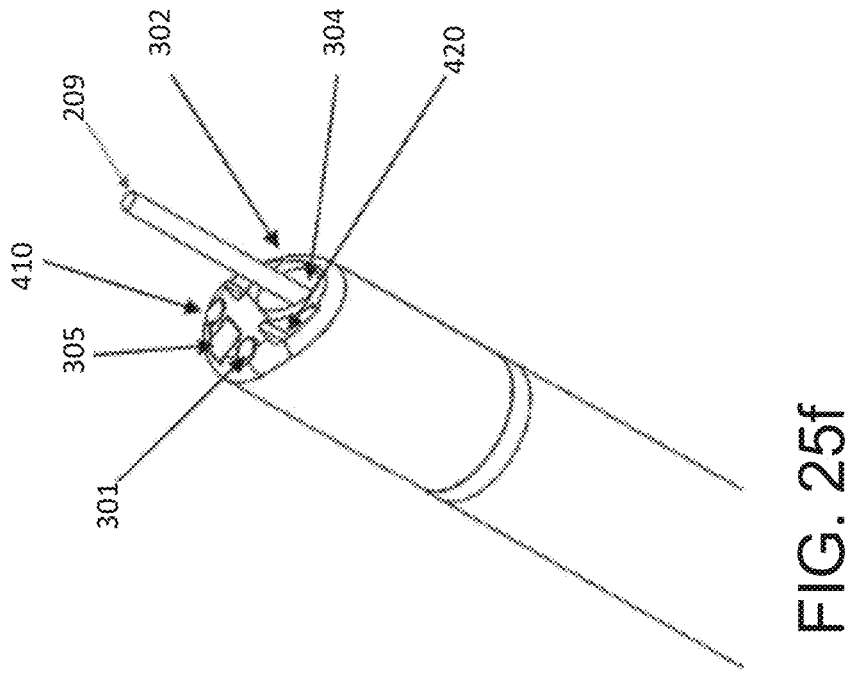

FIGS. 25*e* and 25*f* show the laser fiber 209 protruding, respectively, from the suction port 302 and the working channel port 304. When in use, the laser fiber 209 does not block the camera 305 or the light 301. The working channels are fluidly isolated from the interstitial space 421, providing two distinct channels suitable for suction and/or fluid delivery.

Mesh/Filter

FIGS. 26*a-d* show a device similar to the device of FIGS. 25*a-f* that utilizes multiple working channels and the interstitial space. In some embodiments, by way of example, a first, smaller working channel with an inner diameter channel of ~1.5Fr or 0.5 mm (e.g., plus or minus 5, 10, 15, 20, or 25%) is utilized for a laser fiber 209 (~0.4 mm OD). This working channel is of small diameter (e.g., just large enough for a laser fiber) since fluid does not need to pass through this working channel. This allows the scope outer diameter to remain small. In some embodiments, a second, larger, working channel is utilized, of ~3.6Fr or 1.2 mm (e.g., plus or minus 5, 10, 15, 20, or 25%) inner diameter, to suck fluid through. In some embodiments, the interstitial flow opening includes a flow diverter (e.g., as shown in FIGS. 16*a* and 16*b*) to help prevent clogging of the larger working channel. Also shown are a mesh/filter 432 which is pivotable about an axis 433 to enable, for example, passage of a tool through the working channel.

Figures 26A, 26B:
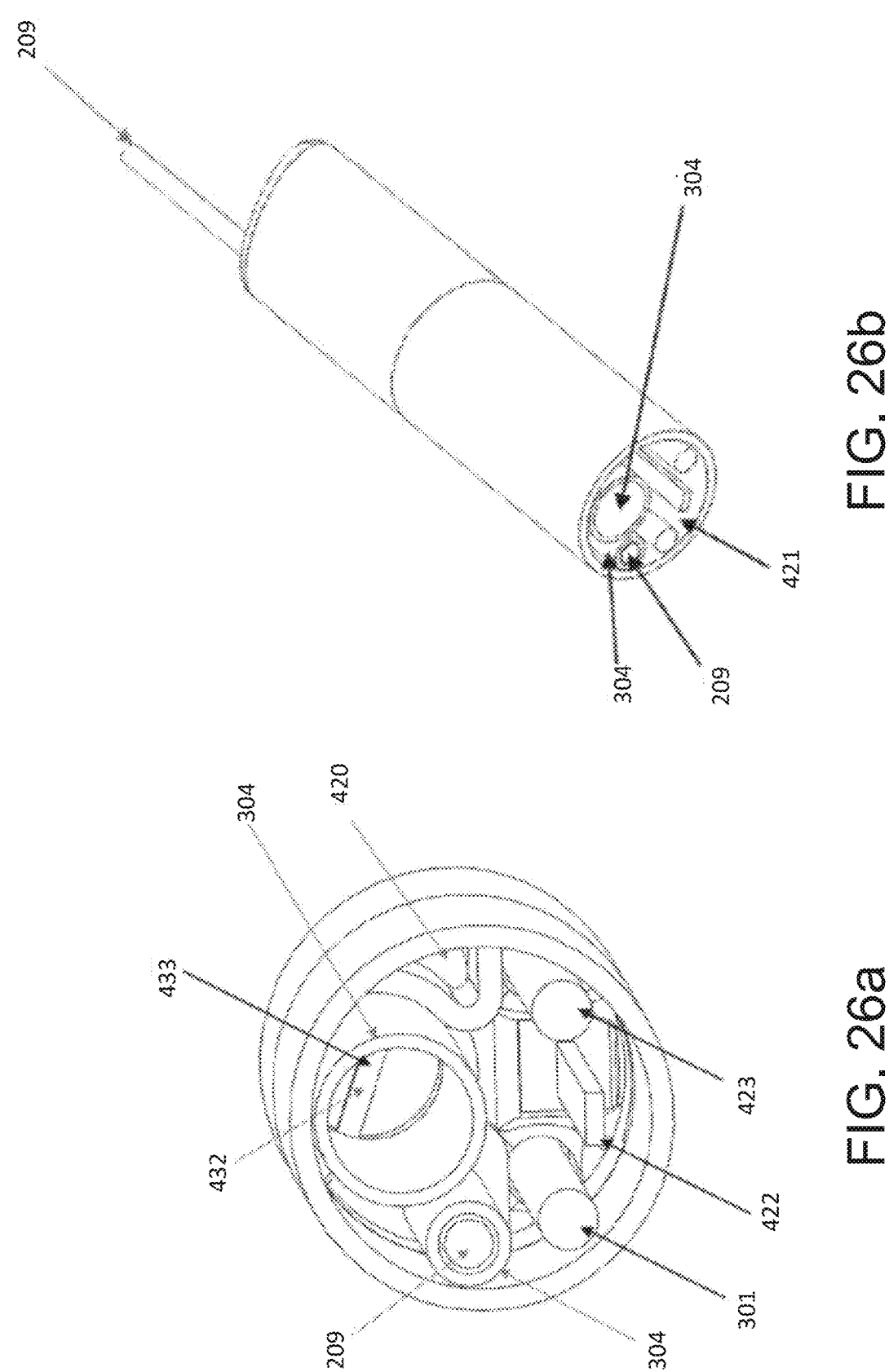
FIGS. 26a-26d show another embodiment of a distal tip of devices of the present disclosure.
Figure 26D:
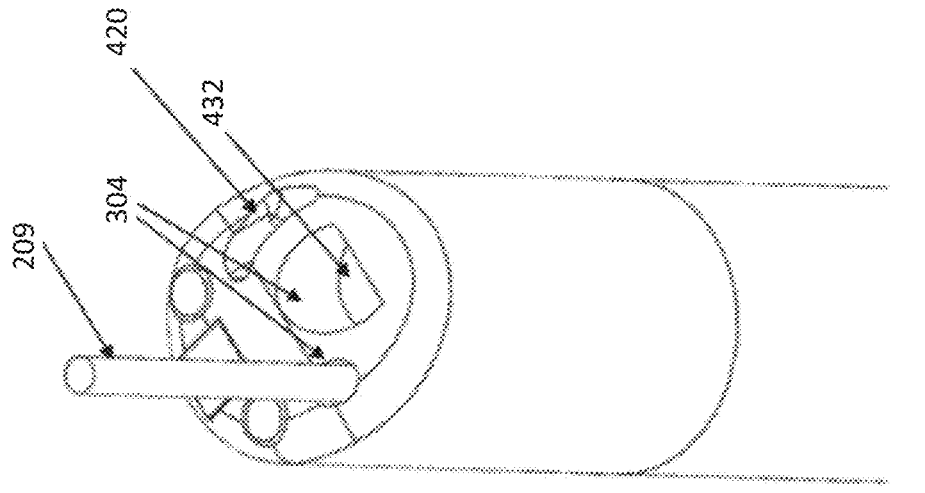
Figure 26C:
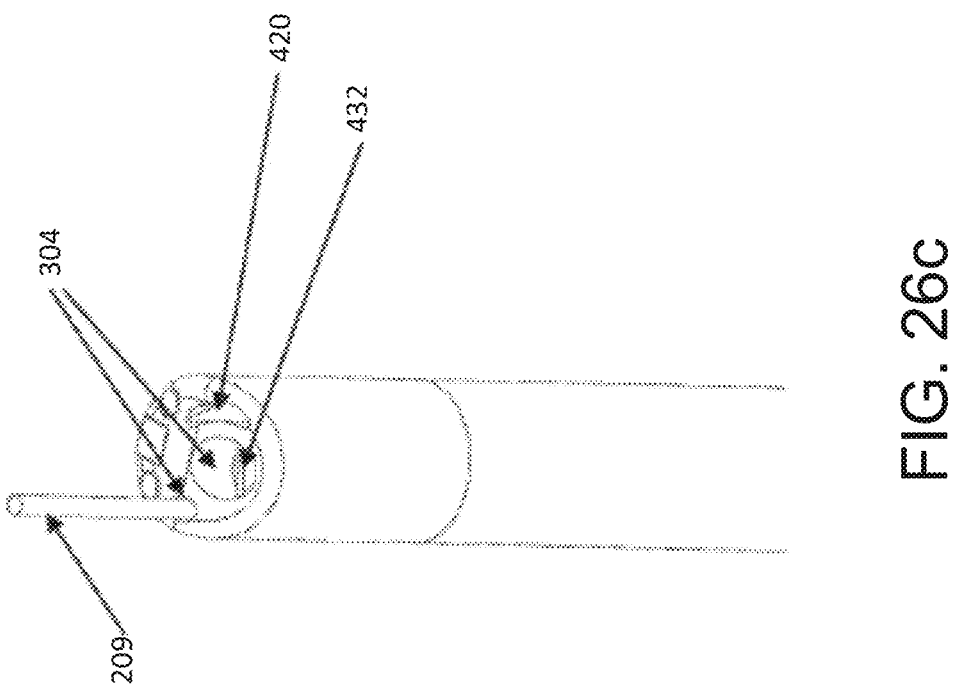

In some embodiments, the working channel optionally includes a fragment filter/mesh 432 to prevent fragments from entering the working channel, which may clog it. In some embodiments, the filter/mesh is optionally recessed to allow for larger fragment grabbing and extraction. In some embodiments, the filter/mesh is pivotable about an axis 433 and/or flexible to allow an instrument to pass through/past the filter unimpeded. Then, when the instrument is removed, the filter/mesh moves back into place to prevent clogging in the working channel. While the filter is illustrated on the configuration shown in FIGS. 26*a*, 26*c*, and 26*d*, the filter is suitable for use on any device configurations described herein. In FIG. 26*d* filter 432 has a narrowed rigid opening that allows an instrument to pass through.

In an alternative embodiment, the laser fiber is separate from any working channel and resides in the interstitial space within the pseudo working channel. In some embodiments, the laser fiber extends past the distal tip of the endoscope.

Figure 27B:
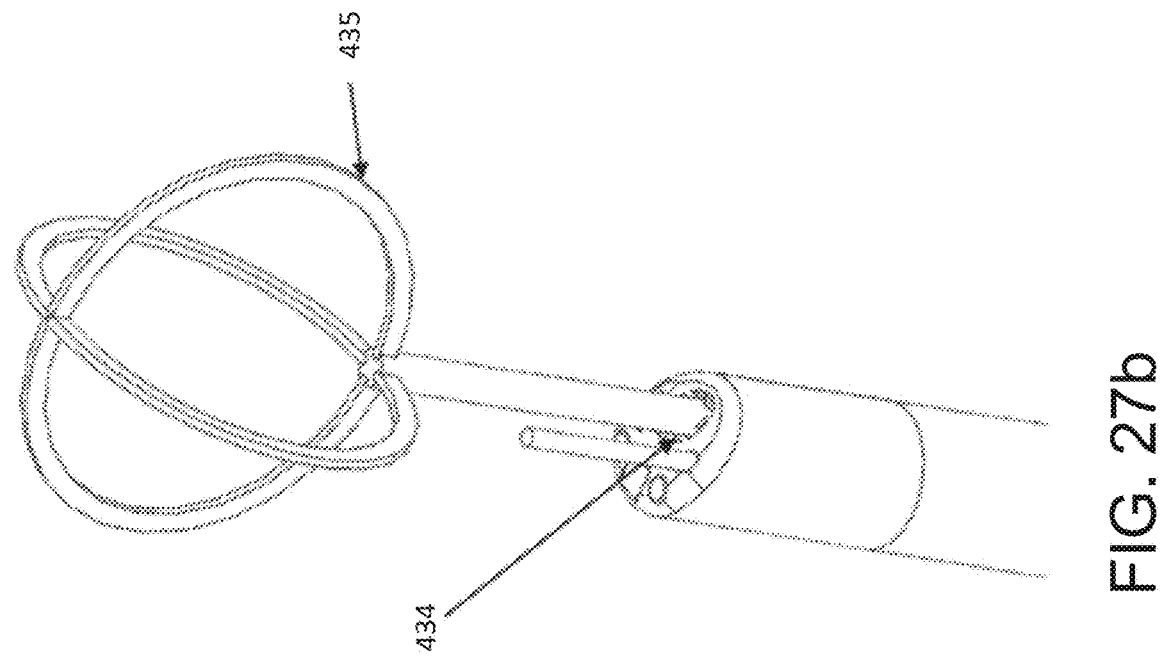
FIGS. 27a and 27b show another embodiment of a distal tip of devices of the present disclosure.
Figure 27A:
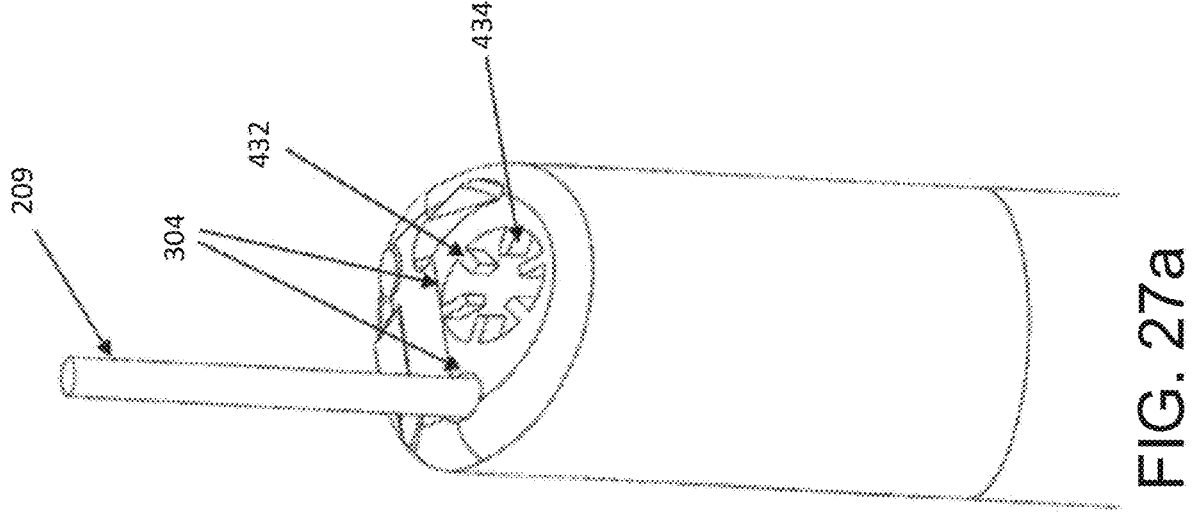

FIGS. 27*a* and 27*b* show a further configuration of the filter 432 that allows an instrument to pass through. Shown is the first working channel port 304 comprising the laser fiber 209 and the second working channel port 304 comprising the filter 432, which comprises one or more elastic elements 434 that protrude in the channel. Six (6) protrusions are shown, although other numbers may be utilized. When an instrument like a basket 435 is inserted, it pushes the elastomeric elements 434 out of the way so the instrument can pass in and out. Then, when no instrument is in place, the elastomeric elements spring back into place acting to partially occlude the channel opening minimizing clogging within the working channel. In some embodiments, the elastomeric elements are composed of a material such as a thermoplastic elastomer or silicone elastomer, and have a shore A hardness between approximately 10A and 50A. In some embodiments, the elastomeric elements are comprised by the compliant region 306 (see FIGS. 16*a-d*).

In some embodiments (e.g., those described in FIGS. 25e-f and 26a-d), the working channel is used to deliver a laser fiber 209. However, the working channel 304 (and other channels) are also suitable for delivery of additional device components (e.g., a basket or a pair of graspers). In addition, in embodiments that utilize the interstitial space for irrigation, the working channel can be fully or partially occluded with one or more instruments while still delivering adequate irrigation at the tip of the device.

In some embodiments, devices of the present disclosure (e.g., comprising outer housings, fluid ports, and interstitial spaces and other element described herein) are constructed de novo. In some embodiments, a commercially available ureteroscope or other devices designed to be used laparoscopically are modified to include such elements (e.g., including but not limited to, those available from Dornier MedTech, Munich, Germany or Richard Wolf, Vernon Hills, IL). In some embodiments, existing devices that comprise outer housings are utilized. In some embodiments, a fluid port is added to the device and the internal components are sealed to allow irrigation to flow from the fluid port (e.g., located on the handle) to the tip of the scope through the existing interstitial space. In some embodiments, one or more interstitial flow openings are added to the tip of the device to allow irrigation to be pumped into the kidney or other location. In some embodiments, this irrigation is pumped in without disturbing any stones or stone fragments present.

Flow Diverter

Figures 28A, 28B:
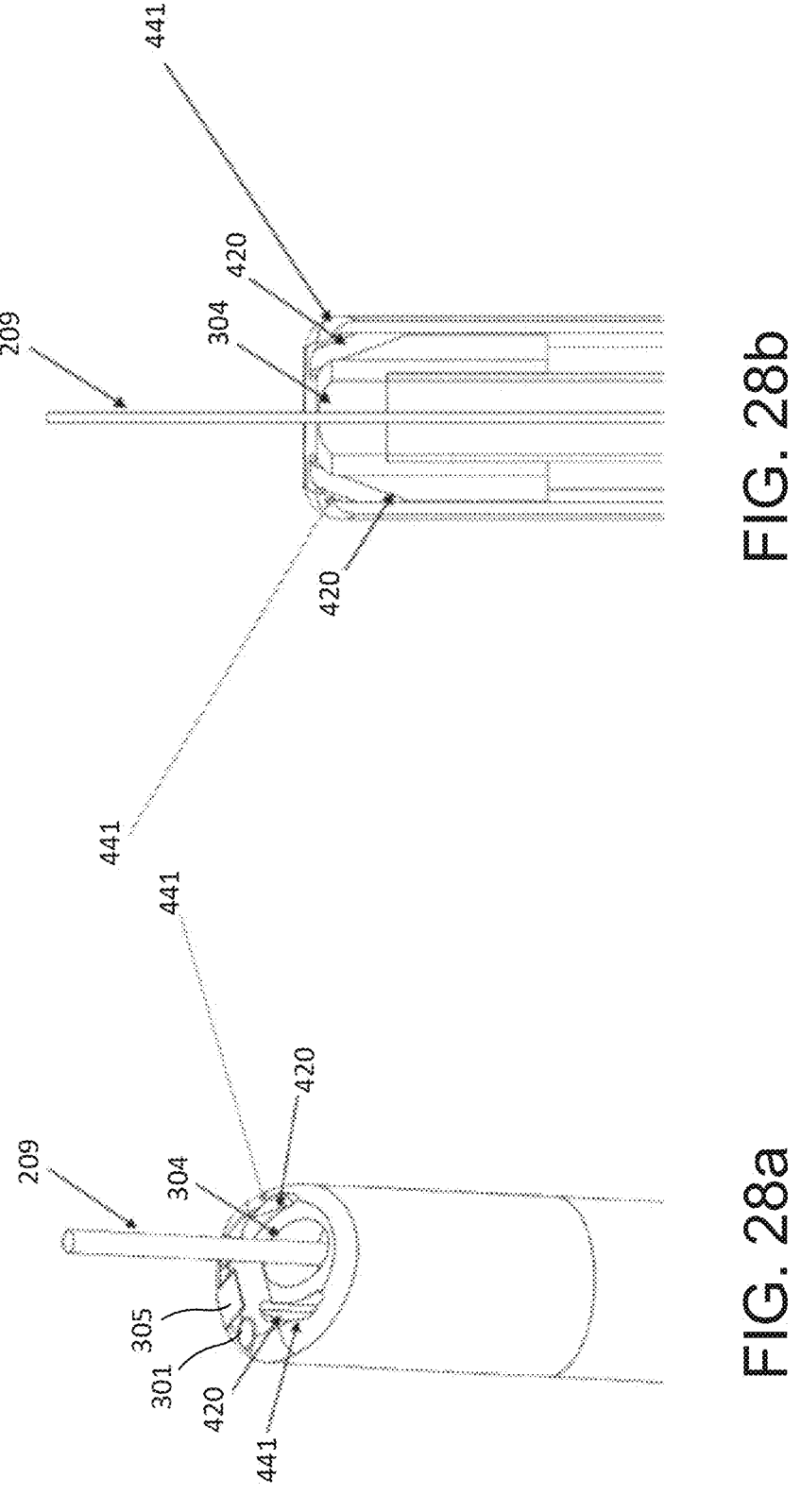
FIGS. 28a and 28b show another embodiment of a distal tip of devices of the present disclosure.

Now referring to FIGS. 28a and 28b, flow diverters in or adjacent to the irrigation/suction/working channels are provided to direct irrigation flow towards, across, and/or through a suction opening (e.g., working channel). In some embodiments, the flow diverter functions as a fluidic particle filter. For example, directing irrigation flow near or across the suction opening redirects or filters out larger stone particles or fragments, which could tend to clog or obstruct the suction channel. For example, with a 3.6 Fr (1.2 mm) diameter working channel, a 0.4 mm diameter laser fiber inserted into the working channel, and suction being pulled on the working channel, it is advantageous to only allow stone fragments or particles that are below approximately 0.3 mm in diameter to enter the working channel. This helps to ensure that the particles are sucked through the working channel and out of the scope without having to remove the laser fiber. This is advantageous from a procedural standpoint since the clinician does not have to pause the lithotripsy procedure in order to clear their vision of particles floating in their field of view.

It is also useful to balance the irrigation flowrate and the suction flowrate. A higher irrigation rate pushes particles and fragments away from the scope/suction opening, while a higher suction flowrate pulls particles and fragments toward the scope/suction opening. For kidney stone dusting, preferred irrigation rates are approximately 15-30 ml/min and preferred suction rates are approximately 8-17 ml/min. However, these rates can change depending on the geometry of the tip and the procedural scenario in which the device is used.

FIG. 28a shows a device comprising exemplary flow diverters 441. FIG. 28b is a cut-out side view of FIG. 28a. The flow diverters 441 are located adjacent the working channel 304 comprising the laser fiber 209. The flow diverters 441 are located at the opening of the interstitial opening 420 and are configured to direct irrigation (e.g., provided through interstitial openings 420) towards the suction opening (e.g., the working channel port 304 comprising the laser fiber 209). Two interstitial openings 420 and two flow diverters 441 are shown, although fewer or more interstitial openings and flow diverters are specifically contemplated. The present disclosure is not limited to interstitial openings. Other channels which do not rely on the interstitial space and utilize tubes instead may be utilized to deliver irrigation and/or suction and flow diverters 441 may be placed adjacent such channels.

Figures 29A, 29B:
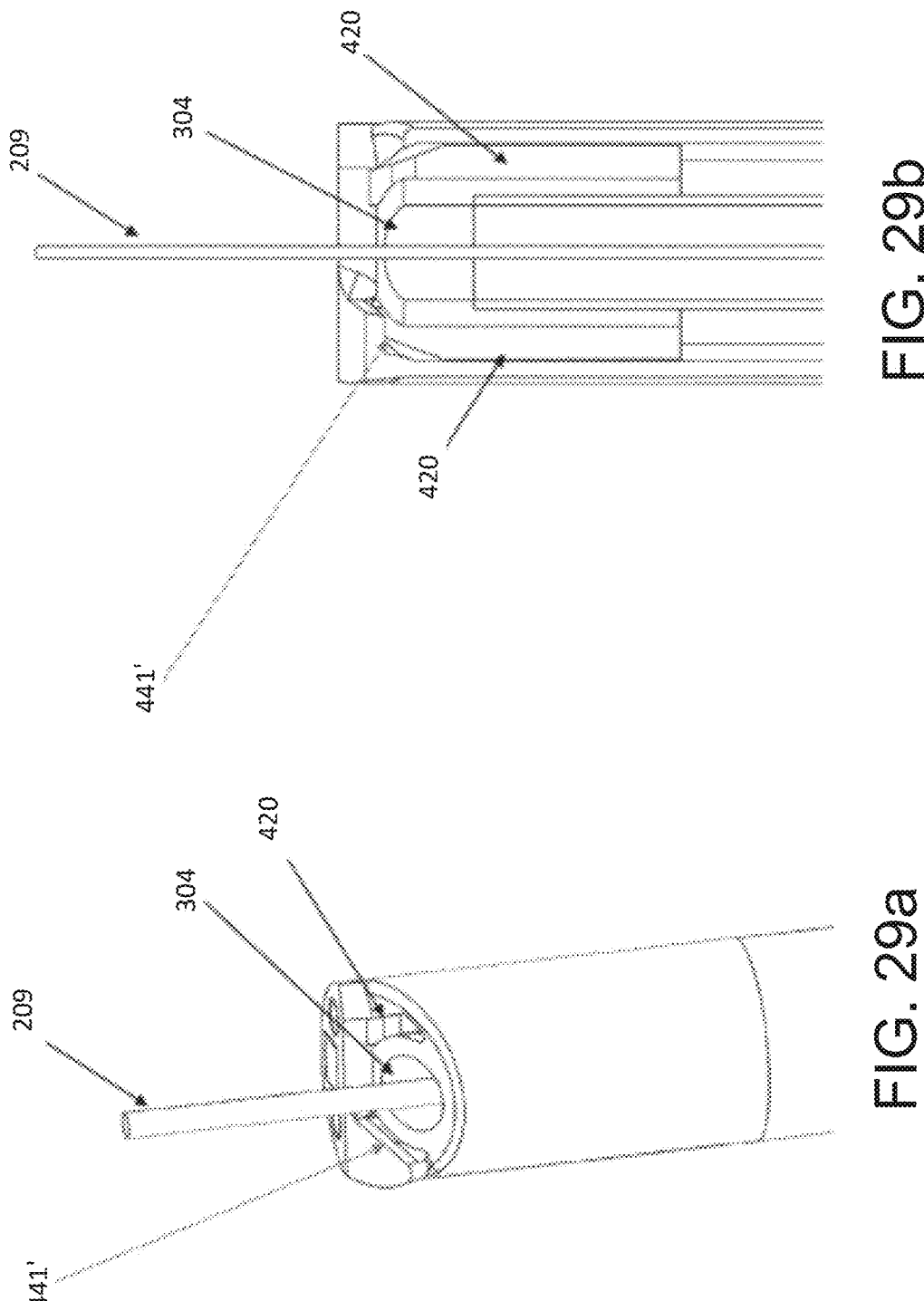
FIGS. 29a and 29b show another embodiment of a distal tip of devices of the present disclosure.

FIG. 29a shows a device, similar to the device of FIGS. 28a and 28b, comprising a flow diverter 441'. FIG. 29b is a cut-out side view of FIG. 29a. In FIG. 29a, the flow diverter 441' directs the irrigation flow across or partially across the working/suction channel port 304. The flow diverter 441' is flush with the outside, or distal, face of the tip of the device and has perpendicular sides adjacent to working channel port 304. Other shapes of flow diverters that are functionally equivalent may be used. The flow diverter 441' is located at the interstitial flow opening 420 and does not block the interstitial flow openings 420, which provide the irrigation fluid.

Figures 30A, 30B:
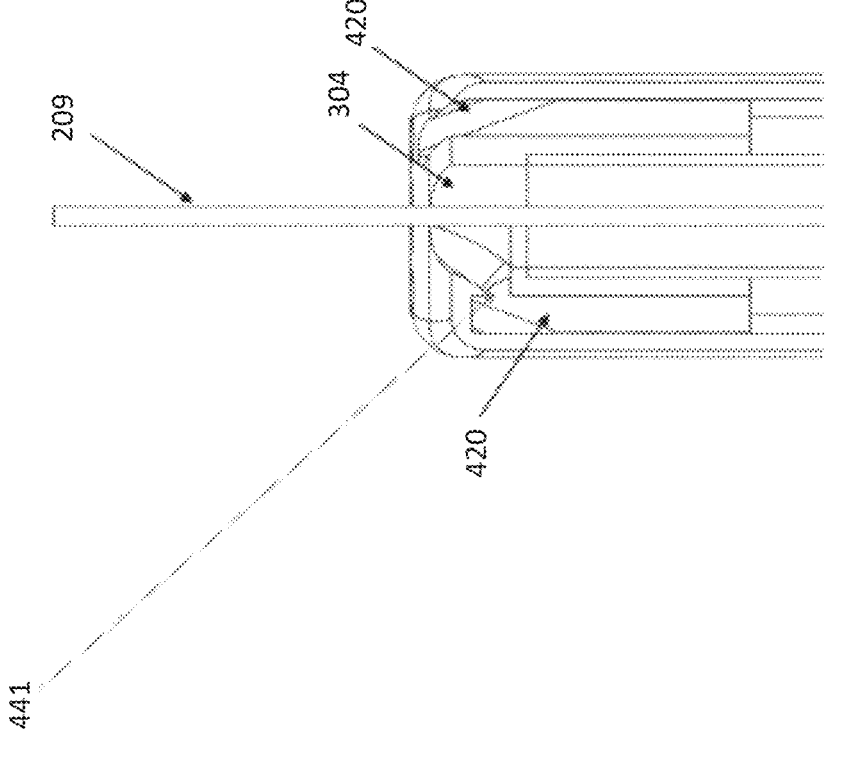
FIGS. 30a and 30b show another embodiment of a distal tip of devices of the present disclosure.

FIG. 30a shows an embodiment where the flow diverter 441 opens up to the working/suction channel 304 (e.g., comprising laser 209). Also shown in FIG. 30a are two interstitial openings 420. The flow diverter 441 directs fluid from the interstitial opening 420 on the left side in fluid communication with the flow diverter 441 to the working channel port 304.

FIG. 30b shows a cut-out side view of FIG. 30a. The flow diverter 441 is located at interstitial opening 420 on the left side of the view shown in FIG. 30b, which is in fluid communication with the working channel port 304. In the embodiment shown in FIG. 30b, irrigation is provided through the interstitial opening 420 adjacent the flow diverter 441 and is directed by flow diverter 441 towards working channel port 304. In some embodiments, the flow diverter 441 is composed of similar materials to that of the ureteroscope/endoscope tip. For example, this material may be a form of thermoplastic or metal. In some embodiments, the flow diverter 441 is molded integrally with the rest of the device tip or is attached as a separate component.

Figure 31C:
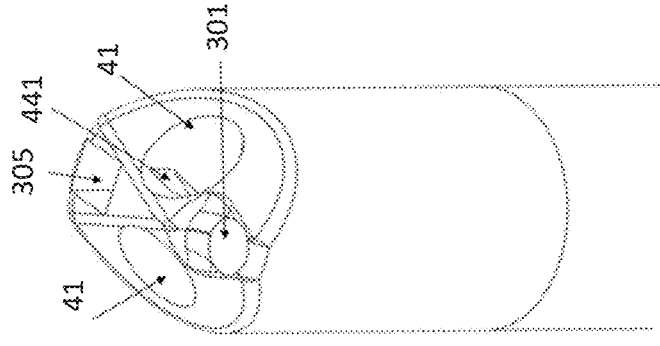
FIGS. 31a-31c show another embodiment of a distal tip of devices of the present disclosure.
Figure 31B:
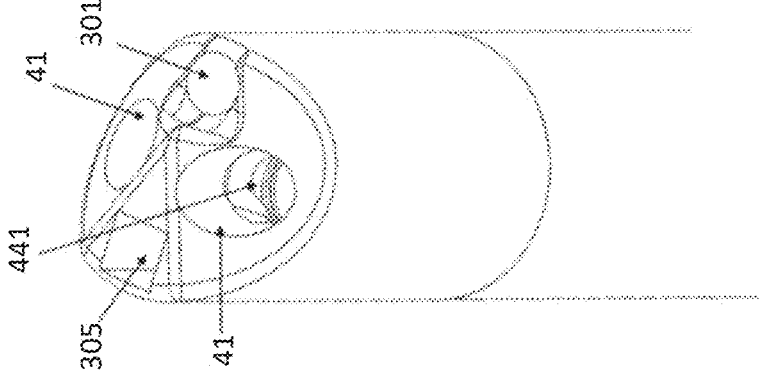
Figure 31A:
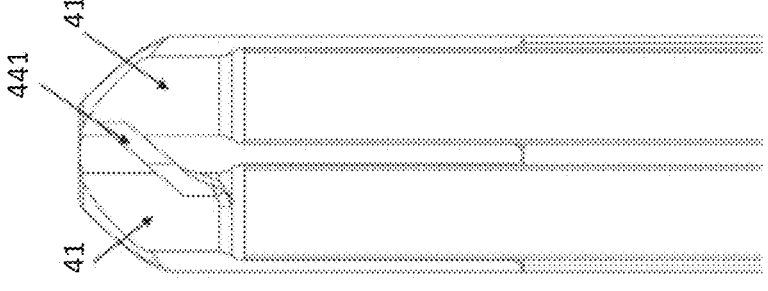

FIGS. 31a-c are views of a tip with a flow diverter 441 that links two working channels 41. FIG. 31a shows a side cut-out view of the device. The device shown in FIG. 31a lacks interstitial openings. Instead, irrigation is provided via a working channel 41. The flow diverter then directs flow of irrigation fluid from one working channel 41 towards the second working channel (e.g., comprising a suction component). The flow diverter is angled from an upper opening to a lower opening. FIG. 31b shows a top view of the device of FIG. 31a. Shown is the lower opening of flow diverter 441 into working channel 41 (the upper opening of flow diverter 441 in the second working channel 41 is not shown). Also shown are light 301 and camera 305. FIG. 31c shows a top view of the device of FIG. 31a. Shown is the upper opening of flow diverter 441 into working channel 41 (the lower opening of flow diverter 441 in the second working channel 41 is not shown). Also shown are light 301 and camera 305.

The present disclosure is not limited to the flow diverters described herein. In some embodiments, additional geometries and configurations of flow diverters are utilized. For example, in some embodiments, a combination of two or more (e.g., 2, 3, 4, 5, or more) flow diverters are utilized. In some embodiments, if more than one flow diverter is utilized, they are the same or different. In some embodiments, flow diverters are symmetrically or asymmetrically located on the distal tip of the device. In some embodiments, flow diverters are located adjacent an interstitial opening and/or working or other channel or port. In some embodiments, a device comprises channels with and without flow diverters.

The present disclosure is not limited to geometries or physical features of flow diverters. In some embodiments, the flow diverter comprises one or more physical features that divert an irrigation fluid stream in a direction other than perpendicular to the long axis of the device tip. In some embodiments, a flow diverter includes a structure, such as, for example, an angled channel opening, overhang, under- cut, channel link (e.g., where one working channel or "pseudo working channel" is linked to another working channel or "pseudo working channel" at or near the tip), or other structure, that acts to increase flow and/or turbulence at, near, within, or across a suction inlet on the endoscope.

In use, the ureteroscope tip is inserted in the ureter of a subject. The camera and articulation mechanism are used to advance the ureteroscope to the vicinity of a stone. Once a stone is visualized, laser ablation, in combination with irrigation and suction is performed. Once the stone has been ablated and debris fragments and stone dust have been satisfactorily removed via suction, the ureteroscope is removed.

In some embodiments, the irrigation flows through the working channel/laser port in a controlled manner. In some embodiments, a component for controlling the flowrate and total amount of irrigation fluid is included. The suction port can also be dynamically adjusted to control the flowrate and total amount of fluid that is removed from the kidney. These two systems work in unison to maintain a safe pressure balance within the kidney. For example, if the tip of the ureteroscope has engaged a stone for relocation, the tip may become occluded, thus reducing the amount of fluid that can be sucked out of the kidney. In some embodiments, the system senses this reduction of fluid removal and adjusts the amount of irrigation flowing into the kidney automatically. The suction intensity can also be adjusted. For example, if more suction force is needed to pick up a kidney stone or large fragment for relocation or extraction, the vacuum pressure is increased. Alternatively, once a stone has been moved to the desired location, the vacuum pressure is reduced or eliminated so the stone is released from the ureteroscope tip. The device can also include a pressure sensor to monitor the pressure within the kidney and adjust the in/out flow of fluid accordingly.

Additionally, in some embodiments, a temperature sensor is included on the tip or near the tip to measure the temperature of fluid within the kidney. If the temperature gets too warm due to laser dusting lithotripsy, the irrigation and suction intensity automatically respond to flow in colder fluid and remove warmer fluid.

In some embodiments, systems further comprise a side port to maintain suction even when a stone is engaged. In some embodiments, the side port comprises an actuation mechanism to selectively open and close the suction side port.

In some embodiments, a computer processor, computer, and display (e.g., monitor, smart phone, tablet, or smart watch) is used to operate one or more functions of the device, including but not limited to, to monitor and report temperature and/or pressure and/or move irrigation/laser and suction components between interchangeable channels. In some embodiments, a user reads the pressure and/or tem- perature and manually adjusts suction and/or irrigation to maintain an appropriate temperature and/or pressure. In some embodiments, the system adjusts suction and/or pres- sure automatically. For example, in some embodiments, the computer system both reads pressure and/or temperature, determines appropriate action, and instructs the suction and/or irrigation systems to make adjusts in flow and/or suction rate. In some embodiments, the computer system reads the temperature and/or pressure at regular intervals (e.g., multiple times per second, once per second, once every 5, 10, 30, 45, or 60 seconds, once per minute, or less often). In some embodiments, adjustments to flow and suction are continuously performed in order to keep temperature and pressure parameters within an acceptable range. For example, in some embodiments, temperature is maintained below 43 to 50° C. and intrarenal pressure is maintained below 40 cm $H_2O$.

The pressure sensor can be used to monitor the balance between fluid irrigation and suction. For example, it may be preferable to maintain a certain pressure in the kidney to distend the kidney prior to laser lithotripsy. However, too much pressure in the kidney can be detrimental to the patient. During kidney stone laser lithotripsy, it is preferable to maintain a suction at or below approximately 40 ml/min. In general, the greater the suction rate, the larger the size of stone fragment that will get sucked into the working chan- nel. By keeping the suction rate at or below 40 ml/min (e.g., below 20 ml/min), the stone fragments or particles that are sucked into the working channel will tend not to clog the device, hence it is preferably not to exceed this suction rate. By measuring the pressure at or near the tip, the system can adjust the suction and irrigation to the desired level. The system can also include an option to momentarily increase the suction amount (for example by pressing a button on the handle of the ureteroscope) to a pressure capable of exceed- ing a suction rate of, for example, 40 ml/min. This momen- tary high suction amount can potentially be ideal for the picking and placing of stone fragments to different areas of the kidney. During this time, the irrigation flow could automatically compensate for any changes in suction flow- rate to maintain an ideal pressure. Then when the doctor wants to release the stone fragment, they can select to reduce or eliminate the suction flow, thus releasing the stone.

EXAMPLES

The following examples are illustrative, but not limiting, of the devices, systems, and methods of the present inven- tion. Other suitable modifications and adaptations of the variety of conditions and parameters normally encountered in clinical therapy and which are obvious to those skilled in the art are within the spirit and scope of the invention.

Example 1

An experiment was performed that compared a Richard Wolf Cobra ureteroscope (See e.g., U.S. Pat. No. 9,089,297) to a ureteroscope of embodiments of the present disclosure. A variety of different stone sizes were tested. The suction rate was set to 60 ml/min through the suction channel. Then, the ureteroscope tip was lowered down to the stone such that the suction channel was in contact with the stone. The ureteroscope tip was then raised up and whether or not the stone was held onto the tip was recorded. This test was repeated 10 times with the stone being in a random orien- tation each time. The number of times the stone was held securely out of 10 was recorded.

The results show that while it is possible to reposition some stones using suction through the Richard Wolf Cobra scope, due to the tip shape there is difficulty picking up larger and more contoured stone fragments (particularly those above ~400 mg) (FIG. 10A). In contrast, using the device of embodiments of the present disclosure, the ability to pick up stones was significantly improved (compare FIGS. 32a-d and FIGS. 33a-d).

The results shown in FIGS. 32a-33d are summarized in Table A below:

TABLE A

| Stone mass | 194 | 207 | 422 | 460 |
|---|---|---|---|---|
| Richard Wolf Cobra ureteroscope | | | | |
| Success Rate | 10/10 | 10/10 | 3/10 | 0/10 |
| Devices from the present disclosure | | | | |
| Success Rate | 10/10 | 10/10 | 6/10 | 9/10 |

Figure 34:
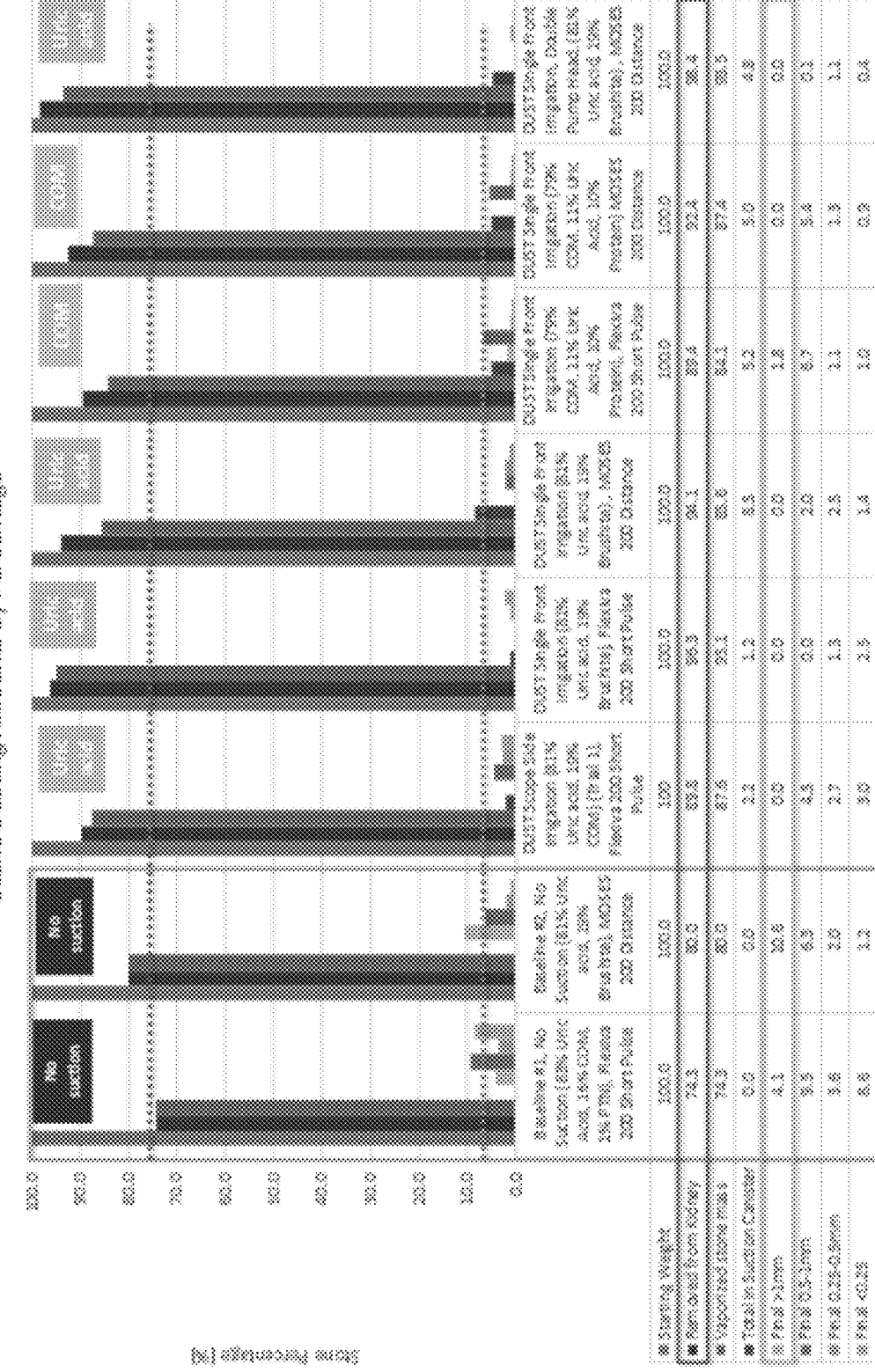
FIG. 34 is a table illustrating that suction enables better stone outcomes during kidney stone removal.

Further experiments demonstrated that, by removing the small particulates in a kidney stone simulation model, there is an improvement in not only vision but stone removal from the kidney over baseline that doesn't use suction. For example, in trials using a traditional kidney stone dusting procedure with no suction, approximately 75-80% of the stone mass was removed from the kidney model. In trials that utilized the suction between about 90-99% of the stone mass was removed from the kidney (FIG. 34).

The following items are examples of various embodiments disclosed above:

Item 1. An endoscopic device comprising a distal end, said distal end comprising: a) a first channel configured for delivery of fluid; and b) a second channel configured to remove fluid via suction, wherein the second channel exits said distal end on a different plane than said first channel and wherein the exit of said second channel comprises a suction port.

Item 2. An endoscopic device comprising a distal end, said distal end comprising: a) a first channel configured for delivery of fluid; and b) a second channel configured to remove fluid via suction, wherein the second channel exits said distal end on a different plane than said first channel and wherein the exit of said second channel comprises a suction port, and wherein at least one of said first and second channels are configured to prevent stones from occluding said suction port.

Item 3. An endoscopic device comprising a distal end, said distal end comprising: a) a first channel configured for delivery of fluid; and b) a second channel configured to remove fluid via suction, wherein the second channel exits said distal end on a different plane than said first channel and wherein the exit of said second channel comprises a suction port, wherein said suction port comprises a plurality of protrusions and/or depressions.

Item 4. An endoscopic device comprising a distal end, said distal end comprising: a) a first channel configured for delivery of fluid; and b) a second channel configured to remove fluid via suction, wherein the second channel exits said distal end on a different plane than said first channel and wherein the exit of said second channel comprises a suction port, and wherein said suction port is on a protrusion.

Item 5. An endoscopic device comprising a distal end, said distal end comprising: a) a first channel having an exit in a first plane configured for delivery of fluid; and b) a second channel having an exit in a second plane and wherein the exit of said second channel comprises a suction port.

Item 6. The endoscopic device of item 5, wherein exit of said first channel and/or said exit of said second channel is substantially planar.

Item 7. The endoscopic device of item 5, wherein exit of said first channel and/or said exit of said second channel is substantially in said first and/or second plane.

Item 8. The endoscopic device of items 1 to 7, wherein said suction port and the exit of said working channel are symmetrical.

Item 9. The endoscopic device of items 1 to 7, wherein said suction port and the exit of said working channel are asymmetrical.

Item 10. The endoscopic device of items 1 to 7, wherein said suction port and said working channel are interchangeable.

Item 11. The endoscopic device of items 1 to 10, wherein said suction port and said working channel are symmetrical and interchangeable.

Item 12. The endoscopic device of items 1 to 11, wherein the exit of said first channel is in a plane of said distal end.

Item 13. The endoscopic device of items 1 to 12, wherein said distal end of said endoscopic device further comprises one or more additional components selected from the group consisting of a camera and a light.

Item 14. The endoscopic device of item 13, wherein the location of said camera and said light are interchangeable.

Item 15. The endoscopic device of item 13 or 14, wherein said camera and said light are located proximal or distal to each other.

Item 16. The endoscopic device of items 13 to 15, wherein said camera is located on a plane above the plane of said working channel and/or suction port.

Item 17. The endoscopic device of item 16, wherein said working channel and/or said suction port are angled out and away from said camera.

Item 18. The endoscopic device of item 17, wherein said angled out and away is at an angle of 120-160 degrees about a X-axis of said endoscopic device and/or 5-25 degrees about a line positioned on the YZ-plane of said endoscopic device.

Item 19. The endoscopic device of item 13, wherein said light comprises a fiber optic filament.

Item 20. The endoscopic device of items 1 to 19, wherein said suction port comprises one or more anti-clog elements.

Item 21. The endoscopic device of item 20, wherein said anti-clog elements are selected from the group consisting of said suction port opening having a smaller opening area than suction tubing in operable communication with said opening, a mesh material that at least partially covers said opening, a bar or beam that at least partially covers said opening, an elastomeric element comprising one or more protrusions that at least partially cover said opening, and one or more protrusions or depressions adjacent to said opening.

Item 22. The endoscopic device of items 20 or 21, wherein said anti-clog elements reduces occlusion of said suction port and/or suction channel by a kidney stone or fragments thereof.

Item 23. The endoscopic device of items 1 to 22, wherein at least a portion of said distal end is constructed of a compliant material.

Item 24. The endoscopic device of item 23, wherein said compliant material is selected from the group consisting of a silicone elastomer, a thermoplastic elastomer, and a foam.

Item 25. The endoscopic device of item 23 or 24, wherein said compliant material surrounds or comprises said suction port.

Item 26. The endoscopic device of items 23 to 25, wherein said compliant material is configured to deform to fit the shape of a kidney stone.

Item 27. The endoscopic device of items 23 to 26, wherein said compliant material has a Shore hardness of OO10 and A40.

Item 28. The endoscopic device of items 23 to 27, wherein said compliant material is in the shape of a suction cup.

Item 29. The endoscopic device of items 1 to 28, wherein at least a portion of said distal end is constructed of a material selected from the group consisting of a thermoplastic, a metal, or a combination thereof.

Item 30. The endoscopic device of item 29, wherein said material has a hardness of greater than A40 on the Shore hardness scale.

Item 31. The endoscopic device of items 1 to 30, wherein the plane of the region of said distal end surrounding said suction port and/or working channel is flat, rounded, concave, or protruded.

Item 32. The endoscopic device of items 13 to 31, wherein said camera is positioned below, level, partially below, or partially above said suction port.

Item 33. The endoscopic device of item 32, wherein said camera is positioned in a cut out of said distal region.

Item 34. The endoscopic device of items 1 to 33, wherein said first and second channels are located adjacent or distal to each other.

Item 35. The endoscopic device of items 1 to 34, wherein said first channel is further configured for delivery of a laser.

Item 36. The endoscopic device of any one of items 1 to 34, wherein said endoscopic device comprises an outer housing surrounding an interstitial space, wherein said endoscopic device comprises at least one interstitial flow opening(s) in fluid communication with said interstitial space, wherein said interstitial flow opening(s) are configured to deliver fluid or suction through said interstitial space; and a fluid port.

Item 37. The endoscopic device of item 36, wherein said fluid port is located near the proximal end of said endoscopic device.

Item 38. The endoscopic device of any one of items 1 to 37, wherein said distal end further comprises one or more flow diverters, wherein said flow diverters are configured to direct fluid flow towards a channel or opening.

Item 39. The device of item 38, wherein said flow diverter is located at the opening of said first or second channel.

Item 40. The device of items 38 or 39, wherein said device comprises two or more of said flow diverters.

Item 41. The device of any one of items 1 to 40, wherein said first and second channels have different diameters.

Item 42. The device of item 41, wherein said first channel has an inner diameter of 0.4 to 0.6 mm and said second channel has an inner diameter of 1.1 to 1.3 mm.

Item 43. The device of any one of items 1 to 42, wherein the distal opening of said first and/or said second channels comprises a filter.

Item 44. The device of item 43, wherein said filter is pivotable and/or flexible.

Item 45. The device of item 43 or 44, wherein said filter is a mesh.

Item 46. The device of items 38 to 45, wherein said flow diverter is in fluid communication with said first and/or second channel.

Item 47. An endoscopic device comprising a distal end, said distal end comprising: a) a first channel or opening configured for delivery of fluid; and b) a second channel or opening configured to remove fluid via suction, and wherein said distal end further comprises one or more flow diverters, wherein said flow diverters are configured to direct fluid flow from said first channel or opening towards said second channel or opening.

Item 48. The device of item 47, wherein said flow diverter is located at the opening of said first or second channel.

Item 49. The device of items 47 or 48, wherein said device comprises two or more of said flow diverters.

Item 50. The device of any one of items 47 to 49, wherein said first and second channels have different diameters.

Item 51. The device of item 50, wherein said first channel has an inner diameter of 0.4 to 0.6 mm and said second channel has an inner diameter of 1.1 to 1.3 mm.

Item 52. The device of any one of items 47 to 51, wherein the distal opening of said first and/or said second channels comprises a filter.

Item 53. The device of item 52, wherein said filter is pivotable and/or flexible.

Item 54. The device of item 52 or 53, wherein said filter is a mesh.

Item 55. The device of items 47 to 54, wherein said flow diverter is in fluid communication with said first and/or second channel.

Item 56. An endoscopic device, comprising: an outer housing surrounding an interstitial space, wherein said endoscopic device comprises at least one interstitial flow opening(s) configured to deliver fluid or suction through said interstitial space.

Item 57. The endoscopic device of item 56, wherein said outer housing further comprises a fluid port in fluid communication with said interstitial space.

Item 58. The endoscopic device of items 56 or 57, wherein said fluid port is located at or near the proximal end of said endoscopic device.

Item 59. The endoscopic device of items 56 to 58, wherein said endoscopic device further comprises one or more working channels.

Item 60. The endoscopic device of items 56 to 59, wherein said interstitial space comprises one or more of a sensor wire, a camera wire, a pull wire, a light wire, a laser fiber, an a fiber optic wire.

Item 61. The endoscopic device of any one of items 56 to 60, wherein said distal end further comprises one or more flow diverters, wherein said flow diverters are configured to direct fluid flow towards a channel or opening.

Item 62. The endoscopic device of item 59, wherein said working channel further comprises one or more anti-clog elements selected from the group consisting of the opening of said working channel having a smaller opening area than suction tubing in operable communication with said opening, a mesh material that at least partially covers said opening, a bar or beam that at least partially covers said opening, an elastomeric element comprising one or more protrusions that at least partially cover said opening, and one or more protrusions or depressions adjacent to said opening.

Item 63. The endoscopic device of items 1 to 62, wherein said endoscopic device further comprises a laser slider, wherein said laser slider moves the laser fiber in the plane of the endoscopic device.

Item 64. The endoscopic device of item 63, wherein use of said laser slider dislodges clogged stones in said working channel Item 65. The endoscopic device of any one of items 1 to 64, wherein said endoscopic device is a ureteroscope.

Item 66. A system, comprising: a) the endoscopic device of any one of items 1 to 6; b) an irrigation delivery system; and c) a suction system.

Item 67. The system of item 66, wherein said system further comprises a temperature sensor and/or pressure sensor at said distal end.

Item 68. The system of items 66 or 67, wherein said system further comprises a computer system configured to adjust said irrigation delivery system and said suction system based on readings from said temperature and pressure sensors.

Item 69. The system of item 68, wherein said adjusting maintains temperature and/or pressure of fluid at said distal end within a range that reduces or prevents side effects due to excess pressure and/or temperature during use.

Item 70. A method of ablating a kidney stone, comprising: a) introducing the endoscopic device of any one of items 1 to 65 into the ureter of a subject; b) advancing the endoscopic device to a kidney stone; and c) ablating said stone using said endoscopic device.

Item 71. Use of an endoscopic device of any of items 1-65.

Item 72. Use of an endoscopic device of any of items 1-65 for the removal of a kidney stone.

The working channels and other channels are exemplified as having circular cross-sections. However, the present disclosure is not limited to a particular geometry of channel, channel openings, or ports. Other shapes are specifically contemplated, including oval and square, or other shapes. For example, in some embodiments, to minimize the outer diameter of the insertable portion while maximizing the open area of the working or other channel, it may be preferable to use a non-circular cross-sectional shape.

The present disclosure is not limited to a particular lighting technology. In some embodiments, commercially available lights are utilized, including, for example, one or more LED lights or fiber optic filaments. In some embodiments, the light illuminates the entire circumference of endoscope (e.g., using fiber optic technology to generate a ring of light).

The present disclosure is not limited to particular types and/or sources of lasers. In some embodiments, the laser is a Holmium:Ytrrium Aluminium Garnet (Ho:YAG) laser, although other lasers such as the Thulium Fiber Laser (TFL) may be used. In some embodiments, the laser fiber is a 230 μm or 365 μm fiber, or a 150 μm fiber or smaller if using the TFL.

In some embodiments, the irrigation fluid is saline (e.g., in a bag) delivered via tubing. In some embodiments, the irrigation fluid bag is held on a stand, pressurized, or connected to an automated delivery system.

All publications and patents mentioned in the above specification are herein incorporated by reference as if expressly set forth herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in relevant fields are intended to be within the scope of the following claims.

We claim:

1. An endoscope comprising:
a handle including a handle housing, a control lever, an irrigation inlet port adapted to receive irrigation fluid, and an irrigation channel;
pull wires connected to the control lever;

an insertion cord extending distally from the handle, the insertion cord including:
an insertion tube;
a bending section extending from the insertion tube, the bending section comprising hinged segments including a distal segment, the bending section being configured to bend responsive to the pull wires being tensioned;
a distal tip extending from the bending section and including a tip housing;
a camera at least partially enclosed in the tip housing;
a bending section cover;
interstitial space within the insertion tube in fluid communication with the irrigation channel; and
at least one interstitial flow opening in fluid communication with the interstitial space and adapted to discharge the irrigation fluid,
wherein the bending section cover overlaps, and is bonded to, the distal segment and/or the tip housing, at circumferentially spaced bonding sites with unbonded portions of the bending section cover disposed between the bonding sites, and
wherein the at least one interstitial flow opening comprises a gap between an unbonded and unperforated portion of the bending section cover and the distal segment and/or the tip housing.

2. The endoscope of claim 1, wherein the insertion cord further comprises components extending through the insertion tube, and wherein the interstitial space in the insertion tube comprises the space within the insertion tube not occupied by the components.

3. The endoscope of claim 1, wherein the tip housing comprises a distal wall and a circumferential wall extending proximally from the distal wall, and wherein the circumferential wall comprises at least one groove aligned with the gap, whereby when irrigation fluid is discharged through the at least one interstitial flow opening a flow of the irrigation fluid is at least in part directed by the groove.

4. The endoscope of claim 1, wherein the tip housing comprises a distal wall and a circumferential wall extending proximally from the distal wall, and wherein the at least one interstitial flow opening comprises a passage in the circumferential wall.

5. The endoscope of claim 1, wherein the tip housing comprises a distal wall and a circumferential wall extending proximally from the distal wall, and wherein the at least one interstitial flow opening comprises a passage in the distal wall.

6. The endoscope of claim 1, further comprising a component extending from the handle housing through the insertion tube and a fluid joint body inside the handle housing, the fluid joint body including:
an irrigation passage to sealingly and fluidly connect an internal space of the fluid joint body with the irrigation channel;
an insertion tube passage to sealingly receive the insertion tube and thereby establish fluid communication between the internal space and the interstitial space of the insertion tube; and
component inlet and outlet passages to receive the component, the component extending through the internal space from the inlet to the outlet.

7. The endoscope of claim 6, wherein the component comprises a working channel tube including a working channel therethrough, and wherein the working channel is fluidly isolated from the internal space by the component inlet and outlet passages.

8. The endoscope of claim 7, further comprising the pull wires and a cable connected to the camera, wherein the bending section includes a transverse wall including a passage sized and shaped to receive therethrough the working channel tube, the pull wires, and the cable.

9. The endoscope of claim 6, further comprising an irrigation tube in the handle housing, the irrigation tube comprising the irrigation channel, wherein the irrigation passage is sized and shaped to receive the irrigation tube.

10. The endoscope of claim 1, wherein the handle housing comprises circumferential walls and internal walls extending from the circumferential walls, and wherein the internal walls are sized and shaped to form the irrigation channel.

11. The endoscope of claim 1, wherein the tip housing includes a working channel port in fluid communication with the working channel and a flow diverter sized and structured to mitigate or prevent occlusion of the working channel port.

12. A visualization system comprising:

the endoscope of claim 1; and a video processing apparatus operable to receive live images from the endoscope.

13. A method of irrigating a space within a patient, the method comprising:

inserting the insertion cord of the endoscope of claim 1 into the patient;

supplying irrigation fluid to the irrigation channel of the endoscope, the irrigation fluid flowing through the interstitial space and discharging through the at least one interstitial flow opening to irrigate the space.

14. The endoscope of claim 1, wherein the tip housing comprises a distal wall and a circumferential wall extending proximally from the distal wall, and wherein the circumferential wall comprises at least one groove aligned with the gap, whereby when irrigation fluid is discharged through the at least one interstitial flow opening a flow of the irrigation fluid is at least in part directed by the groove.

15. An endoscope comprising:

a handle including a handle housing, a control lever, an irrigation inlet port adapted to receive irrigation fluid, and an irrigation channel;

pull wires connected to the control lever;

an insertion cord extending distally from the handle, the insertion cord including:

an insertion tube;

a bending section extending from the insertion tube, the bending section comprising hinged segments including a distal segment and being configured to bend responsive to the pull wires being tensioned;

a distal tip extending from the bending section and including a tip housing;

a camera at least partially enclosed in the tip housing;

a bending section cover;

interstitial space within the insertion tube in fluid communication with the irrigation channel; and at least one interstitial flow opening in fluid communication with the interstitial space and adapted to discharge the irrigation fluid, the at least one interstitial flow opening comprising a slit in the bending section cover or a gap between the bending section cover and (a) the distal segment and/or (b) the tip housing, wherein the at least one interstitial flow opening is a pressure-dependent interstitial fluid opening which is closed when relaxed and open responsive to fluid pressure.

16. The endoscope of claim 15, wherein the gap is formed between the bending section cover and an unperforated portion of the distal segment of the bending section and/or the tip housing.

17. The endoscope of claim 15, wherein the bending section cover overlaps, and is bonded to, the distal segment and/or the tip housing, at circumferentially spaced bonding sites with unbonded portions of the bending section cover disposed between the bonding sites, and wherein the gap is formed between an unbonded and unperforated portion of the bending section cover and the distal segment and/or the tip housing.

18. An endoscope comprising:

a handle including a handle housing, a control lever, an irrigation inlet port adapted to receive irrigation fluid, and an irrigation channel;

pull wires connected to the control lever:

an insertion cord extending distally from the handle, the insertion cord including:

an insertion tube;

a bending section extending from the insertion tube, the bending section comprising hinged segments including a distal segment and being configured to bend responsive to the pull wires being tensioned;

a distal tip extending from the bending section and including a tip housing;

a camera at least partially enclosed in the tip housing;

a bending section cover;

interstitial space within the insertion tube in fluid communication with the irrigation channel; and at least one interstitial flow opening in fluid communication with the interstitial space and adapted to discharge the irrigation fluid, wherein the at least one interstitial flow opening comprises a slit in the bending section cover, and wherein the slit is pressure-dependent such that it is closed when relaxed and open responsive to fluid pressure.

* * * * *